(12) United States Patent
Kopetzki et al.

(10) Patent No.: US 11,098,338 B2
(45) Date of Patent: Aug. 24, 2021

(54) RECOMBINANT POLYPEPTIDE PRODUCTION METHODS

(71) Applicant: Hoffmann-La Roche Inc., Little Falls, NJ (US)

(72) Inventors: Erhard Kopetzki, Penzberg (DE); Jens Niewoehner, Munich (DE); Peter Maier, Biberach an der Riss (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/413,063

(22) Filed: May 15, 2019

(65) Prior Publication Data

US 2019/0271021 A1 Sep. 5, 2019

Related U.S. Application Data

(63) Continuation of application No. 15/106,205, filed as application No. PCT/EP2014/077196 on Dec. 10, 2014, now Pat. No. 10,370,692.

(30) Foreign Application Priority Data

Dec. 20, 2013 (EP) .................................... 13198738

(51) Int. Cl.
| | |
|---|---|
| *C12P 21/00* | (2006.01) |
| *C07K 14/475* | (2006.01) |
| *C12P 21/02* | (2006.01) |
| *C07K 16/28* | (2006.01) |
| *C07K 5/10* | (2006.01) |
| *C07K 5/11* | (2006.01) |
| *C07K 14/48* | (2006.01) |

(52) U.S. Cl.
CPC .......... *C12P 21/005* (2013.01); *C07K 5/1019* (2013.01); *C07K 14/475* (2013.01); *C07K 14/48* (2013.01); *C07K 16/2863* (2013.01); *C07K 16/2881* (2013.01); *C12P 21/02* (2013.01); *C07K 2317/14* (2013.01); *C07K 2317/522* (2013.01); *C07K 2317/524* (2013.01); *C07K 2317/526* (2013.01); *C07K 2317/53* (2013.01); *C07K 2317/55* (2013.01); *C07K 2317/56* (2013.01); *C07K 2319/00* (2013.01); *C07K 2319/50* (2013.01); *C07K 2319/60* (2013.01)

(58) Field of Classification Search
CPC C07K 2319/30; C07K 2317/41; C12P 21/005
See application file for complete search history.

(56) References Cited

U.S. PATENT DOCUMENTS

2002/0127652 A1* 9/2002 Schambye ........... A61K 47/646
435/69.4

OTHER PUBLICATIONS

Bulbarelli et al., "Trafficking of tail-anchored proteins: transport from the endoplasmic reticulum to the plasma membrane and sorting between surface domains in polarised epithelial cells", Journal of Cell Science, 2002, vol. 115, pp. 1689-1702.*
Jost et al., "Mammalian Expression and Secretion of Functional Single-chain Fv Molecules", The Journal of Biological Chemistry, 1994, vol. 269, No. 42, Issue of Oct. 21, p. 26267-26273.*
Perlman et al., "Glycosylation of an N-Terminal Extension Prolongs the Half-Life and Increases the in Vivo Activity of Follicle Stimulating Hormone", The Journal of Clinical Endocrinology & Metabolism, 2003, 88(7):3227-3235. doi: 10.1210/jc.2002-021201.*
Meder et al., "Gp135/podocalyxin and NHERF-2 participate in the formation of a preapical domain during polarization of MDCK cells", Journal of Cell Biology, 2005, 168(2):303-313.*

* cited by examiner

*Primary Examiner* — Suzanne M Noakes

(57) ABSTRACT

Herein is reported a method for producing a fusion-polypeptide comprising the seeps of a) cultivating a mammalian cell comprising a nucleic acid encoding a variant fusion-polypeptide wherein the amino acid sequence of the fusion-polypeptide has been modified by replacing in a pro-fusion-polypeptide the endogenous protease cleavage site between the pro-peptide and the fusion-polypeptide with an exogenous (with respect to the origins of the parts of the fusion-polypeptide) or artificial protease cleavage site, and b) recovering the fusion-polypeptide or fusion-pro-polypeptide from the cell or the cultivation median and thereby producing the (recombinant) fusion-polypeptide.

4 Claims, 4 Drawing Sheets
Specification includes a Sequence Listing.

SEQUENCE LISTING

```
<160> NUMBER OF SEQ ID NOS: 109

<210> SEQ ID NO 1
<211> LENGTH: 11
<212> TYPE: PRT
<213> ORGANISM: Artificial Sequence
<220> FEATURE:
<223> OTHER INFORMATION: GlySer-linker

<400> SEQUENCE: 1

Gly Gly Gly Gly Ser Gly Gly Gly Ser Gly
1               5                   10

<210> SEQ ID NO 2
<211> LENGTH: 239
<212> TYPE: PRT
<213> ORGANISM: Artificial Sequence
<220> FEATURE:
<223> OTHER INFORMATION: enhanced green fluorescent protein

<400> SEQUENCE: 2

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220
```

```
Val Thr Ala Ala Gly Ile Thr Leu Gly Met Asp Glu Leu Tyr Lys
225                 230                 235
```

<210> SEQ ID NO 3
<211> LENGTH: 239
<212> TYPE: PRT
<213> ORGANISM: Artificial Sequence
<220> FEATURE:
<223> OTHER INFORMATION: emerald green fluorescent protein

<400> SEQUENCE: 3

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Lys Val Tyr Ile Thr Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 4
<211> LENGTH: 238
<212> TYPE: PRT
<213> ORGANISM: Artificial Sequence
<220> FEATURE:
<223> OTHER INFORMATION: tagGFP

<400> SEQUENCE: 4

```
Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
```

```
            50                  55                  60
Cys Tyr Gly Ile Gln Cys Phe Ala Arg Tyr Pro Glu His Met Lys Met
 65                  70                  75                  80

Asn Asp Phe Phe Lys Ser Ala Met Pro Glu Gly Tyr Ile Gln Glu Arg
                     85                  90                  95

Thr Ile Gln Phe Gln Asp Asp Gly Lys Tyr Lys Thr Arg Gly Glu Val
                100                 105                 110

Lys Phe Glu Gly Asp Thr Leu Val Asn Arg Ile Glu Leu Lys Gly Lys
            115                 120                 125

Asp Phe Lys Glu Asp Gly Asn Ile Leu Gly His Lys Leu Glu Tyr Ser
130                 135                 140

Phe Asn Ser His Asn Val Tyr Ile Arg Pro Asp Lys Ala Asn Asn Gly
145                 150                 155                 160

Leu Glu Ala Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Lys Ile Ser
        195                 200                 205

Lys Asp Arg Asn Glu Ala Arg Asp His Met Val Leu Leu Glu Ser Phe
210                 215                 220

Ser Ala Cys Cys His Thr His Gly Met Asp Glu Leu Tyr Arg
225                 230                 235

<210> SEQ ID NO 5
<211> LENGTH: 448
<212> TYPE: PRT
<213> ORGANISM: Artificial Sequence
<220> FEATURE:
<223> OTHER INFORMATION: anti-IGF-1R antibody HC

<400> SEQUENCE: 5

Gln Val Glu Leu Val Glu Ser Gly Gly Gly Val Val Gln Pro Gly Arg
 1               5                  10                  15

Ser Gln Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Ile Ile Trp Phe Asp Gly Ser Ser Thr Tyr Tyr Ala Asp Ser Val
     50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                 85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
```

```
                180                 185                 190
Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 6
<211> LENGTH: 215
<212> TYPE: PRT
<213> ORGANISM: Artificial Sequence
<220> FEATURE:
<223> OTHER INFORMATION: anti-IGF-1R antibody LC

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys Arg Thr Val Ala
```

```
            100                 105                 110
Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 7
<211> LENGTH: 715
<212> TYPE: PRT
<213> ORGANISM: Artificial Sequence
<220> FEATURE:
<223> OTHER INFORMATION: anti-IGF-1R antibody HC - eGFP fusion
      polypeptide

<400> SEQUENCE: 7

Met Gly Trp Ser Cys Ile Ile Leu Phe Leu Val Ala Thr Ala Thr Gly
1               5                   10                  15

Val His Ser Gln Val Glu Leu Val Glu Ser Gly Gly Gly Val Val Gln
                20                  25                  30

Pro Gly Arg Ser Gln Arg Leu Ser Cys Ala Ala Ser Gly Phe Thr Phe
            35                  40                  45

Ser Ser Tyr Gly Met His Trp Val Arg Gln Ala Pro Gly Lys Gly Leu
        50                  55                  60

Glu Trp Val Ala Ile Ile Trp Phe Asp Gly Ser Ser Thr Tyr Tyr Ala
65                  70                  75                  80

Asp Ser Val Arg Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Phe Cys Ala Arg Glu Leu Gly Arg Arg Tyr Phe Asp Leu Trp Gly
        115                 120                 125

Arg Gly Thr Leu Val Ser Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240
```

```
Asp Lys Thr His Thr Cys Pro Pro Cys Pro Ala Glu Leu Leu Gly
            245                 250                 255
Gly Pro Ser Val Phe Leu Phe Pro Pro Lys Pro Lys Asp Thr Leu Met
        260                 265                 270
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Gly Gly Gly Ser Gly Gly Gly Gly Ser Gly Met Val Ser Lys
465                 470                 475                 480
Gly Glu Glu Leu Phe Thr Gly Val Val Pro Ile Leu Val Glu Leu Asp
                485                 490                 495
Gly Asp Val Asn Gly His Lys Phe Ser Val Ser Gly Glu Gly Glu Gly
            500                 505                 510
Asp Ala Thr Tyr Gly Lys Leu Thr Leu Lys Phe Ile Cys Thr Thr Gly
        515                 520                 525
Lys Leu Pro Val Pro Trp Pro Thr Leu Val Thr Thr Leu Thr Tyr Gly
    530                 535                 540
Val Gln Cys Phe Ser Arg Tyr Pro Asp His Met Lys Gln His Asp Phe
545                 550                 555                 560
Phe Lys Ser Ala Met Pro Glu Gly Tyr Val Gln Glu Arg Thr Ile Phe
                565                 570                 575
Phe Lys Asp Asp Gly Asn Tyr Lys Thr Arg Ala Glu Val Lys Phe Glu
            580                 585                 590
Gly Asp Thr Leu Val Asn Arg Ile Glu Leu Lys Gly Ile Asp Phe Lys
        595                 600                 605
Glu Asp Gly Asn Ile Leu Gly His Lys Leu Glu Tyr Asn Tyr Asn Ser
    610                 615                 620
His Asn Val Tyr Ile Met Ala Asp Lys Gln Lys Asn Gly Ile Lys Val
625                 630                 635                 640
Asn Phe Lys Ile Arg His Asn Ile Glu Asp Gly Ser Val Gln Leu Ala
                645                 650                 655
Asp His Tyr Gln Gln Asn Thr Pro Ile Gly Asp Gly Pro Val Leu Leu
```

```
                    660                 665                 670
Pro Asp Asn His Tyr Leu Ser Thr Gln Ser Ala Leu Ser Lys Asp Pro
            675                 680                 685

Asn Glu Lys Arg Asp His Met Val Leu Leu Glu Phe Val Thr Ala Ala
        690                 695                 700

Gly Ile Thr Leu Gly Met Asp Glu Leu Tyr Lys
705                 710                 715

<210> SEQ ID NO 8
<211> LENGTH: 715
<212> TYPE: PRT
<213> ORGANISM: Artificial Sequence
<220> FEATURE:
<223> OTHER INFORMATION: anti-IGF-1R antibody HC - emGFP fusion
      polypeptide

<400> SEQUENCE: 8

Met Gly Trp Ser Cys Ile Ile Leu Phe Leu Val Ala Thr Ala Thr Gly
1               5                   10                  15

Val His Ser Gln Val Glu Leu Val Glu Ser Gly Gly Gly Val Val Gln
            20                  25                  30

Pro Gly Arg Ser Gln Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Ile Ile Trp Phe Asp Gly Ser Ser Thr Tyr Tyr Ala
65                  70                  75                  80

Asp Ser Val Arg Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Phe Cys Ala Arg Glu Leu Gly Arg Arg Tyr Phe Asp Leu Trp Gly
        115                 120                 125

Arg Gly Thr Leu Val Ser Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300
```

```
His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
450                 455                 460

Pro Gly Gly Gly Gly Ser Gly Gly Gly Gly Ser Gly Met Val Ser Lys
465                 470                 475                 480

Gly Glu Glu Leu Phe Thr Gly Val Val Pro Ile Leu Val Glu Leu Asp
            485                 490                 495

Gly Asp Val Asn Gly His Lys Phe Ser Val Ser Gly Glu Gly Glu Gly
        500                 505                 510

Asp Ala Thr Tyr Gly Lys Leu Thr Leu Lys Phe Ile Cys Thr Thr Gly
    515                 520                 525

Lys Leu Pro Val Pro Trp Pro Thr Leu Val Thr Thr Leu Thr Tyr Gly
530                 535                 540

Val Gln Cys Phe Ala Arg Tyr Pro Asp His Met Lys Gln His Asp Phe
545                 550                 555                 560

Phe Lys Ser Ala Met Pro Glu Gly Tyr Val Gln Glu Arg Thr Ile Phe
            565                 570                 575

Phe Lys Asp Asp Gly Asn Tyr Lys Thr Arg Ala Glu Val Lys Phe Glu
        580                 585                 590

Gly Asp Thr Leu Val Asn Arg Ile Glu Leu Lys Gly Ile Asp Phe Lys
    595                 600                 605

Glu Asp Gly Asn Ile Leu Gly His Lys Leu Glu Tyr Asn Tyr Asn Ser
610                 615                 620

His Lys Val Tyr Ile Thr Ala Asp Lys Gln Lys Asn Gly Ile Lys Val
625                 630                 635                 640

Asn Phe Lys Thr Arg His Asn Ile Glu Asp Gly Ser Val Gln Leu Ala
            645                 650                 655

Asp His Tyr Gln Gln Asn Thr Pro Ile Gly Asp Gly Pro Val Leu Leu
        660                 665                 670

Pro Asp Asn His Tyr Leu Ser Thr Gln Ser Ala Leu Ser Lys Asp Pro
    675                 680                 685

Asn Glu Lys Arg Asp His Met Val Leu Leu Glu Phe Val Thr Ala Ala
690                 695                 700

Gly Ile Thr Leu Gly Met Asp Glu Leu Tyr Lys
705                 710                 715
```

<210> SEQ ID NO 9
<211> LENGTH: 714
<212> TYPE: PRT
<213> ORGANISM: Artificial Sequence
<220> FEATURE:
<223> OTHER INFORMATION: anti-IGF-1R antibody HC - tagGFP fusion polypeptide

<400> SEQUENCE: 9

```
Met Gly Trp Ser Cys Ile Ile Leu Phe Leu Val Ala Thr Ala Thr Gly
1               5                   10                  15

Val His Ser Gln Val Glu Leu Val Glu Ser Gly Gly Gly Val Val Gln
            20                  25                  30

Pro Gly Arg Ser Gln Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Ile Ile Trp Phe Asp Gly Ser Ser Thr Tyr Tyr Ala
65                  70                  75                  80

Asp Ser Val Arg Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Phe Cys Ala Arg Glu Leu Gly Arg Arg Tyr Phe Asp Leu Trp Gly
        115                 120                 125

Arg Gly Thr Leu Val Ser Val Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365
```

```
Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Gly Gly Ser Gly Gly Gly Ser Gly Met Ser Gly Gly
465                 470                 475                 480

Glu Glu Leu Phe Ala Gly Ile Val Pro Val Leu Ile Glu Leu Asp Gly
                485                 490                 495

Asp Val His Gly His Lys Phe Ser Val Arg Gly Glu Gly Glu Gly Asp
                500                 505                 510

Ala Asp Tyr Gly Lys Leu Glu Ile Lys Phe Ile Cys Thr Thr Gly Lys
            515                 520                 525

Leu Pro Val Pro Trp Pro Thr Leu Val Thr Thr Leu Cys Tyr Gly Ile
530                 535                 540

Gln Cys Phe Ala Arg Tyr Pro Glu His Met Lys Met Asn Asp Phe Phe
545                 550                 555                 560

Lys Ser Ala Met Pro Glu Gly Tyr Ile Gln Glu Arg Thr Ile Gln Phe
                565                 570                 575

Gln Asp Asp Gly Lys Tyr Lys Thr Arg Gly Glu Val Lys Phe Glu Gly
                580                 585                 590

Asp Thr Leu Val Asn Arg Ile Glu Leu Lys Gly Lys Asp Phe Lys Glu
            595                 600                 605

Asp Gly Asn Ile Leu Gly His Lys Leu Glu Tyr Ser Phe Asn Ser His
610                 615                 620

Asn Val Tyr Ile Arg Pro Asp Lys Ala Asn Asn Gly Leu Glu Ala Asn
625                 630                 635                 640

Phe Lys Thr Arg His Asn Ile Glu Gly Gly Gly Val Gln Leu Ala Asp
                645                 650                 655

His Tyr Gln Thr Asn Val Pro Leu Gly Asp Gly Pro Val Leu Ile Pro
            660                 665                 670

Ile Asn His Tyr Leu Ser Thr Gln Thr Lys Ile Ser Lys Asp Arg Asn
675                 680                 685

Glu Ala Arg Asp His Met Val Leu Leu Glu Ser Phe Ser Ala Cys Cys
690                 695                 700

His Thr His Gly Met Asp Glu Leu Tyr Arg
705                 710

<210> SEQ ID NO 10
<211> LENGTH: 19
<212> TYPE: PRT
<213> ORGANISM: Artificial Sequence
<220> FEATURE:
<223> OTHER INFORMATION: human opsin receptor derived polypeptide =
      opsin-tag

<400> SEQUENCE: 10

Asn Gly Thr Glu Gly Pro Asn Phe Tyr Val Pro Phe Ser Asn Ala Thr
1               5                   10                  15
```

Gly Val Val

<210> SEQ ID NO 11
<211> LENGTH: 734
<212> TYPE: PRT
<213> ORGANISM: Artificial Sequence
<220> FEATURE:
<223> OTHER INFORMATION: anti-IGF-1R antibody HC eGFP opsin-tag fusion polypeptide

<400> SEQUENCE: 11

```
Met Gly Trp Ser Cys Ile Ile Leu Phe Leu Val Ala Thr Ala Thr Gly
1               5                   10                  15

Val His Ser Gln Val Glu Leu Val Glu Ser Gly Gly Val Val Gln
            20                  25                  30

Pro Gly Arg Ser Gln Arg Leu Ser Cys Ala Ala Ser Gly Phe Thr Phe
            35                  40                  45

Ser Ser Tyr Gly Met His Trp Val Arg Gln Ala Pro Gly Lys Gly Leu
        50                  55                  60

Glu Trp Val Ala Ile Ile Trp Phe Asp Gly Ser Ser Thr Tyr Tyr Ala
65                  70                  75                  80

Asp Ser Val Arg Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Phe Cys Ala Arg Glu Leu Gly Arg Arg Tyr Phe Asp Leu Trp Gly
        115                 120                 125

Arg Gly Thr Leu Val Ser Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350
```

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Gly Gly Gly Ser Gly Gly Gly Gly Ser Gly Met Val Ser Lys
465                 470                 475                 480

Gly Glu Glu Leu Phe Thr Gly Val Val Pro Ile Leu Val Glu Leu Asp
                485                 490                 495

Gly Asp Val Asn Gly His Lys Phe Ser Val Ser Gly Glu Gly Glu Gly
            500                 505                 510

Asp Ala Thr Tyr Gly Lys Leu Thr Leu Lys Phe Ile Cys Thr Thr Gly
            515                 520                 525

Lys Leu Pro Val Pro Trp Pro Thr Leu Val Thr Thr Leu Thr Tyr Gly
            530                 535                 540

Val Gln Cys Phe Ser Arg Tyr Pro Asp His Met Lys Gln His Asp Phe
545                 550                 555                 560

Phe Lys Ser Ala Met Pro Glu Gly Tyr Val Gln Glu Arg Thr Ile Phe
                565                 570                 575

Phe Lys Asp Asp Gly Asn Tyr Lys Thr Arg Ala Glu Val Lys Phe Glu
            580                 585                 590

Gly Asp Thr Leu Val Asn Arg Ile Glu Leu Lys Gly Ile Asp Phe Lys
            595                 600                 605

Glu Asp Gly Asn Ile Leu Gly His Lys Leu Glu Tyr Asn Tyr Asn Ser
610                 615                 620

His Asn Val Tyr Ile Met Ala Asp Lys Gln Lys Asn Gly Ile Lys Val
625                 630                 635                 640

Asn Phe Lys Ile Arg His Asn Ile Glu Asp Gly Ser Val Gln Leu Ala
                645                 650                 655

Asp His Tyr Gln Gln Asn Thr Pro Ile Gly Asp Gly Pro Val Leu Leu
            660                 665                 670

Pro Asp Asn His Tyr Leu Ser Thr Gln Ser Ala Leu Ser Lys Asp Pro
            675                 680                 685

Asn Glu Lys Arg Asp His Met Val Leu Leu Glu Phe Val Thr Ala Ala
            690                 695                 700

Gly Ile Thr Leu Gly Met Asp Glu Leu Tyr Lys Asn Gly Thr Glu Gly
705                 710                 715                 720

Pro Asn Phe Tyr Val Pro Phe Ser Asn Ala Thr Gly Val Val
                725                 730

<210> SEQ ID NO 12
<211> LENGTH: 17
<212> TYPE: PRT
<213> ORGANISM: Artificial Sequence
<220> FEATURE:

<223> OTHER INFORMATION: T7-His6 tag

<400> SEQUENCE: 12

Met Ala Ser Met Thr Gly Gly Gln Gln Met Gly His His His His
1               5                   10                  15

His

<210> SEQ ID NO 13
<211> LENGTH: 267
<212> TYPE: PRT
<213> ORGANISM: Artificial Sequence
<220> FEATURE:
<223> OTHER INFORMATION: pre-pro-BDNF-T7-His6

<400> SEQUENCE: 13

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg Gly Ser Gly Met Ala Ser Met Thr Gly
                245                 250                 255

Gly Gln Gln Met Gly His His His His His
            260                 265

<210> SEQ ID NO 14
<211> LENGTH: 19
<212> TYPE: PRT
<213> ORGANISM: Mus musculus

<400> SEQUENCE: 14

Met Gly Trp Ser Cys Ile Ile Leu Phe Leu Val Ala Thr Ala Thr Gly

```
1               5                  10                 15

Val His Ser

<210> SEQ ID NO 15
<211> LENGTH: 16
<212> TYPE: PRT
<213> ORGANISM: Artificial Sequence
<220> FEATURE:
<223> OTHER INFORMATION: short opsin-tag

<400> SEQUENCE: 15

Asn Gly Thr Glu Gly Pro Asn Phe Tyr Val Pro Phe Ser Asn Ala Thr
1               5                  10                 15

<210> SEQ ID NO 16
<211> LENGTH: 20
<212> TYPE: PRT
<213> ORGANISM: Artificial Sequence
<220> FEATURE:
<223> OTHER INFORMATION: long opsin-tag

<400> SEQUENCE: 16

Asn Gly Thr Glu Gly Pro Asn Phe Tyr Val Pro Phe Ser Asn Ala Thr
1               5                  10                 15

Gly Val Val Arg
            20

<210> SEQ ID NO 17
<211> LENGTH: 9
<212> TYPE: PRT
<213> ORGANISM: Artificial Sequence
<220> FEATURE:
<223> OTHER INFORMATION: glycosylation-tag

<400> SEQUENCE: 17

Ala Ala Ala Asn Gly Thr Gly Gly Ala
1               5

<210> SEQ ID NO 18
<211> LENGTH: 9
<212> TYPE: PRT
<213> ORGANISM: Artificial Sequence
<220> FEATURE:
<223> OTHER INFORMATION: glycosylation-tag

<400> SEQUENCE: 18

Ala Asn Ile Thr Val Asn Ile Thr Val
1               5

<210> SEQ ID NO 19
<211> LENGTH: 12
<212> TYPE: PRT
<213> ORGANISM: Artificial Sequence
<220> FEATURE:
<223> OTHER INFORMATION: glycosylation-tag

<400> SEQUENCE: 19

Asn Ala Thr Gly Ala Asp Asn Gly Thr Gly Ala Ser
1               5                  10

<210> SEQ ID NO 20
<211> LENGTH: 247
<212> TYPE: PRT
<213> ORGANISM: Homo sapiens

<400> SEQUENCE: 20
```

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
            195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245

<210> SEQ ID NO 21
<211> LENGTH: 4
<212> TYPE: PRT
<213> ORGANISM: Homo sapiens

<400> SEQUENCE: 21

Arg Val Arg Arg
1

<210> SEQ ID NO 22
<211> LENGTH: 9
<212> TYPE: PRT
<213> ORGANISM: Artificial Sequence
<220> FEATURE:
<223> OTHER INFORMATION: IgA protease cleavage sequence

<400> SEQUENCE: 22

Gly Ser Val Val Ala Pro Pro Ala Pro
1               5

<210> SEQ ID NO 23
<211> LENGTH: 6
<212> TYPE: PRT
<213> ORGANISM: Artificial Sequence
<220> FEATURE:
```

<223> OTHER INFORMATION: His6-tag

<400> SEQUENCE: 23

His His His His His His
1               5

<210> SEQ ID NO 24
<211> LENGTH: 3
<212> TYPE: PRT
<213> ORGANISM: Homo sapiens

<400> SEQUENCE: 24

Arg Gly Arg
1

<210> SEQ ID NO 25
<211> LENGTH: 119
<212> TYPE: PRT
<213> ORGANISM: Homo sapiens

<400> SEQUENCE: 25

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg
        115

<210> SEQ ID NO 26
<211> LENGTH: 12
<212> TYPE: PRT
<213> ORGANISM: Artificial Sequence
<220> FEATURE:
<223> OTHER INFORMATION: linker peptide

<400> SEQUENCE: 26

Gly Gly Gly Gly Ser Gly Gly Gly Gly Ser Gly Gly
1               5                   10

<210> SEQ ID NO 27
<211> LENGTH: 22
<212> TYPE: PRT
<213> ORGANISM: Artificial Sequence
<220> FEATURE:
<223> OTHER INFORMATION: linker peptide

<400> SEQUENCE: 27

Gly Gly Gly Gly Ser Gly Gly Gly Gly Ser Gly Gly Gly Gly Ser Gly
1               5                   10                  15

Gly Gly Gly Ser Gly Gly
            20

<210> SEQ ID NO 28
<211> LENGTH: 32
<212> TYPE: PRT
<213> ORGANISM: Artificial Sequence
<220> FEATURE:
<223> OTHER INFORMATION: linker peptide

<400> SEQUENCE: 28

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Ser Gly Gly
            20                  25                  30

<210> SEQ ID NO 29
<211> LENGTH: 24
<212> TYPE: PRT
<213> ORGANISM: Artificial Sequence
<220> FEATURE:
<223> OTHER INFORMATION: linker peptide

<400> SEQUENCE: 29

Gly Gly Gly Asp Gly Gly Gly Asp Gly Gly Gly Asp Gly Gly Gly Asp
1               5                   10                  15

Gly Gly Gly Asp Gly Gly Gly Ser
            20

<210> SEQ ID NO 30
<211> LENGTH: 15
<212> TYPE: PRT
<213> ORGANISM: Artificial Sequence
<220> FEATURE:
<223> OTHER INFORMATION: linker peptide

<400> SEQUENCE: 30

Gly Gly Gly Gly Ser Gly Gly Gly Ser Gly Gly Gly Gly Ser
1               5                   10                  15

<210> SEQ ID NO 31
<211> LENGTH: 19
<212> TYPE: PRT
<213> ORGANISM: Artificial Sequence
<220> FEATURE:
<223> OTHER INFORMATION: linker peptide

<400> SEQUENCE: 31

Gly Gly Asp Gly Gly Asp Gly Gly Asp Gly Gly Asp Gly Gly Asp Gly
1               5                   10                  15

Gly Ser Gly

<210> SEQ ID NO 32
<211> LENGTH: 19
<212> TYPE: PRT
<213> ORGANISM: Artificial Sequence
<220> FEATURE:
<223> OTHER INFORMATION: linker peptide

<400> SEQUENCE: 32

Gly Gly Asp Gly Gly Asp Gly Gly Asp Gly Gly Asp Gly Gly Asp Gly
1               5                   10                  15

Gly Gly Ser

<210> SEQ ID NO 33
<211> LENGTH: 734
<212> TYPE: PRT

<213> ORGANISM: Artificial Sequence
<220> FEATURE:
<223> OTHER INFORMATION: HC<IGF-1R>_(G4S)2G_eGFP-2N

<400> SEQUENCE: 33

```
Met Gly Trp Ser Cys Ile Ile Leu Phe Leu Val Ala Thr Ala Thr Gly
1               5                   10                  15

Val His Ser Gln Val Glu Leu Val Glu Ser Gly Gly Val Val Gln
            20                  25                  30

Pro Gly Arg Ser Gln Arg Leu Ser Cys Ala Ala Ser Gly Phe Thr Phe
            35                  40                  45

Ser Ser Tyr Gly Met His Trp Val Arg Gln Ala Pro Gly Lys Gly Leu
        50                  55                  60

Glu Trp Val Ala Ile Ile Trp Phe Asp Gly Ser Ser Thr Tyr Tyr Ala
65                  70                  75                  80

Asp Ser Val Arg Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Phe Cys Ala Arg Glu Leu Gly Arg Arg Tyr Phe Asp Leu Trp Gly
        115                 120                 125

Arg Gly Thr Leu Val Ser Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
```

-continued

```
            385                 390                 395                 400
        Trp Glu Ser Asn Gly Gln Pro Glu Asn Tyr Lys Thr Thr Pro Pro
                        405                 410                 415

Val Leu Asp Ser Asp Gly Ser Phe Phe Leu Tyr Ser Lys Leu Thr Val
                        420                 425                 430

Asp Lys Ser Arg Trp Gln Gln Gly Asn Val Phe Ser Cys Ser Val Met
                        435                 440                 445

His Glu Ala Leu His Asn His Tyr Thr Gln Lys Ser Leu Ser Leu Ser
                450                 455                 460

Pro Gly Gly Gly Ser Gly Gly Gly Ser Gly Met Val Ser Lys
        465                 470                 475                 480

Gly Glu Glu Leu Phe Thr Gly Val Val Pro Ile Leu Val Glu Leu Asp
                        485                 490                 495

Gly Asp Val Asn Gly His Lys Phe Ser Val Ser Gly Glu Gly Glu Gly
                        500                 505                 510

Asp Ala Thr Tyr Gly Lys Leu Thr Leu Lys Phe Ile Cys Thr Thr Gly
                        515                 520                 525

Lys Leu Pro Val Pro Trp Pro Thr Leu Val Thr Thr Leu Thr Tyr Gly
                530                 535                 540

Val Gln Cys Phe Ser Arg Tyr Pro Asp His Met Lys Gln His Asp Phe
        545                 550                 555                 560

Phe Lys Ser Ala Met Pro Glu Gly Tyr Val Gln Glu Arg Thr Ile Phe
                        565                 570                 575

Phe Lys Asp Asp Gly Asn Tyr Lys Thr Arg Ala Glu Val Lys Phe Glu
                        580                 585                 590

Gly Asp Thr Leu Val Asn Arg Ile Glu Leu Lys Gly Ile Asp Phe Lys
                        595                 600                 605

Glu Asp Gly Asn Ile Leu Gly His Lys Leu Glu Tyr Asn Tyr Asn Ser
                        610                 615                 620

His Asn Val Tyr Ile Met Ala Asp Lys Gln Lys Asn Gly Ile Lys Val
        625                 630                 635                 640

Asn Phe Lys Ile Arg His Asn Ile Glu Asp Gly Ser Val Gln Leu Ala
                        645                 650                 655

Asp His Tyr Gln Gln Asn Thr Pro Ile Gly Asp Gly Pro Val Leu Leu
                        660                 665                 670

Pro Asp Asn His Tyr Leu Ser Thr Gln Ser Ala Leu Ser Lys Asp Pro
                        675                 680                 685

Asn Glu Lys Arg Asp His Met Val Leu Leu Glu Phe Val Thr Ala Ala
                690                 695                 700

Gly Ile Thr Leu Gly Met Asp Glu Leu Tyr Lys Asn Gly Thr Glu Gly
        705                 710                 715                 720

Pro Asn Phe Tyr Val Pro Phe Ser Asn Ala Thr Gly Val Val
                        725                 730

<210> SEQ ID NO 34
<211> LENGTH: 267
<212> TYPE: PRT
<213> ORGANISM: Artificial Sequence
<220> FEATURE:
<223> OTHER INFORMATION: pro (wt) - mBDNF (wt) - T7 - His6

<400> SEQUENCE: 34

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
```

```
            20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
        50                  55                  60

His Val Ile Glu Glu Leu Leu Asp Glu Asp Gln Lys Val Arg Pro Asn
 65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
        130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
            195                 200                 205

Arg Thr Thr Gln Ser Tyr Val Arg Ala Leu Thr Met Asp Ser Lys Lys
        210                 215                 220

Arg Ile Gly Trp Arg Phe Ile Arg Ile Asp Thr Ser Cys Val Cys Thr
225                 230                 235                 240

Leu Thr Ile Lys Arg Gly Arg Gly Ser Gly Met Ala Ser Met Thr Gly
                245                 250                 255

Gly Gln Gln Met Gly His His His His His His
            260                 265

<210> SEQ ID NO 35
<211> LENGTH: 264
<212> TYPE: PRT
<213> ORGANISM: Artificial Sequence
<220> FEATURE:
<223> OTHER INFORMATION: pro (wt) - mBDNF (deltaRGR) (wt) - T7 - His6

<400> SEQUENCE: 35

Met Thr Ile Leu Phe Leu Thr Met Val Ile Ser Tyr Phe Gly Cys Met
 1               5                  10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
        50                  55                  60

His Val Ile Glu Glu Leu Leu Asp Glu Asp Gln Lys Val Arg Pro Asn
 65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
```

```
            115                 120                 125
His Ser Asp Pro Ala Arg Arg Gly Glu Leu Ser Val Cys Asp Ser Ile
        130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 36
<211> LENGTH: 283
<212> TYPE: PRT
<213> ORGANISM: Artificial Sequence
<220> FEATURE:
<223> OTHER INFORMATION: proBDNF (deltaRGR)-GSG-2N-GSG-T7-His6 (opsin-S)

<400> SEQUENCE: 36

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
```

```
                210               215                 220
Arg Ile Gly Trp Arg Phe Ile Arg Ile Asp Thr Ser Cys Val Cys Thr
225                 230                 235                 240

Leu Thr Ile Lys Gly Ser Gly Asn Gly Thr Glu Gly Pro Asn Phe Tyr
                245                 250                 255

Val Pro Phe Ser Asn Ala Thr Gly Ser Gly Met Ala Ser Met Thr Gly
                260                 265                 270

Gly Gln Gln Met Gly His His His His His
            275                 280

<210> SEQ ID NO 37
<211> LENGTH: 272
<212> TYPE: PRT
<213> ORGANISM: Artificial Sequence
<220> FEATURE:
<223> OTHER INFORMATION: proBDNF (deltaRGR)-GSG-2N-GSG-His6 (opsin-S)

<400> SEQUENCE: 37

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Ser Gly Asn Gly Thr Glu Gly Pro Asn Phe Tyr
                245                 250                 255

Val Pro Phe Ser Asn Ala Thr Gly Ser Gly His His His His His
                260                 265                 270

<210> SEQ ID NO 38
<211> LENGTH: 273
<212> TYPE: PRT
```

<213> ORGANISM: Artificial Sequence
<220> FEATURE:
<223> OTHER INFORMATION: proBDNF (deltaRGR)-GSG-2N-GSG-His6 (opsin-L

<400> SEQUENCE: 38

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
210                 215                 220

Arg Ile Gly Trp Arg Phe Ile Arg Ile Asp Thr Ser Cys Val Cys Thr
225                 230                 235                 240

Leu Thr Ile Lys Gly Ser Gly Asn Gly Thr Glu Gly Pro Asn Phe Tyr
                245                 250                 255

Val Pro Phe Ser Asn Ala Thr Gly Val Val Arg His His His His His
            260                 265                 270

His
```

<210> SEQ ID NO 39
<211> LENGTH: 265
<212> TYPE: PRT
<213> ORGANISM: Artificial Sequence
<220> FEATURE:
<223> OTHER INFORMATION: proBDNF - GSG - 2NIT - His6

<400> SEQUENCE: 39

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
```

```
              50                  55                  60
His Val Ile Glu Glu Leu Leu Asp Glu Asp Gln Lys Val Arg Pro Asn
 65                  70                  75                  80

Glu Glu Asn Asn Lys Asp Ala Asp Leu Tyr Thr Ser Arg Val Met Leu
                 85                  90                  95

Ser Ser Gln Val Pro Leu Glu Pro Pro Leu Leu Phe Leu Leu Glu Glu
                100                 105                 110

Tyr Lys Asn Tyr Leu Asp Ala Ala Asn Met Ser Met Arg Val Arg Arg
                115                 120                 125

His Ser Asp Pro Ala Arg Arg Gly Glu Leu Ser Val Cys Asp Ser Ile
                130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
                180                 185                 190

Lys Glu Gly Cys Arg Gly Ile Asp Lys Arg His Trp Asn Ser Gln Cys
                195                 200                 205

Arg Thr Thr Gln Ser Tyr Val Arg Ala Leu Thr Met Asp Ser Lys Lys
                210                 215                 220

Arg Ile Gly Trp Arg Phe Ile Arg Ile Asp Thr Ser Cys Val Cys Thr
225                 230                 235                 240

Leu Thr Ile Lys Gly Ser Gly Ala Asn Ile Thr Val Asn Ile Thr Val
                245                 250                 255

Gly Ser Gly His His His His His His
                260                 265

<210> SEQ ID NO 40
<211> LENGTH: 262
<212> TYPE: PRT
<213> ORGANISM: Artificial Sequence
<220> FEATURE:
<223> OTHER INFORMATION: proBDNF - GSG - NGT - His6

<400> SEQUENCE: 40

Met Thr Ile Leu Phe Leu Thr Met Val Ile Ser Tyr Phe Gly Cys Met
  1               5                  10                  15

Lys Ala Ala Pro Met Lys Glu Ala Asn Ile Arg Gly Gln Gly Gly Leu
                 20                  25                  30

Ala Tyr Pro Gly Val Arg Thr His Gly Thr Leu Glu Ser Val Asn Gly
                 35                  40                  45

Pro Lys Ala Gly Ser Arg Gly Leu Thr Ser Leu Ala Asp Thr Phe Glu
                 50                  55                  60

His Val Ile Glu Glu Leu Leu Asp Glu Asp Gln Lys Val Arg Pro Asn
 65                  70                  75                  80

Glu Glu Asn Asn Lys Asp Ala Asp Leu Tyr Thr Ser Arg Val Met Leu
                 85                  90                  95

Ser Ser Gln Val Pro Leu Glu Pro Pro Leu Leu Phe Leu Leu Glu Glu
                100                 105                 110

Tyr Lys Asn Tyr Leu Asp Ala Ala Asn Met Ser Met Arg Val Arg Arg
                115                 120                 125

His Ser Asp Pro Ala Arg Arg Gly Glu Leu Ser Val Cys Asp Ser Ile
                130                 135                 140

Ser Glu Trp Val Thr Ala Ala Asp Lys Lys Thr Ala Val Asp Met Ser
```

```
145                 150                 155                 160
Gly Gly Thr Val Thr Val Leu Glu Lys Val Pro Val Ser Lys Gly Gln
                165                 170                 175
Leu Lys Gln Tyr Phe Tyr Glu Thr Lys Cys Asn Pro Met Gly Tyr Thr
                180                 185                 190
Lys Glu Gly Cys Arg Gly Ile Asp Lys Arg His Trp Asn Ser Gln Cys
                195                 200                 205
Arg Thr Thr Gln Ser Tyr Val Arg Ala Leu Thr Met Asp Ser Lys Lys
                210                 215                 220
Arg Ile Gly Trp Arg Phe Ile Arg Ile Asp Thr Ser Cys Val Cys Thr
225                 230                 235                 240
Leu Thr Ile Lys Gly Ser Gly Ala Ala Ala Asn Gly Thr Gly Gly Ala
                245                 250                 255
His His His His His His
                260

<210> SEQ ID NO 41
<211> LENGTH: 265
<212> TYPE: PRT
<213> ORGANISM: Artificial Sequence
<220> FEATURE:
<223> OTHER INFORMATION: proBDNF - GSG - 2NAT - His6

<400> SEQUENCE: 41

Met Thr Ile Leu Phe Leu Thr Met Val Ile Ser Tyr Phe Gly Cys Met
1               5                   10                  15
Lys Ala Ala Pro Met Lys Glu Ala Asn Ile Arg Gly Gln Gly Gly Leu
                20                  25                  30
Ala Tyr Pro Gly Val Arg Thr His Gly Thr Leu Glu Ser Val Asn Gly
                35                  40                  45
Pro Lys Ala Gly Ser Arg Gly Leu Thr Ser Leu Ala Asp Thr Phe Glu
                50                  55                  60
His Val Ile Glu Glu Leu Leu Asp Glu Asp Gln Lys Val Arg Pro Asn
65                  70                  75                  80
Glu Glu Asn Asn Lys Asp Ala Asp Leu Tyr Thr Ser Arg Val Met Leu
                85                  90                  95
Ser Ser Gln Val Pro Leu Glu Pro Pro Leu Leu Phe Leu Leu Glu Glu
                100                 105                 110
Tyr Lys Asn Tyr Leu Asp Ala Ala Asn Met Ser Met Arg Val Arg Arg
                115                 120                 125
His Ser Asp Pro Ala Arg Arg Gly Glu Leu Ser Val Cys Asp Ser Ile
                130                 135                 140
Ser Glu Trp Val Thr Ala Ala Asp Lys Lys Thr Ala Val Asp Met Ser
145                 150                 155                 160
Gly Gly Thr Val Thr Val Leu Glu Lys Val Pro Val Ser Lys Gly Gln
                165                 170                 175
Leu Lys Gln Tyr Phe Tyr Glu Thr Lys Cys Asn Pro Met Gly Tyr Thr
                180                 185                 190
Lys Glu Gly Cys Arg Gly Ile Asp Lys Arg His Trp Asn Ser Gln Cys
                195                 200                 205
Arg Thr Thr Gln Ser Tyr Val Arg Ala Leu Thr Met Asp Ser Lys Lys
                210                 215                 220
Arg Ile Gly Trp Arg Phe Ile Arg Ile Asp Thr Ser Cys Val Cys Thr
225                 230                 235                 240
Leu Thr Ile Lys Gly Ser Gly Asn Ala Thr Gly Ala Asp Asn Gly Thr
```

245                 250                 255
Gly Ala Ser His His His His His
            260                 265

<210> SEQ ID NO 42
<211> LENGTH: 264
<212> TYPE: PRT
<213> ORGANISM: Artificial Sequence
<220> FEATURE:
<223> OTHER INFORMATION: Pre-pro-BDNF(-RGR; M61T)-T7-His6

<400> SEQUENCE: 42

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Thr Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 43
<211> LENGTH: 258
<212> TYPE: PRT
<213> ORGANISM: Artificial Sequence
<220> FEATURE:
<223> OTHER INFORMATION: pro(BDNF) - IgA-Site - mBDNF - GSG - His6

<400> SEQUENCE: 43

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
        50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
        115                 120                 125

Ala Pro Pro Ala Pro His Ser Asp Pro Ala Arg Arg Gly Glu Leu Ser
        130                 135                 140

Val Cys Asp Ser Ile Ser Glu Trp Val Thr Ala Ala Asp Lys Lys Thr
145                 150                 155                 160

Ala Val Asp Met Ser Gly Gly Thr Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
        195                 200                 205

Trp Asn Ser Gln Cys Arg Thr Thr Gln Ser Tyr Val Arg Ala Leu Thr
210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly His His His His
                245                 250                 255

His His

<210> SEQ ID NO 44
<211> LENGTH: 253
<212> TYPE: PRT
<213> ORGANISM: Artificial Sequence
<220> FEATURE:
<223> OTHER INFORMATION: pro(BDNF) R54A -mBDNF - GSG - His6

<400> SEQUENCE: 44

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Ala Gly Leu Thr Ser Leu Ala Asp Thr Phe Glu
        50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg

```
            115                 120                 125
His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Ser Gly His His His His His His
                245                 250

<210> SEQ ID NO 45
<211> LENGTH: 263
<212> TYPE: PRT
<213> ORGANISM: Artificial Sequence
<220> FEATURE:
<223> OTHER INFORMATION: His6 - pro(BDNF) R54A - IgA-Site - mBDNF

<400> SEQUENCE: 45

Met Thr Ile Leu Phe Leu Thr Met Val Ile Ser Tyr Phe Gly Cys Met
1               5                   10                  15

Lys Ala Ala Pro Met Lys Glu Ala Asn Ile His His His His His His
            20                  25                  30

Ala Pro Met Lys Glu Ala Asn Ile Arg Gly Gln Gly Gly Leu Ala Tyr
        35                  40                  45

Pro Gly Val Arg Thr His Gly Thr Leu Glu Ser Val Asn Gly Pro Lys
    50                  55                  60

Ala Gly Ser Ala Gly Leu Thr Ser Leu Ala Asp Thr Phe Glu His Val
65                  70                  75                  80

Ile Glu Glu Leu Leu Asp Glu Asp Gln Lys Val Arg Pro Asn Glu Glu
                85                  90                  95

Asn Asn Lys Asp Ala Asp Leu Tyr Thr Ser Arg Val Met Leu Ser Ser
            100                 105                 110

Gln Val Pro Leu Glu Pro Pro Leu Leu Phe Leu Leu Glu Glu Tyr Lys
        115                 120                 125

Asn Tyr Leu Asp Ala Ala Asn Met Ser Met Gly Ser Val Val Ala Pro
    130                 135                 140

Pro Ala Pro His Ser Asp Pro Ala Arg Arg Gly Glu Leu Ser Val Cys
145                 150                 155                 160

Asp Ser Ile Ser Glu Trp Val Thr Ala Ala Asp Lys Lys Thr Ala Val
                165                 170                 175

Asp Met Ser Gly Gly Thr Val Thr Val Leu Glu Lys Val Pro Val Ser
            180                 185                 190

Lys Gly Gln Leu Lys Gln Tyr Phe Tyr Glu Thr Lys Cys Asn Pro Met
        195                 200                 205

Gly Tyr Thr Lys Glu Gly Cys Arg Gly Ile Asp Lys Arg His Trp Asn
    210                 215                 220

Ser Gln Cys Arg Thr Thr Gln Ser Tyr Val Arg Ala Leu Thr Met Asp
```

```
225                 230                 235                 240

Ser Lys Lys Arg Ile Gly Trp Arg Phe Ile Arg Ile Asp Thr Ser Cys
                245                 250                 255

Val Cys Thr Leu Thr Ile Lys
            260

<210> SEQ ID NO 46
<211> LENGTH: 258
<212> TYPE: PRT
<213> ORGANISM: Artificial Sequence
<220> FEATURE:
<223> OTHER INFORMATION: His6 - pro(BDNF) R54A - mBDNF

<400> SEQUENCE: 46

Met Thr Ile Leu Phe Leu Thr Met Val Ile Ser Tyr Phe Gly Cys Met
1               5                   10                  15

Lys Ala Ala Pro Met Lys Glu Ala Asn Ile His His His His His His
                20                  25                  30

Ala Pro Met Lys Glu Ala Asn Ile Arg Gly Gln Gly Gly Leu Ala Tyr
            35                  40                  45

Pro Gly Val Arg Thr His Gly Thr Leu Glu Ser Val Asn Gly Pro Lys
50                  55                  60

Ala Gly Ser Ala Gly Leu Thr Ser Leu Ala Asp Thr Phe Glu His Val
65                  70                  75                  80

Ile Glu Glu Leu Leu Asp Glu Asp Gln Lys Val Arg Pro Asn Glu Glu
                85                  90                  95

Asn Asn Lys Asp Ala Asp Leu Tyr Thr Ser Arg Val Met Leu Ser Ser
            100                 105                 110

Gln Val Pro Leu Glu Pro Pro Leu Leu Phe Leu Leu Glu Glu Tyr Lys
        115                 120                 125

Asn Tyr Leu Asp Ala Ala Asn Met Ser Met Arg Val Arg Arg His Ser
130                 135                 140

Asp Pro Ala Arg Arg Gly Glu Leu Ser Val Cys Asp Ser Ile Ser Glu
145                 150                 155                 160

Trp Val Thr Ala Ala Asp Lys Lys Thr Ala Val Asp Met Ser Gly Gly
                165                 170                 175

Thr Val Thr Val Leu Glu Lys Val Pro Val Ser Lys Gly Gln Leu Lys
            180                 185                 190

Gln Tyr Phe Tyr Glu Thr Lys Cys Asn Pro Met Gly Tyr Thr Lys Glu
        195                 200                 205

Gly Cys Arg Gly Ile Asp Lys Arg His Trp Asn Ser Gln Cys Arg Thr
210                 215                 220

Thr Gln Ser Tyr Val Arg Ala Leu Thr Met Asp Ser Lys Lys Arg Ile
225                 230                 235                 240

Gly Trp Arg Phe Ile Arg Ile Asp Thr Ser Cys Val Cys Thr Leu Thr
                245                 250                 255

Ile Lys

<210> SEQ ID NO 47
<211> LENGTH: 264
<212> TYPE: PRT
<213> ORGANISM: Artificial Sequence
<220> FEATURE:
<223> OTHER INFORMATION: ProBDNF P60E, K65D, K73D, K95A - GSG - T7 -
      His6

<400> SEQUENCE: 47
```

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Glu Met Gly Tyr Thr
            180                 185                 190

Asp Glu Gly Cys Arg Gly Ile Asp Asp Arg His Trp Asn Ser Gln Cys
        195                 200                 205

Arg Thr Thr Gln Ser Tyr Val Arg Ala Leu Thr Met Asp Ser Ala Lys
    210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260
```

<210> SEQ ID NO 48
<211> LENGTH: 264
<212> TYPE: PRT
<213> ORGANISM: Artificial Sequence
<220> FEATURE:
<223> OTHER INFORMATION: ProBDNF K65D, K73D, K95A, R97A - GSG - T7 - His6

<400> SEQUENCE: 48

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95
```

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Asp Glu Gly Cys Arg Gly Ile Asp Asp Arg His Trp Asn Ser Gln Cys
            195                 200                 205

Arg Thr Thr Gln Ser Tyr Val Arg Ala Leu Thr Met Asp Ser Ala Lys
        210                 215                 220

Ala Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 49
<211> LENGTH: 266
<212> TYPE: PRT
<213> ORGANISM: Artificial Sequence
<220> FEATURE:
<223> OTHER INFORMATION: ProBDNF - GSG - myc - His6

<400> SEQUENCE: 49

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

```
Lys Glu Gly Cys Arg Gly Ile Asp Lys Arg His Trp Asn Ser Gln Cys
            195                 200                 205

Arg Thr Thr Gln Ser Tyr Val Arg Ala Leu Thr Met Asp Ser Lys Lys
        210                 215                 220

Arg Ile Gly Trp Arg Phe Ile Arg Ile Asp Thr Ser Cys Val Cys Thr
225                 230                 235                 240

Leu Thr Ile Lys Gly Ser Gly Glu Gln Lys Leu Ile Ser Glu Glu Asp
            245                 250                 255

Leu Gly Ser Gly His His His His His His
            260                 265

<210> SEQ ID NO 50
<211> LENGTH: 278
<212> TYPE: PRT
<213> ORGANISM: Artificial Sequence
<220> FEATURE:
<223> OTHER INFORMATION: pre-pro(IgA)-BDNF(-RGR; R81N)-opsin(L)

<400> SEQUENCE: 50

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
        115                 120                 125

Ala Pro Pro Ala Pro His Ser Asp Pro Ala Arg Arg Gly Glu Leu Ser
    130                 135                 140

Val Cys Asp Ser Ile Ser Glu Trp Val Thr Ala Ala Asp Lys Lys Thr
145                 150                 155                 160

Ala Val Asp Met Ser Gly Gly Thr Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
        195                 200                 205

Trp Asn Ser Gln Cys Asn Thr Thr Gln Ser Tyr Val Arg Ala Leu Thr
    210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Asn Gly Thr Glu
                245                 250                 255

Gly Pro Asn Phe Tyr Val Pro Phe Ser Asn Ala Thr Gly Val Val Arg
            260                 265                 270

His His His His His His
            275
```

<210> SEQ ID NO 51
<211> LENGTH: 294
<212> TYPE: PRT
<213> ORGANISM: Artificial Sequence
<220> FEATURE:
<223> OTHER INFORMATION: pre-pro(IgA)-BDNF(-RGR; R81N)-opsin(L)-myc-His6

<400> SEQUENCE: 51

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
        115                 120                 125

Ala Pro Pro Ala Pro His Ser Asp Pro Ala Arg Arg Gly Glu Leu Ser
    130                 135                 140

Val Cys Asp Ser Ile Ser Glu Trp Val Thr Ala Ala Asp Lys Lys Thr
145                 150                 155                 160

Ala Val Asp Met Ser Gly Gly Thr Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
        195                 200                 205

Trp Asn Ser Gln Cys Asn Thr Thr Gln Ser Tyr Val Arg Ala Leu Thr
    210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Asn Gly Thr Glu
                245                 250                 255

Gly Pro Asn Phe Tyr Val Pro Phe Ser Asn Ala Thr Gly Val Val Arg
            260                 265                 270

Gly Ser Gly Glu Gln Lys Leu Ile Ser Glu Glu Asp Leu Gly Ser Gly
        275                 280                 285

His His His His His His
    290
```

<210> SEQ ID NO 52
<211> LENGTH: 268
<212> TYPE: PRT
<213> ORGANISM: Artificial Sequence
<220> FEATURE:
<223> OTHER INFORMATION: pre-pro(IgA)-BDNF(-RGR; R81N)-myc-His6

<400> SEQUENCE: 52

Met Thr Ile Leu Phe Leu Thr Met Val Ile Ser Tyr Phe Gly Cys Met

```
1               5                   10                  15
Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
                35                  40                  45

Pro Lys Ala Gly Ser Arg Gly Leu Thr Ser Leu Ala Asp Thr Phe Glu
                50                  55                  60

His Val Ile Glu Glu Leu Leu Asp Glu Asp Gln Lys Val Arg Pro Asn
 65                  70                  75                  80

Glu Glu Asn Asn Lys Asp Ala Asp Leu Tyr Thr Ser Arg Val Met Leu
                    85                  90                  95

Ser Ser Gln Val Pro Leu Glu Pro Pro Leu Leu Phe Leu Leu Glu Glu
                100                 105                 110

Tyr Lys Asn Tyr Leu Asp Ala Ala Asn Met Ser Met Gly Ser Val Val
                115                 120                 125

Ala Pro Pro Ala Pro His Ser Asp Pro Ala Arg Arg Gly Glu Leu Ser
130                 135                 140

Val Cys Asp Ser Ile Ser Glu Trp Val Thr Ala Ala Asp Lys Lys Thr
145                 150                 155                 160

Ala Val Asp Met Ser Gly Gly Thr Val Thr Val Leu Glu Lys Val Pro
                165                 170                 175

Val Ser Lys Gly Gln Leu Lys Gln Tyr Phe Tyr Glu Thr Lys Cys Asn
                180                 185                 190

Pro Met Gly Tyr Thr Lys Glu Gly Cys Arg Gly Ile Asp Lys Arg His
                195                 200                 205

Trp Asn Ser Gln Cys Asn Thr Thr Gln Ser Tyr Val Arg Ala Leu Thr
210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Glu Gln Lys Leu
                245                 250                 255

Ile Ser Glu Glu Asp Leu His His His His His His
                260                 265
```

<210> SEQ ID NO 53
<211> LENGTH: 258
<212> TYPE: PRT
<213> ORGANISM: Artificial Sequence
<220> FEATURE:
<223> OTHER INFORMATION: pre-pro(IgA)-BDNF(-RGR; R81N)-His6

<400> SEQUENCE: 53

```
Met Thr Ile Leu Phe Leu Thr Met Val Ile Ser Tyr Phe Gly Cys Met
 1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
                35                  40                  45

Pro Lys Ala Gly Ser Arg Gly Leu Thr Ser Leu Ala Asp Thr Phe Glu
                50                  55                  60

His Val Ile Glu Glu Leu Leu Asp Glu Asp Gln Lys Val Arg Pro Asn
 65                  70                  75                  80

Glu Glu Asn Asn Lys Asp Ala Asp Leu Tyr Thr Ser Arg Val Met Leu
                    85                  90                  95

Ser Ser Gln Val Pro Leu Glu Pro Pro Leu Leu Phe Leu Leu Glu Glu
```

```
                    100                 105                 110
Tyr Lys Asn Tyr Leu Asp Ala Ala Asn Met Ser Met Gly Ser Val Val
            115                 120                 125

Ala Pro Pro Ala Pro His Ser Asp Pro Ala Arg Arg Gly Glu Leu Ser
        130                 135                 140

Val Cys Asp Ser Ile Ser Glu Trp Val Thr Ala Ala Asp Lys Lys Thr
145                 150                 155                 160

Ala Val Asp Met Ser Gly Gly Thr Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
        195                 200                 205

Trp Asn Ser Gln Cys Asn Thr Thr Gln Ser Tyr Val Arg Ala Leu Thr
    210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly His His His His
                245                 250                 255

His His

<210> SEQ ID NO 54
<211> LENGTH: 278
<212> TYPE: PRT
<213> ORGANISM: Artificial Sequence
<220> FEATURE:
<223> OTHER INFORMATION: pre-pro(IgA)-BDNF(-RGR)-opsin(L)-His6

<400> SEQUENCE: 54

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
            115                 120                 125

Ala Pro Pro Ala Pro His Ser Asp Pro Ala Arg Arg Gly Glu Leu Ser
        130                 135                 140

Val Cys Asp Ser Ile Ser Glu Trp Val Thr Ala Ala Asp Lys Lys Thr
145                 150                 155                 160

Ala Val Asp Met Ser Gly Gly Thr Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
        195                 200                 205
```

```
Trp Asn Ser Gln Cys Arg Thr Thr Gln Ser Tyr Val Arg Ala Leu Thr
        210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Asn Gly Thr Glu
                245                 250                 255

Gly Pro Asn Phe Tyr Val Pro Phe Ser Asn Ala Thr Gly Val Val Arg
            260                 265                 270

His His His His His His
        275

<210> SEQ ID NO 55
<211> LENGTH: 278
<212> TYPE: PRT
<213> ORGANISM: Artificial Sequence
<220> FEATURE:
<223> OTHER INFORMATION: pre-pro(IgA)-BDNF(-RGR; K25N)-opsin(L)-His6

<400> SEQUENCE: 55

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
        115                 120                 125

Ala Pro Pro Ala Pro His Ser Asp Pro Ala Arg Arg Gly Glu Leu Ser
    130                 135                 140

Val Cys Asp Ser Ile Ser Glu Trp Val Thr Ala Ala Asp Asn Lys Thr
145                 150                 155                 160

Ala Val Asp Met Ser Gly Gly Thr Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
        195                 200                 205

Trp Asn Ser Gln Cys Arg Thr Thr Gln Ser Tyr Val Arg Ala Leu Thr
    210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Asn Gly Thr Glu
                245                 250                 255

Gly Pro Asn Phe Tyr Val Pro Phe Ser Asn Ala Thr Gly Val Val Arg
            260                 265                 270

His His His His His His
        275
```

```
<210> SEQ ID NO 56
<211> LENGTH: 278
<212> TYPE: PRT
<213> ORGANISM: Artificial Sequence
<220> FEATURE:
<223> OTHER INFORMATION: pre-pro(IgA)-BDNF(-RGR; T35N)-opsin(L)-His6

<400> SEQUENCE: 56
```

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
        115                 120                 125

Ala Pro Pro Ala Pro His Ser Asp Pro Ala Arg Arg Gly Glu Leu Ser
    130                 135                 140

Val Cys Asp Ser Ile Ser Glu Trp Val Thr Ala Ala Asp Lys Lys Thr
145                 150                 155                 160

Ala Val Asp Met Ser Gly Gly Asn Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
        195                 200                 205

Trp Asn Ser Gln Cys Arg Thr Thr Gln Ser Tyr Val Arg Ala Leu Thr
    210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Asn Gly Thr Glu
                245                 250                 255

Gly Pro Asn Phe Tyr Val Pro Phe Ser Asn Ala Thr Gly Val Val Arg
            260                 265                 270

His His His His His His
        275

```
<210> SEQ ID NO 57
<211> LENGTH: 278
<212> TYPE: PRT
<213> ORGANISM: Artificial Sequence
<220> FEATURE:
<223> OTHER INFORMATION: pre-pro(IgA)-BDNF(-RGR; K25N,
     T35N)-opsin(L)-His6

<400> SEQUENCE: 57
```

Met Thr Ile Leu Phe Leu Thr Met Val Ile Ser Tyr Phe Gly Cys Met
1               5                   10                  15

```
Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
50                  55                  60

His Val Ile Glu Glu Leu Leu Asp Glu Asp Gln Lys Val Arg Pro Asn
 65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
                100                 105                 110

Tyr Lys Asn Tyr Leu Asp Ala Ala Asn Met Ser Met Gly Ser Val Val
            115                 120                 125

Ala Pro Pro Ala Pro His Ser Asp Pro Ala Arg Arg Gly Glu Leu Ser
130                 135                 140

Val Cys Asp Ser Ile Ser Glu Trp Val Thr Ala Ala Asp Asn Lys Thr
145                 150                 155                 160

Ala Val Asp Met Ser Gly Gly Asn Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
        195                 200                 205

Trp Asn Ser Gln Cys Arg Thr Thr Gln Ser Tyr Val Arg Ala Leu Thr
210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Asn Gly Thr Glu
                245                 250                 255

Gly Pro Asn Phe Tyr Val Pro Phe Ser Asn Ala Thr Gly Val Val Arg
            260                 265                 270

His His His His His His
        275

<210> SEQ ID NO 58
<211> LENGTH: 269
<212> TYPE: PRT
<213> ORGANISM: Artificial Sequence
<220> FEATURE:
<223> OTHER INFORMATION: pre-pro(IgA)-BDNF(-RGR; K25N, T35N,
      R81N)-T7-His6

<400> SEQUENCE: 58

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
50                  55                  60

His Val Ile Glu Glu Leu Leu Asp Glu Asp Gln Lys Val Arg Pro Asn
 65                  70                  75                  80

Glu Glu Asn Asn Lys Asp Ala Asp Leu Tyr Thr Ser Arg Val Met Leu
                85                  90                  95
```

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
            115                 120                 125

Ala Pro Pro Ala Pro His Ser Asp Pro Ala Arg Arg Gly Glu Leu Ser
        130                 135                 140

Val Cys Asp Ser Ile Ser Glu Trp Val Thr Ala Ala Asp Asn Lys Thr
145                 150                 155                 160

Ala Val Asp Met Ser Gly Gly Asn Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
        195                 200                 205

Trp Asn Ser Gln Cys Asn Thr Thr Gln Ser Tyr Val Arg Ala Leu Thr
            210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Met Ala Ser Met
                245                 250                 255

Thr Gly Gly Gln Gln Met Gly His His His His His His
            260                 265

<210> SEQ ID NO 59
<211> LENGTH: 269
<212> TYPE: PRT
<213> ORGANISM: Artificial Sequence
<220> FEATURE:
<223> OTHER INFORMATION: pre-pro(IgA)-BDNF(-RGR; K25N, T35N, Q79T,
      R81N)-T7-His6

<400> SEQUENCE: 59

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
            115                 120                 125

Ala Pro Pro Ala Pro His Ser Asp Pro Ala Arg Arg Gly Glu Leu Ser
        130                 135                 140

Val Cys Asp Ser Ile Ser Glu Trp Val Thr Ala Ala Asp Asn Lys Thr
145                 150                 155                 160

Ala Val Asp Met Ser Gly Gly Asn Val Thr Val Leu Glu Lys Val Pro
                165                 170                 175

Val Ser Lys Gly Gln Leu Lys Gln Tyr Phe Tyr Glu Thr Lys Cys Asn

```
                    180                 185                 190
Pro Met Gly Tyr Thr Lys Glu Gly Cys Arg Gly Ile Asp Lys Arg His
                195                 200                 205

Trp Asn Ser Thr Cys Asn Thr Thr Gln Ser Tyr Val Arg Ala Leu Thr
            210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Met Ala Ser Met
                245                 250                 255

Thr Gly Gly Gln Gln Met Gly His His His His His His
                260                 265

<210> SEQ ID NO 60
<211> LENGTH: 278
<212> TYPE: PRT
<213> ORGANISM: Artificial Sequence
<220> FEATURE:
<223> OTHER INFORMATION: pre-pro(IgA)-BDNF(-RGR; G62N,
      Y63G)-opsin(L)-His6

<400> SEQUENCE: 60

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
        115                 120                 125

Ala Pro Pro Ala Pro His Ser Asp Pro Ala Arg Arg Gly Glu Leu Ser
    130                 135                 140

Val Cys Asp Ser Ile Ser Glu Trp Val Thr Ala Ala Asp Lys Lys Thr
145                 150                 155                 160

Ala Val Asp Met Ser Gly Gly Thr Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Asn Gly Thr Lys Glu Gly Cys Arg Gly Ile Asp Lys Arg His
        195                 200                 205

Trp Asn Ser Gln Cys Arg Thr Thr Gln Ser Tyr Val Arg Ala Leu Thr
    210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Asn Gly Thr Glu
                245                 250                 255

Gly Pro Asn Phe Tyr Val Pro Phe Ser Asn Ala Thr Gly Val Val Arg
            260                 265                 270
```

His His His His His His
        275

<210> SEQ ID NO 61
<211> LENGTH: 278
<212> TYPE: PRT
<213> ORGANISM: Artificial Sequence
<220> FEATURE:
<223> OTHER INFORMATION: pre-pro(IgA)-BDNF(-RGR; G62N, Y63G, K25N,
      T35N)-opsin(L)-His6

<400> SEQUENCE: 61

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
        115                 120                 125

Ala Pro Pro Ala Pro His Ser Asp Pro Ala Arg Arg Gly Glu Leu Ser
    130                 135                 140

Val Cys Asp Ser Ile Ser Glu Trp Val Thr Ala Ala Asp Asn Lys Thr
145                 150                 155                 160

Ala Val Asp Met Ser Gly Gly Asn Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Asn Gly Thr Lys Glu Gly Cys Arg Gly Ile Asp Lys Arg His
        195                 200                 205

Trp Asn Ser Gln Cys Arg Thr Thr Gln Ser Tyr Val Arg Ala Leu Thr
    210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Asn Gly Thr Glu
                245                 250                 255

Gly Pro Asn Phe Tyr Val Pro Phe Ser Asn Ala Thr Gly Val Val Arg
            260                 265                 270

His His His His His His
        275

<210> SEQ ID NO 62
<211> LENGTH: 264
<212> TYPE: PRT
<213> ORGANISM: Artificial Sequence
<220> FEATURE:
<223> OTHER INFORMATION: pre-pro-BDNF(-RGR; G62N, Y63G, Q79T)-T7-His6

<400> SEQUENCE: 62

Met Thr Ile Leu Phe Leu Thr Met Val Ile Ser Tyr Phe Gly Cys Met

```
1               5                   10                  15
Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
                35                  40                  45

Pro Lys Ala Gly Ser Arg Gly Leu Thr Ser Leu Ala Asp Thr Phe Glu
                50                  55                  60

His Val Ile Glu Glu Leu Leu Asp Glu Asp Gln Lys Val Arg Pro Asn
 65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
                100                 105                 110

Tyr Lys Asn Tyr Leu Asp Ala Ala Asn Met Ser Met Arg Val Arg Arg
                115                 120                 125

His Ser Asp Pro Ala Arg Arg Gly Glu Leu Ser Val Cys Asp Ser Ile
                130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Asn Gly Thr
                180                 185                 190

Lys Glu Gly Cys Arg Gly Ile Asp Lys Arg His Trp Asn Ser Thr Cys
                195                 200                 205

Arg Thr Thr Gln Ser Tyr Val Arg Ala Leu Thr Met Asp Ser Lys Lys
                210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
                260

<210> SEQ ID NO 63
<211> LENGTH: 264
<212> TYPE: PRT
<213> ORGANISM: Artificial Sequence
<220> FEATURE:
<223> OTHER INFORMATION: pre-pro-BDNF(-RGR; T35N, Q79T)-T7-His6

<400> SEQUENCE: 63

Met Thr Ile Leu Phe Leu Thr Met Val Ile Ser Tyr Phe Gly Cys Met
 1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
                35                  40                  45

Pro Lys Ala Gly Ser Arg Gly Leu Thr Ser Leu Ala Asp Thr Phe Glu
                50                  55                  60

His Val Ile Glu Glu Leu Leu Asp Glu Asp Gln Lys Val Arg Pro Asn
 65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
```

```
                    100                 105                 110
Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
        130                 135                 140

Ser Glu Trp Val Thr Ala Ala Asp Lys Lys Thr Ala Val Asp Met Ser
145                 150                 155                 160

Gly Gly Asn Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Thr Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 64
<211> LENGTH: 264
<212> TYPE: PRT
<213> ORGANISM: Artificial Sequence
<220> FEATURE:
<223> OTHER INFORMATION: pre-pro-BDNF(-RGR; K25N, Q79T)-T7-His6

<400> SEQUENCE: 64

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Asn Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Thr Cys
```

195                 200                 205
Arg Thr Thr Gln Ser Tyr Val Arg Ala Leu Thr Met Asp Ser Lys Lys
210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 65
<211> LENGTH: 264
<212> TYPE: PRT
<213> ORGANISM: Artificial Sequence
<220> FEATURE:
<223> OTHER INFORMATION: pre-pro-BDNF(-RGR; T35N, G62N, Y63G,
      Q79T)-T7-His6

<400> SEQUENCE: 65

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
130                 135                 140

Ser Glu Trp Val Thr Ala Ala Asp Lys Lys Thr Ala Val Asp Met Ser
145                 150                 155                 160

Gly Gly Asn Val Thr Val Leu Glu Lys Val Pro Val Ser Lys Gly Gln
                165                 170                 175

Leu Lys Gln Tyr Phe Tyr Glu Thr Lys Cys Asn Pro Met Asn Gly Thr
            180                 185                 190

Lys Glu Gly Cys Arg Gly Ile Asp Lys Arg His Trp Asn Ser Thr Cys
        195                 200                 205

Arg Thr Thr Gln Ser Tyr Val Arg Ala Leu Thr Met Asp Ser Lys Lys
210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 66
<211> LENGTH: 264

-continued

```
<212> TYPE: PRT
<213> ORGANISM: Artificial Sequence
<220> FEATURE:
<223> OTHER INFORMATION: pre-pro-BDNF(-RGR; T35N; G62N; Y63G)-T7-His6

<400> SEQUENCE: 66

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Asn Val Thr Val Leu Glu Lys Val Pro Val Ser Lys Gly Gln
                165                 170                 175

Leu Lys Gln Tyr Phe Tyr Glu Thr Lys Cys Asn Pro Met Asn Gly Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 67
<211> LENGTH: 264
<212> TYPE: PRT
<213> ORGANISM: Artificial Sequence
<220> FEATURE:
<223> OTHER INFORMATION: pre-pro-BDNF(-RGR; K25N; G62N; Y63G)-T7-His6

<400> SEQUENCE: 67

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60
```

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Asn Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Asn Gly Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 68
<211> LENGTH: 264
<212> TYPE: PRT
<213> ORGANISM: Artificial Sequence
<220> FEATURE:
<223> OTHER INFORMATION: pre-pro-BDNF(-RGR; K25N; T35N)-T7-His6

<400> SEQUENCE: 68

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Asn Lys Thr Ala Val Asp Met Ser
145                 150                 155                 160

```
Gly Gly Asn Val Thr Val Leu Glu Lys Val Pro Val Ser Lys Gly Gln
            165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
            195                 200                 205

Arg Thr Thr Gln Ser Tyr Val Arg Ala Leu Thr Met Asp Ser Lys Lys
210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
            245                 250                 255

Met Gly His His His His His His
            260

<210> SEQ ID NO 69
<211> LENGTH: 264
<212> TYPE: PRT
<213> ORGANISM: Artificial Sequence
<220> FEATURE:
<223> OTHER INFORMATION: pre-pro-BDNF(-RGR; G62N, Y63G, R81N)-T7-His6

<400> SEQUENCE: 69

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
            130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
            165                 170                 175

Leu Lys Gln Tyr Phe Tyr Glu Thr Lys Cys Asn Pro Met Asn Gly Thr
            180                 185                 190

Lys Glu Gly Cys Arg Gly Ile Asp Lys Arg His Trp Asn Ser Gln Cys
            195                 200                 205

Asn Thr Thr Gln Ser Tyr Val Arg Ala Leu Thr Met Asp Ser Lys Lys
            210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
            245                 250                 255
```

Met Gly His His His His His His
            260

<210> SEQ ID NO 70
<211> LENGTH: 264
<212> TYPE: PRT
<213> ORGANISM: Artificial Sequence
<220> FEATURE:
<223> OTHER INFORMATION: pre-pro-BDNF(-RGR; K25N; T35N; Q79T)-T7-His6

<400> SEQUENCE: 70

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Asn Lys Thr Ala Val Asp Met Ser
145                 150                 155                 160

Gly Gly Asn Val Thr Val Leu Glu Lys Val Pro Val Ser Lys Gly Gln
                165                 170                 175

Leu Lys Gln Tyr Phe Tyr Glu Thr Lys Cys Asn Pro Met Asn Gly Thr
            180                 185                 190

Lys Glu Gly Cys Arg Gly Ile Asp Lys Arg His Trp Asn Ser Thr Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 71
<211> LENGTH: 480
<212> TYPE: PRT
<213> ORGANISM: Artificial Sequence
<220> FEATURE:
<223> OTHER INFORMATION: pre-pro-BDNF(-RGD)_(G4S)2GG_VL<IGF-1R>-Ck-His6

<400> SEQUENCE: 71

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu

-continued

```
                20                  25                  30
Ala Tyr Pro Gly Val Arg Thr His Gly Thr Leu Glu Ser Val Asn Gly
             35                  40                  45

Pro Lys Ala Gly Ser Arg Gly Leu Thr Ser Leu Ala Asp Thr Phe Glu
         50                  55                  60

His Val Ile Glu Glu Leu Leu Asp Glu Asp Gln Lys Val Arg Pro Asn
 65                  70                  75                  80

Glu Glu Asn Asn Lys Asp Ala Asp Leu Tyr Thr Ser Arg Val Met Leu
                 85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
            130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
            165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
            195                 200                 205

Arg Thr Thr Gln Ser Tyr Val Arg Ala Leu Thr Met Asp Ser Lys Lys
            210                 215                 220

Arg Ile Gly Trp Arg Phe Ile Arg Ile Asp Thr Ser Cys Val Cys Thr
225                 230                 235                 240

Leu Thr Ile Lys Gly Gly Gly Ser Gly Gly Gly Ser Gly Gly
            245                 250                 255

Glu Ile Val Leu Thr Gln Ser Pro Ala Thr Leu Ser Leu Ser Pro Gly
            260                 265                 270

Glu Arg Ala Thr Leu Ser Cys Arg Ala Ser Gln Ser Val Ser Ser Tyr
            275                 280                 285

Leu Ala Trp Tyr Gln Gln Lys Pro Gly Gln Ala Pro Arg Leu Leu Ile
            290                 295                 300

Tyr Asp Ala Ser Lys Arg Ala Thr Gly Ile Pro Ala Arg Phe Ser Gly
305                 310                 315                 320

Ser Gly Ser Gly Thr Asp Phe Thr Leu Thr Ile Ser Ser Leu Glu Pro
            325                 330                 335

Glu Asp Phe Ala Val Tyr Tyr Cys Gln Gln Arg Ser Lys Trp Pro Pro
            340                 345                 350

Trp Thr Phe Gly Gln Gly Thr Lys Val Glu Ser Lys Arg Thr Val Ala
            355                 360                 365

Ala Pro Ser Val Phe Ile Phe Pro Pro Ser Asp Glu Gln Leu Lys Ser
            370                 375                 380

Gly Thr Ala Ser Val Val Cys Leu Leu Asn Asn Phe Tyr Pro Arg Glu
385                 390                 395                 400

Ala Lys Val Gln Trp Lys Val Asp Asn Ala Leu Gln Ser Gly Asn Ser
            405                 410                 415

Gln Glu Ser Val Thr Glu Gln Asp Ser Lys Asp Ser Thr Tyr Ser Leu
            420                 425                 430

Ser Ser Thr Leu Thr Leu Ser Lys Ala Asp Tyr Glu Lys His Lys Val
            435                 440                 445
```

-continued

Tyr Ala Cys Glu Val Thr His Gln Gly Leu Ser Ser Pro Val Thr Lys
450                 455                 460

Ser Phe Asn Arg Gly Glu Cys Gly Ser Gly His His His His His His
465                 470                 475                 480

<210> SEQ ID NO 72
<211> LENGTH: 490
<212> TYPE: PRT
<213> ORGANISM: Artificial Sequence
<220> FEATURE:
<223> OTHER INFORMATION: pre-pro-BDNF(-RGD)_(G4S)4GG_VL<IGF-1R>-Ck-His6

<400> SEQUENCE: 72

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Gly Gly Gly Ser Gly Gly Gly Ser Gly Gly
                245                 250                 255

Gly Gly Ser Gly Gly Gly Ser Gly Gly Glu Ile Val Leu Thr Gln
            260                 265                 270

Ser Pro Ala Thr Leu Ser Leu Ser Pro Gly Glu Arg Ala Thr Leu Ser
    275                 280                 285

Cys Arg Ala Ser Gln Ser Val Ser Ser Tyr Leu Ala Trp Tyr Gln Gln
290                 295                 300

Lys Pro Gly Gln Ala Pro Arg Leu Leu Ile Tyr Asp Ala Ser Lys Arg
305                 310                 315                 320

Ala Thr Gly Ile Pro Ala Arg Phe Ser Gly Ser Gly Ser Gly Thr Asp
                325                 330                 335

```
Phe Thr Leu Thr Ile Ser Ser Leu Glu Pro Glu Asp Phe Ala Val Tyr
                340                 345                 350

Tyr Cys Gln Gln Arg Ser Lys Trp Pro Pro Trp Thr Phe Gly Gln Gly
            355                 360                 365

Thr Lys Val Glu Ser Lys Arg Thr Val Ala Ala Pro Ser Val Phe Ile
        370                 375                 380

Phe Pro Pro Ser Asp Glu Gln Leu Lys Ser Gly Thr Ala Ser Val Val
385                 390                 395                 400

Cys Leu Leu Asn Asn Phe Tyr Pro Arg Glu Ala Lys Val Gln Trp Lys
                405                 410                 415

Val Asp Asn Ala Leu Gln Ser Gly Asn Ser Gln Glu Ser Val Thr Glu
            420                 425                 430

Gln Asp Ser Lys Asp Ser Thr Tyr Ser Leu Ser Ser Thr Leu Thr Leu
        435                 440                 445

Ser Lys Ala Asp Tyr Glu Lys His Lys Val Tyr Ala Cys Glu Val Thr
    450                 455                 460

His Gln Gly Leu Ser Ser Pro Val Thr Lys Ser Phe Asn Arg Gly Glu
465                 470                 475                 480

Cys Gly Ser Gly His His His His His
                485                 490

<210> SEQ ID NO 73
<211> LENGTH: 500
<212> TYPE: PRT
<213> ORGANISM: Artificial Sequence
<220> FEATURE:
<223> OTHER INFORMATION: pre-pro-BDNF(-RGD)_(G4S)6GG_VL<IGF-1R>-Ck-His6

<400> SEQUENCE: 73

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205
```

```
Arg Thr Thr Gln Ser Tyr Val Arg Ala Leu Thr Met Asp Ser Lys Lys
        210                 215                 220

Arg Ile Gly Trp Arg Phe Ile Arg Ile Asp Thr Ser Cys Val Cys Thr
225                 230                 235                 240

Leu Thr Ile Lys Gly Gly Gly Ser Gly Gly Gly Gly Ser Gly Gly
                245                 250                 255

Gly Gly Ser Gly Gly Gly Ser Gly Gly Gly Ser Gly Gly Gly
                260                 265                 270

Gly Ser Gly Gly Glu Ile Val Leu Thr Gln Ser Pro Ala Thr Leu Ser
            275                 280                 285

Leu Ser Pro Gly Glu Arg Ala Thr Leu Ser Cys Arg Ala Ser Gln Ser
290                 295                 300

Val Ser Ser Tyr Leu Ala Trp Tyr Gln Gln Lys Pro Gly Gln Ala Pro
305                 310                 315                 320

Arg Leu Leu Ile Tyr Asp Ala Ser Lys Arg Ala Thr Gly Ile Pro Ala
                325                 330                 335

Arg Phe Ser Gly Ser Gly Ser Gly Thr Asp Phe Thr Leu Thr Ile Ser
                340                 345                 350

Ser Leu Glu Pro Glu Asp Phe Ala Val Tyr Tyr Cys Gln Gln Arg Ser
            355                 360                 365

Lys Trp Pro Pro Trp Thr Phe Gly Gln Gly Thr Lys Val Glu Ser Lys
370                 375                 380

Arg Thr Val Ala Ala Pro Ser Val Phe Ile Phe Pro Pro Ser Asp Glu
385                 390                 395                 400

Gln Leu Lys Ser Gly Thr Ala Ser Val Val Cys Leu Leu Asn Asn Phe
                405                 410                 415

Tyr Pro Arg Glu Ala Lys Val Gln Trp Lys Val Asp Asn Ala Leu Gln
                420                 425                 430

Ser Gly Asn Ser Gln Glu Ser Val Thr Glu Gln Asp Ser Lys Asp Ser
            435                 440                 445

Thr Tyr Ser Leu Ser Ser Thr Leu Thr Leu Ser Lys Ala Asp Tyr Glu
    450                 455                 460

Lys His Lys Val Tyr Ala Cys Glu Val Thr His Gln Gly Leu Ser Ser
465                 470                 475                 480

Pro Val Thr Lys Ser Phe Asn Arg Gly Glu Cys Gly Ser Gly His His
                485                 490                 495

His His His His
        500

<210> SEQ ID NO 74
<211> LENGTH: 481
<212> TYPE: PRT
<213> ORGANISM: Artificial Sequence
<220> FEATURE:
<223> OTHER INFORMATION: pre-pro-BDNF(-RGD)_(G4S)2GG_VH<IGF-1R>-CH1-His6

<400> SEQUENCE: 74

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60
```

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Gly Gly Ser Gly Gly Gly Ser Gly Gly
                245                 250                 255

Gln Val Glu Leu Val Glu Ser Gly Gly Val Val Gln Pro Gly Arg
            260                 265                 270

Ser Gln Arg Leu Ser Cys Ala Ala Ser Gly Phe Thr Phe Ser Ser Tyr
    275                 280                 285

Gly Met His Trp Val Arg Gln Ala Pro Gly Lys Gly Leu Glu Trp Val
    290                 295                 300

Ala Ile Ile Trp Phe Asp Gly Ser Ser Thr Tyr Tyr Ala Asp Ser Val
305                 310                 315                 320

Arg Gly Arg Phe Thr Ile Ser Arg Asp Asn Ser Lys Asn Thr Leu Tyr
                325                 330                 335

Leu Gln Met Asn Ser Leu Arg Ala Glu Asp Thr Ala Val Tyr Phe Cys
            340                 345                 350

Ala Arg Glu Leu Gly Arg Arg Tyr Phe Asp Leu Trp Gly Arg Gly Thr
        355                 360                 365

Leu Val Ser Val Ser Ser Ala Ser Thr Lys Gly Pro Ser Val Phe Pro
    370                 375                 380

Leu Ala Pro Ser Ser Lys Ser Thr Ser Gly Gly Thr Ala Ala Leu Gly
385                 390                 395                 400

Cys Leu Val Lys Asp Tyr Phe Pro Glu Pro Val Thr Val Ser Trp Asn
                405                 410                 415

Ser Gly Ala Leu Thr Ser Gly Val His Thr Phe Pro Ala Val Leu Gln
            420                 425                 430

Ser Ser Gly Leu Tyr Ser Leu Ser Ser Val Val Thr Val Pro Ser Ser
        435                 440                 445

Ser Leu Gly Thr Gln Thr Tyr Ile Cys Asn Val Asn His Lys Pro Ser
    450                 455                 460

Asn Thr Lys Val Asp Lys Lys Val Gly Ser Gly His His His His
465                 470                 475                 480

His

<210> SEQ ID NO 75
<211> LENGTH: 491
<212> TYPE: PRT
<213> ORGANISM: Artificial Sequence
<220> FEATURE:
<223> OTHER INFORMATION: pre-pro-BDNF(-RGD)_(G4S)4GG_VH<IGF-1R>-CH1-His6

<400> SEQUENCE: 75

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Gly Gly Gly Ser Gly Gly Gly Gly Ser Gly Gly
                245                 250                 255

Gly Gly Ser Gly Gly Gly Gly Ser Gly Gly Gln Val Glu Leu Val Glu
            260                 265                 270

Ser Gly Gly Gly Val Val Gln Pro Gly Arg Ser Gln Arg Leu Ser Cys
        275                 280                 285

Ala Ala Ser Gly Phe Thr Phe Ser Ser Tyr Gly Met His Trp Val Arg
    290                 295                 300

Gln Ala Pro Gly Lys Gly Leu Glu Trp Val Ala Ile Ile Trp Phe Asp
305                 310                 315                 320

Gly Ser Ser Thr Tyr Tyr Ala Asp Ser Val Arg Gly Arg Phe Thr Ile
                325                 330                 335

Ser Arg Asp Asn Ser Lys Asn Thr Leu Tyr Leu Gln Met Asn Ser Leu
            340                 345                 350

Arg Ala Glu Asp Thr Ala Val Tyr Phe Cys Ala Arg Glu Leu Gly Arg
```

```
            355                 360                 365
Arg Tyr Phe Asp Leu Trp Gly Arg Gly Thr Leu Val Ser Val Ser Ser
    370                 375                 380

Ala Ser Thr Lys Gly Pro Ser Val Phe Pro Leu Ala Pro Ser Ser Lys
385                 390                 395                 400

Ser Thr Ser Gly Gly Thr Ala Ala Leu Gly Cys Leu Val Lys Asp Tyr
                405                 410                 415

Phe Pro Glu Pro Val Thr Val Ser Trp Asn Ser Gly Ala Leu Thr Ser
            420                 425                 430

Gly Val His Thr Phe Pro Ala Val Leu Gln Ser Ser Gly Leu Tyr Ser
                435                 440                 445

Leu Ser Ser Val Val Thr Val Pro Ser Ser Ser Leu Gly Thr Gln Thr
    450                 455                 460

Tyr Ile Cys Asn Val Asn His Lys Pro Ser Asn Thr Lys Val Asp Lys
465                 470                 475                 480

Lys Val Gly Ser Gly His His His His His His
                485                 490

<210> SEQ ID NO 76
<211> LENGTH: 501
<212> TYPE: PRT
<213> ORGANISM: Artificial Sequence
<220> FEATURE:
<223> OTHER INFORMATION: pre-pro-BDNF(-RGD)_(G4S)6GG_VH<IGF-1R>-CH1-His6

<400> SEQUENCE: 76

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
```

-continued

```
                225                 230                 235                 240
Leu Thr Ile Lys Gly Gly Gly Ser Gly Gly Gly Ser Gly Gly
                245                 250                 255

Gly Gly Ser Gly Gly Gly Ser Gly Gly Gly Ser Gly Gly Gly
                260                 265                 270

Gly Ser Gly Gly Gln Val Glu Leu Val Glu Ser Gly Gly Val Val
                275                 280                 285

Gln Pro Gly Arg Ser Gln Arg Leu Ser Cys Ala Ala Ser Gly Phe Thr
        290                 295                 300

Phe Ser Ser Tyr Gly Met His Trp Val Arg Gln Ala Pro Gly Lys Gly
305                 310                 315                 320

Leu Glu Trp Val Ala Ile Ile Trp Phe Asp Gly Ser Ser Thr Tyr Tyr
                325                 330                 335

Ala Asp Ser Val Arg Gly Arg Phe Thr Ile Ser Arg Asp Asn Ser Lys
                340                 345                 350

Asn Thr Leu Tyr Leu Gln Met Asn Ser Leu Arg Ala Glu Asp Thr Ala
                355                 360                 365

Val Tyr Phe Cys Ala Arg Glu Leu Gly Arg Arg Tyr Phe Asp Leu Trp
                370                 375                 380

Gly Arg Gly Thr Leu Val Ser Val Ser Ser Ala Ser Thr Lys Gly Pro
385                 390                 395                 400

Ser Val Phe Pro Leu Ala Pro Ser Ser Lys Ser Thr Ser Gly Gly Thr
                405                 410                 415

Ala Ala Leu Gly Cys Leu Val Lys Asp Tyr Phe Pro Glu Pro Val Thr
                420                 425                 430

Val Ser Trp Asn Ser Gly Ala Leu Thr Ser Gly Val His Thr Phe Pro
                435                 440                 445

Ala Val Leu Gln Ser Ser Gly Leu Tyr Ser Leu Ser Ser Val Val Thr
                450                 455                 460

Val Pro Ser Ser Ser Leu Gly Thr Gln Thr Tyr Ile Cys Asn Val Asn
465                 470                 475                 480

His Lys Pro Ser Asn Thr Lys Val Asp Lys Lys Val Gly Ser Gly His
                485                 490                 495

His His His His His
        500

<210> SEQ ID NO 77
<211> LENGTH: 493
<212> TYPE: PRT
<213> ORGANISM: Artificial Sequence
<220> FEATURE:
<223> OTHER INFORMATION: pre-pro-BDNF-(G3D)4-G3S-VH<IGF-1R>-CH1

<400> SEQUENCE: 77

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
        50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
```

```
            85                  90                  95
Ser Ser Gln Val Pro Leu Glu Pro Pro Leu Phe Leu Leu Glu Glu
                100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
        130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Gly Asp Gly Gly Asp Gly Gly Asp
                245                 250                 255

Gly Gly Gly Asp Gly Gly Asp Gly Gly Ser Gln Val Glu Leu
        260                 265                 270

Val Glu Ser Gly Gly Gly Val Val Gln Pro Gly Arg Ser Gln Arg Leu
    275                 280                 285

Ser Cys Ala Ala Ser Gly Phe Thr Phe Ser Ser Tyr Gly Met His Trp
290                 295                 300

Val Arg Gln Ala Pro Gly Lys Gly Leu Glu Trp Val Ala Ile Ile Trp
305                 310                 315                 320

Phe Asp Gly Ser Ser Thr Tyr Tyr Ala Asp Ser Val Arg Gly Arg Phe
                325                 330                 335

Thr Ile Ser Arg Asp Asn Ser Lys Asn Thr Leu Tyr Leu Gln Met Asn
            340                 345                 350

Ser Leu Arg Ala Glu Asp Thr Ala Val Tyr Phe Cys Ala Arg Glu Leu
        355                 360                 365

Gly Arg Arg Tyr Phe Asp Leu Trp Gly Arg Gly Thr Leu Val Ser Val
    370                 375                 380

Ser Ser Ala Ser Thr Lys Gly Pro Ser Val Phe Pro Leu Ala Pro Ser
385                 390                 395                 400

Ser Lys Ser Thr Ser Gly Gly Thr Ala Ala Leu Gly Cys Leu Val Lys
                405                 410                 415

Asp Tyr Phe Pro Glu Pro Val Thr Val Ser Trp Asn Ser Gly Ala Leu
            420                 425                 430

Thr Ser Gly Val His Thr Phe Pro Ala Val Leu Gln Ser Ser Gly Leu
        435                 440                 445

Tyr Ser Leu Ser Ser Val Val Thr Val Pro Ser Ser Ser Leu Gly Thr
    450                 455                 460

Gln Thr Tyr Ile Cys Asn Val Asn His Lys Pro Ser Asn Thr Lys Val
465                 470                 475                 480

Asp Lys Lys Val Gly Ser Gly His His His His His His
                485                 490

<210> SEQ ID NO 78
```

<211> LENGTH: 513
<212> TYPE: PRT
<213> ORGANISM: Artificial Sequence
<220> FEATURE:
<223> OTHER INFORMATION:
pre-pro-BDNF-(G4S)3-VL<IGF-1R>-(G4S)4-VH<IGF-1R>-His6

<400> SEQUENCE: 78

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Gly Gly Ser Gly Gly Gly Ser Gly Gly
                245                 250                 255

Gly Gly Ser Glu Ile Val Leu Thr Gln Ser Pro Ala Thr Leu Ser Leu
            260                 265                 270

Ser Pro Gly Glu Arg Ala Thr Leu Ser Cys Arg Ala Ser Gln Ser Val
        275                 280                 285

Ser Ser Tyr Leu Ala Trp Tyr Gln Gln Lys Pro Gly Gln Ala Pro Arg
    290                 295                 300

Leu Leu Ile Tyr Asp Ala Ser Lys Arg Ala Thr Gly Ile Pro Ala Arg
305                 310                 315                 320

Phe Ser Gly Ser Gly Ser Gly Thr Asp Phe Thr Leu Thr Ile Ser Ser
                325                 330                 335

Leu Glu Pro Glu Asp Phe Ala Val Tyr Tyr Cys Gln Gln Arg Ser Lys
            340                 345                 350

Trp Pro Pro Trp Thr Phe Gly Gln Gly Thr Lys Val Glu Ser Lys Gly
        355                 360                 365

Gly Gly Gly Ser Gly Gly Gly Gly Ser Gly Gly Gly Gly Ser Gly Gly
```

```
                370             375             380
Gly Gly Ser Gly Gly Gln Val Glu Leu Val Glu Ser Gly Gly Val
385                 390             395             400

Val Gln Pro Gly Arg Ser Gln Arg Leu Ser Cys Ala Ala Ser Gly Phe
            405             410             415

Thr Phe Ser Ser Tyr Gly Met His Trp Val Arg Gln Ala Pro Gly Lys
        420             425             430

Gly Leu Glu Trp Val Ala Ile Ile Trp Phe Asp Gly Ser Ser Thr Tyr
    435             440             445

Tyr Ala Asp Ser Val Arg Gly Arg Phe Thr Ile Ser Arg Asp Asn Ser
450             455             460

Lys Asn Thr Leu Tyr Leu Gln Met Asn Ser Leu Arg Ala Glu Asp Thr
465             470             475             480

Ala Val Tyr Phe Cys Ala Arg Glu Leu Gly Arg Arg Tyr Phe Asp Leu
            485             490             495

Trp Gly Arg Gly Thr Leu Val Ser Val Ser Ser His His His His His
            500             505             510

His
```

```
<210> SEQ ID NO 79
<211> LENGTH: 517
<212> TYPE: PRT
<213> ORGANISM: Artificial Sequence
<220> FEATURE:
<223> OTHER INFORMATION: pro(BDNF) - IgA-Site - mBDNF - GSG - 2N -
      (G3D)4 - G3S - VH (8D3) - CH1 - GSG - His6

<400> SEQUENCE: 79

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
        115                 120                 125

Ala Pro Pro Ala Pro His Ser Asp Pro Ala Arg Arg Gly Glu Leu Ser
130                 135                 140

Val Cys Asp Ser Ile Ser Glu Trp Val Thr Ala Ala Asp Lys Lys Thr
145                 150                 155                 160

Ala Val Asp Met Ser Gly Gly Thr Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
        195                 200                 205

Trp Asn Ser Gln Cys Arg Thr Thr Gln Ser Tyr Val Arg Ala Leu Thr
```

```
                210                 215                 220
Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Asn Gly Thr Glu
                245                 250                 255

Gly Pro Asn Phe Tyr Val Pro Phe Ser Asn Ala Thr Gly Val Val Arg
                260                 265                 270

Gly Gly Gly Asp Gly Gly Gly Asp Gly Gly Gly Asp Gly Gly Gly Asp
            275                 280                 285

Gly Gly Gly Ser Glu Val Gln Leu Val Glu Ser Gly Gly Gly Leu Val
        290                 295                 300

Gln Pro Gly Asn Ser Leu Thr Leu Ser Cys Val Ala Ser Gly Phe Thr
305                 310                 315                 320

Phe Ser Asn Tyr Gly Met His Trp Ile Arg Gln Ala Pro Lys Lys Gly
                325                 330                 335

Leu Glu Trp Ile Ala Met Ile Tyr Tyr Asp Ser Ser Lys Met Asn Tyr
                340                 345                 350

Ala Asp Thr Val Lys Gly Arg Phe Thr Ile Ser Arg Asp Asn Ser Lys
            355                 360                 365

Asn Thr Leu Tyr Leu Glu Met Asn Ser Leu Arg Ser Glu Asp Thr Ala
370                 375                 380

Met Tyr Tyr Cys Ala Val Pro Thr Ser His Tyr Val Val Asp Val Trp
385                 390                 395                 400

Gly Gln Gly Val Ser Val Thr Val Ser Ser Ala Ser Thr Lys Gly Pro
                405                 410                 415

Ser Val Phe Pro Leu Ala Pro Ser Ser Lys Ser Thr Ser Gly Gly Thr
                420                 425                 430

Ala Ala Leu Gly Cys Leu Val Lys Asp Tyr Phe Pro Glu Pro Val Thr
            435                 440                 445

Val Ser Trp Asn Ser Gly Ala Leu Thr Ser Gly Val His Thr Phe Pro
        450                 455                 460

Ala Val Leu Gln Ser Ser Gly Leu Tyr Ser Leu Ser Ser Val Val Thr
465                 470                 475                 480

Val Pro Ser Ser Ser Leu Gly Thr Gln Thr Tyr Ile Cys Asn Val Asn
                485                 490                 495

His Lys Pro Ser Asn Thr Lys Val Asp Lys Lys Val Gly Ser Gly His
                500                 505                 510

His His His His His
        515

<210> SEQ ID NO 80
<211> LENGTH: 233
<212> TYPE: PRT
<213> ORGANISM: Artificial Sequence
<220> FEATURE:
<223> OTHER INFORMATION: VL_8D3_chim. Ab rat-anti-murTfR VL _ hum const.

<400> SEQUENCE: 80

Met Gly Trp Ser Cys Ile Ile Leu Phe Leu Val Ala Thr Ala Thr Gly
1               5                   10                  15

Val His Ser Asp Ile Gln Met Thr Gln Ser Pro Ala Ser Leu Ser Ala
                20                  25                  30

Ser Leu Glu Glu Ile Val Thr Ile Thr Cys Gln Ala Ser Gln Asp Ile
            35                  40                  45

Gly Asn Trp Leu Ala Trp Tyr Gln Gln Lys Pro Gly Lys Ser Pro Gln
```

Leu Leu Ile Tyr Gly Ala Thr Ser Leu Ala Asp Gly Val Pro Ser Arg
65                  70                  75                  80

Phe Ser Gly Ser Arg Ser Gly Thr Gln Phe Ser Leu Lys Ile Ser Arg
                85                  90                  95

Val Gln Val Glu Asp Ile Gly Ile Tyr Tyr Cys Leu Gln Ala Tyr Asn
            100                 105                 110

Thr Pro Trp Thr Phe Gly Gly Gly Thr Lys Leu Glu Leu Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 81
<211> LENGTH: 517
<212> TYPE: PRT
<213> ORGANISM: Artificial Sequence
<220> FEATURE:
<223> OTHER INFORMATION: pre-pro(IgA)-BDNF(-RGR;
    R81N)_opsin(L)-(G3D)4-G3S_VH<TfR>8D3-CH1-His6

<400> SEQUENCE: 81

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
        115                 120                 125

Ala Pro Pro Ala Pro His Ser Asp Pro Ala Arg Arg Gly Glu Leu Ser
130                 135                 140

Val Cys Asp Ser Ile Ser Glu Trp Val Thr Ala Ala Asp Lys Lys Thr
145                 150                 155                 160

Ala Val Asp Met Ser Gly Gly Thr Val Thr Val Leu Glu Lys Val Pro
                165                 170                 175

```
Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
            195                 200                 205

Trp Asn Ser Gln Cys Asn Thr Thr Gln Ser Tyr Val Arg Ala Leu Thr
            210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Asn Gly Thr Glu
            245                 250                 255

Gly Pro Asn Phe Tyr Val Pro Phe Ser Asn Ala Thr Gly Val Val Arg
            260                 265                 270

Gly Gly Gly Asp Gly Gly Gly Asp Gly Gly Gly Asp Gly Gly Gly Asp
            275                 280                 285

Gly Gly Gly Ser Glu Val Gln Leu Val Glu Ser Gly Gly Gly Leu Val
            290                 295                 300

Gln Pro Gly Asn Ser Leu Thr Leu Ser Cys Val Ala Ser Gly Phe Thr
305                 310                 315                 320

Phe Ser Asn Tyr Gly Met His Trp Ile Arg Gln Ala Pro Lys Lys Gly
            325                 330                 335

Leu Glu Trp Ile Ala Met Ile Tyr Tyr Asp Ser Ser Lys Met Asn Tyr
            340                 345                 350

Ala Asp Thr Val Lys Gly Arg Phe Thr Ile Ser Arg Asp Asn Ser Lys
            355                 360                 365

Asn Thr Leu Tyr Leu Glu Met Asn Ser Leu Arg Ser Glu Asp Thr Ala
            370                 375                 380

Met Tyr Tyr Cys Ala Val Pro Thr Ser His Tyr Val Val Asp Val Trp
385                 390                 395                 400

Gly Gln Gly Val Ser Val Thr Val Ser Ser Ala Ser Thr Lys Gly Pro
            405                 410                 415

Ser Val Phe Pro Leu Ala Pro Ser Ser Lys Ser Thr Ser Gly Gly Thr
            420                 425                 430

Ala Ala Leu Gly Cys Leu Val Lys Asp Tyr Phe Pro Glu Pro Val Thr
            435                 440                 445

Val Ser Trp Asn Ser Gly Ala Leu Thr Ser Gly Val His Thr Phe Pro
450                 455                 460

Ala Val Leu Gln Ser Ser Gly Leu Tyr Ser Leu Ser Ser Val Val Thr
465                 470                 475                 480

Val Pro Ser Ser Ser Leu Gly Thr Gln Thr Tyr Ile Cys Asn Val Asn
            485                 490                 495

His Lys Pro Ser Asn Thr Lys Val Asp Lys Lys Val Gly Ser Gly His
            500                 505                 510

His His His His His
        515

<210> SEQ ID NO 82
<211> LENGTH: 278
<212> TYPE: PRT
<213> ORGANISM: Artificial Sequence
<220> FEATURE:
<223> OTHER INFORMATION: pre-pro-BDNF-IgA-mBDNF(R81N)-GSG-2N-His6

<400> SEQUENCE: 82

Met Thr Ile Leu Phe Leu Thr Met Val Ile Ser Tyr Phe Gly Cys Met
1               5                   10                  15
```

-continued

```
Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
        50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
        115                 120                 125

Ala Pro Pro Ala Pro His Ser Asp Pro Ala Arg Arg Gly Glu Leu Ser
    130                 135                 140

Val Cys Asp Ser Ile Ser Glu Trp Val Thr Ala Ala Asp Lys Lys Thr
145                 150                 155                 160

Ala Val Asp Met Ser Gly Gly Thr Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
        195                 200                 205

Trp Asn Ser Gln Cys Asn Thr Thr Gln Ser Tyr Val Arg Ala Leu Thr
210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Asn Gly Thr Glu
                245                 250                 255

Gly Pro Asn Phe Tyr Val Pro Phe Ser Asn Ala Thr Gly Val Val Arg
            260                 265                 270

His His His His His His
        275
```

<210> SEQ ID NO 83
<211> LENGTH: 264
<212> TYPE: PRT
<213> ORGANISM: Artificial Sequence
<220> FEATURE:
<223> OTHER INFORMATION: proBDNF (deltaRGR)-GSG-T7-His6

<400> SEQUENCE: 83

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
        50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95
```

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
            130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                    165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
            195                 200                 205

Arg Thr Thr Gln Ser Tyr Val Arg Ala Leu Thr Met Asp Ser Lys Lys
            210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                    245                 250                 255

Met Gly His His His His His His
            260

<210> SEQ ID NO 84
<211> LENGTH: 494
<212> TYPE: PRT
<213> ORGANISM: Artificial Sequence
<220> FEATURE:
<223> OTHER INFORMATION:
      pre-pro(IgA)-BDNF(-RGR)_(G3D)4-G3S_VH<IGF-1R>-CH1-His6

<400> SEQUENCE: 84

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
            115                 120                 125

Ala Pro Pro Ala Pro His Ser Asp Pro Ala Arg Arg Gly Glu Leu Ser
            130                 135                 140

Val Cys Asp Ser Ile Ser Glu Trp Val Thr Ala Ala Asp Lys Lys Thr
145                 150                 155                 160

Ala Val Asp Met Ser Gly Gly Thr Val Thr Val Leu Glu Lys Val Pro
                    165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
        195                 200                 205

Trp Asn Ser Gln Cys Arg Thr Thr Gln Ser Tyr Val Arg Ala Leu Thr
    210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Gly Asp Gly Gly Gly
                245                 250                 255

Asp Gly Gly Gly Asp Gly Gly Gly Asp Gly Gly Ser Gln Val Glu
                260                 265                 270

Leu Val Glu Ser Gly Gly Gly Val Val Gln Pro Gly Arg Ser Gln Arg
            275                 280                 285

Leu Ser Cys Ala Ala Ser Gly Phe Thr Phe Ser Ser Tyr Gly Met His
            290                 295                 300

Trp Val Arg Gln Ala Pro Gly Lys Gly Leu Glu Trp Val Ala Ile Ile
305                 310                 315                 320

Trp Phe Asp Gly Ser Ser Thr Tyr Tyr Ala Asp Ser Val Arg Gly Arg
                325                 330                 335

Phe Thr Ile Ser Arg Asp Asn Ser Lys Asn Thr Leu Tyr Leu Gln Met
            340                 345                 350

Asn Ser Leu Arg Ala Glu Asp Thr Ala Val Tyr Phe Cys Ala Arg Glu
            355                 360                 365

Leu Gly Arg Arg Tyr Phe Asp Leu Trp Gly Arg Gly Thr Leu Val Ser
        370                 375                 380

Val Ser Ser Ala Ser Thr Lys Gly Pro Ser Val Phe Pro Leu Ala Pro
385                 390                 395                 400

Ser Ser Lys Ser Thr Ser Gly Gly Thr Ala Ala Leu Gly Cys Leu Val
                405                 410                 415

Lys Asp Tyr Phe Pro Glu Pro Val Thr Val Ser Trp Asn Ser Gly Ala
            420                 425                 430

Leu Thr Ser Gly Val His Thr Phe Pro Ala Val Leu Gln Ser Ser Gly
        435                 440                 445

Leu Tyr Ser Leu Ser Ser Val Val Thr Val Pro Ser Ser Ser Leu Gly
        450                 455                 460

Thr Gln Thr Tyr Ile Cys Asn Val Asn His Lys Pro Ser Asn Thr Lys
465                 470                 475                 480

Val Asp Lys Lys Val Gly Ser Gly His His His His His His
                485                 490

<210> SEQ ID NO 85
<211> LENGTH: 499
<212> TYPE: PRT
<213> ORGANISM: Artificial Sequence
<220> FEATURE:
<223> OTHER INFORMATION:
      pre-pro(IgA)-BDNF(-RGR)_(G3D)4-G3S_VH<IGF-1R>-CH1-EPKSC-His6

<400> SEQUENCE: 85

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu

```
                50              55              60
His Val Ile Glu Glu Leu Leu Asp Glu Asp Gln Lys Val Arg Pro Asn
 65                      70                      75              80
Glu Glu Asn Asn Lys Asp Ala Asp Leu Tyr Thr Ser Arg Val Met Leu
                         85                      90              95
Ser Ser Gln Val Pro Leu Glu Pro Pro Leu Leu Phe Leu Leu Glu Glu
                100                     105                     110
Tyr Lys Asn Tyr Leu Asp Ala Ala Asn Met Ser Met Gly Ser Val Val
            115                     120                     125
Ala Pro Pro Ala Pro His Ser Asp Pro Ala Arg Arg Gly Glu Leu Ser
        130                     135                     140
Val Cys Asp Ser Ile Ser Glu Trp Val Thr Ala Ala Asp Lys Lys Thr
145                     150                     155                     160
Ala Val Asp Met Ser Gly Gly Thr Val Thr Val Leu Glu Lys Val Pro
                    165                     170                     175
Val Ser Lys Gly Gln Leu Lys Gln Tyr Phe Tyr Glu Thr Lys Cys Asn
                180                     185                     190
Pro Met Gly Tyr Thr Lys Glu Gly Cys Arg Gly Ile Asp Lys Arg His
            195                     200                     205
Trp Asn Ser Gln Cys Arg Thr Thr Gln Ser Tyr Val Arg Ala Leu Thr
210                     215                     220
Met Asp Ser Lys Lys Arg Ile Gly Trp Arg Phe Ile Arg Ile Asp Thr
225                     230                     235                     240
Ser Cys Val Cys Thr Leu Thr Ile Lys Gly Gly Asp Gly Gly Gly Gly
                    245                     250                     255
Asp Gly Gly Gly Asp Gly Gly Gly Asp Gly Gly Ser Gln Val Glu
                260                     265                     270
Leu Val Glu Ser Gly Gly Val Val Gln Pro Gly Arg Ser Gln Arg
            275                     280                     285
Leu Ser Cys Ala Ala Ser Gly Phe Thr Phe Ser Ser Tyr Gly Met His
        290                     295                     300
Trp Val Arg Gln Ala Pro Gly Lys Gly Leu Glu Trp Val Ala Ile Ile
305                     310                     315                     320
Trp Phe Asp Gly Ser Ser Thr Tyr Tyr Ala Asp Ser Val Arg Gly Arg
                    325                     330                     335
Phe Thr Ile Ser Arg Asp Asn Ser Lys Asn Thr Leu Tyr Leu Gln Met
                340                     345                     350
Asn Ser Leu Arg Ala Glu Asp Thr Ala Val Tyr Phe Cys Ala Arg Glu
            355                     360                     365
Leu Gly Arg Arg Tyr Phe Asp Leu Trp Gly Arg Gly Thr Leu Val Ser
        370                     375                     380
Val Ser Ser Ala Ser Thr Lys Gly Pro Ser Val Phe Pro Leu Ala Pro
385                     390                     395                     400
Ser Ser Lys Ser Thr Ser Gly Gly Thr Ala Ala Leu Gly Cys Leu Val
                    405                     410                     415
Lys Asp Tyr Phe Pro Glu Pro Val Thr Val Ser Trp Asn Ser Gly Ala
                420                     425                     430
Leu Thr Ser Gly Val His Thr Phe Pro Ala Val Leu Gln Ser Ser Gly
            435                     440                     445
Leu Tyr Ser Leu Ser Ser Val Val Thr Val Pro Ser Ser Ser Leu Gly
        450                     455                     460
Thr Gln Thr Tyr Ile Cys Asn Val Asn His Lys Pro Ser Asn Thr Lys
465                     470                     475                     480
```

Val Asp Lys Lys Val Glu Pro Lys Ser Cys Gly Ser Gly His His His
            485             490             495

His His His

<210> SEQ ID NO 86
<211> LENGTH: 517
<212> TYPE: PRT
<213> ORGANISM: Artificial Sequence
<220> FEATURE:
<223> OTHER INFORMATION: pre-pro(IgA)-BDNF(-RGR;
    R81N)_opsin(L)-(G3D)4-G3S_VH<IGF-1R>-CH1-His6

<400> SEQUENCE: 86

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
        115                 120                 125

Ala Pro Pro Ala Pro His Ser Asp Pro Ala Arg Arg Gly Glu Leu Ser
    130                 135                 140

Val Cys Asp Ser Ile Ser Glu Trp Val Thr Ala Ala Asp Lys Lys Thr
145                 150                 155                 160

Ala Val Asp Met Ser Gly Gly Thr Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
        195                 200                 205

Trp Asn Ser Gln Cys Asn Thr Thr Gln Ser Tyr Val Arg Ala Leu Thr
    210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Asn Gly Thr Glu
                245                 250                 255

Gly Pro Asn Phe Tyr Val Pro Phe Ser Asn Ala Thr Gly Val Val Arg
            260                 265                 270

Gly Gly Gly Asp Gly Gly Gly Asp Gly Gly Gly Asp Gly Gly Gly Asp
        275                 280                 285

Gly Gly Gly Ser Gln Val Glu Leu Val Glu Ser Gly Gly Val Val
    290                 295                 300

Gln Pro Gly Arg Ser Gln Arg Leu Ser Cys Ala Ala Ser Gly Phe Thr
305                 310                 315                 320

Phe Ser Ser Tyr Gly Met His Trp Val Arg Gln Ala Pro Gly Lys Gly
                325                 330                 335

```
Leu Glu Trp Val Ala Ile Ile Trp Phe Asp Gly Ser Ser Thr Tyr Tyr
            340                 345                 350

Ala Asp Ser Val Arg Gly Arg Phe Thr Ile Ser Arg Asp Asn Ser Lys
            355                 360                 365

Asn Thr Leu Tyr Leu Gln Met Asn Ser Leu Arg Ala Glu Asp Thr Ala
        370                 375                 380

Val Tyr Phe Cys Ala Arg Glu Leu Gly Arg Arg Tyr Phe Asp Leu Trp
385                 390                 395                 400

Gly Arg Gly Thr Leu Val Ser Val Ser Ala Ser Thr Lys Gly Pro
                405                 410                 415

Ser Val Phe Pro Leu Ala Pro Ser Ser Lys Ser Thr Ser Gly Gly Thr
            420                 425                 430

Ala Ala Leu Gly Cys Leu Val Lys Asp Tyr Phe Pro Glu Pro Val Thr
        435                 440                 445

Val Ser Trp Asn Ser Gly Ala Leu Thr Ser Gly Val His Thr Phe Pro
    450                 455                 460

Ala Val Leu Gln Ser Ser Gly Leu Tyr Ser Leu Ser Ser Val Val Thr
465                 470                 475                 480

Val Pro Ser Ser Ser Leu Gly Thr Gln Thr Tyr Ile Cys Asn Val Asn
                485                 490                 495

His Lys Pro Ser Asn Thr Lys Val Asp Lys Lys Val Gly Ser Gly His
            500                 505                 510

His His His His His
        515

<210> SEQ ID NO 87
<211> LENGTH: 516
<212> TYPE: PRT
<213> ORGANISM: Artificial Sequence
<220> FEATURE:
<223> OTHER INFORMATION:
      pre-pro(IgA)-BDNF(-RGR; R81N)_opsin(L)-(G2D)5-G2SG
      _VH<IGF-1R>-CH1-His6

<400> SEQUENCE: 87

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
        115                 120                 125

Ala Pro Pro Ala Pro His Ser Asp Pro Ala Arg Arg Gly Glu Leu Ser
    130                 135                 140

Val Cys Asp Ser Ile Ser Glu Trp Val Thr Ala Ala Asp Lys Lys Thr
145                 150                 155                 160
```

Ala Val Asp Met Ser Gly Gly Thr Val Thr Val Leu Glu Lys Val Pro
              165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
            195                 200                 205

Trp Asn Ser Gln Cys Asn Thr Thr Gln Ser Tyr Val Arg Ala Leu Thr
    210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Ser Gly Asn Gly Thr Glu
                245                 250                 255

Gly Pro Asn Phe Tyr Val Pro Phe Ser Asn Ala Thr Gly Val Val Arg
            260                 265                 270

Gly Gly Asp Gly Gly Asp Gly Gly Asp Gly Gly Asp Gly Gly Asp Gly
            275                 280                 285

Gly Ser Gly Gln Val Glu Leu Val Glu Ser Gly Gly Val Val Gln
    290                 295                 300

Pro Gly Arg Ser Gln Arg Leu Ser Cys Ala Ala Ser Gly Phe Thr Phe
305                 310                 315                 320

Ser Ser Tyr Gly Met His Trp Val Arg Gln Ala Pro Gly Lys Gly Leu
                325                 330                 335

Glu Trp Val Ala Ile Ile Trp Phe Asp Gly Ser Ser Thr Tyr Tyr Ala
            340                 345                 350

Asp Ser Val Arg Gly Arg Phe Thr Ile Ser Arg Asp Asn Ser Lys Asn
            355                 360                 365

Thr Leu Tyr Leu Gln Met Asn Ser Leu Arg Ala Glu Asp Thr Ala Val
    370                 375                 380

Tyr Phe Cys Ala Arg Glu Leu Gly Arg Arg Tyr Phe Asp Leu Trp Gly
385                 390                 395                 400

Arg Gly Thr Leu Val Ser Val Ser Ser Ala Ser Thr Lys Gly Pro Ser
                405                 410                 415

Val Phe Pro Leu Ala Pro Ser Ser Lys Ser Thr Ser Gly Gly Thr Ala
            420                 425                 430

Ala Leu Gly Cys Leu Val Lys Asp Tyr Phe Pro Glu Pro Val Thr Val
            435                 440                 445

Ser Trp Asn Ser Gly Ala Leu Thr Ser Gly Val His Thr Phe Pro Ala
    450                 455                 460

Val Leu Gln Ser Ser Gly Leu Tyr Ser Leu Ser Ser Val Val Thr Val
465                 470                 475                 480

Pro Ser Ser Ser Leu Gly Thr Gln Thr Tyr Ile Cys Asn Val Asn His
                485                 490                 495

Lys Pro Ser Asn Thr Lys Val Asp Lys Lys Val Gly Ser Gly His His
            500                 505                 510

His His His His
        515

<210> SEQ ID NO 88
<211> LENGTH: 493
<212> TYPE: PRT
<213> ORGANISM: Artificial Sequence
<220> FEATURE:
<223> OTHER INFORMATION: pre-pro-BDNF-(G3D)4-G3S-VH<IGF-1R>-CH1

<400> SEQUENCE: 88

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
            130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
            165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
            195                 200                 205

Arg Thr Thr Gln Ser Tyr Val Arg Ala Leu Thr Met Asp Ser Lys Lys
            210                 215                 220

Arg Ile Gly Trp Arg Phe Ile Arg Ile Asp Thr Ser Cys Val Cys Thr
225                 230                 235                 240

Leu Thr Ile Lys Gly Gly Gly Asp Gly Gly Gly Asp Gly Gly Gly Asp
            245                 250                 255

Gly Gly Gly Asp Gly Gly Gly Asp Gly Gly Gly Ser Gln Val Glu Leu
            260                 265                 270

Val Glu Ser Gly Gly Gly Val Val Gln Pro Gly Arg Ser Gln Arg Leu
            275                 280                 285

Ser Cys Ala Ala Ser Gly Phe Thr Phe Ser Ser Tyr Gly Met His Trp
            290                 295                 300

Val Arg Gln Ala Pro Gly Lys Gly Leu Glu Trp Val Ala Ile Ile Trp
305                 310                 315                 320

Phe Asp Gly Ser Ser Thr Tyr Tyr Ala Asp Ser Val Arg Gly Arg Phe
            325                 330                 335

Thr Ile Ser Arg Asp Asn Ser Lys Asn Thr Leu Tyr Leu Gln Met Asn
            340                 345                 350

Ser Leu Arg Ala Glu Asp Thr Ala Val Tyr Phe Cys Ala Arg Glu Leu
            355                 360                 365

Gly Arg Arg Tyr Phe Asp Leu Trp Gly Arg Gly Thr Leu Val Ser Val
            370                 375                 380

Ser Ser Ala Ser Thr Lys Gly Pro Ser Val Phe Pro Leu Ala Pro Ser
385                 390                 395                 400

Ser Lys Ser Thr Ser Gly Gly Thr Ala Ala Leu Gly Cys Leu Val Lys
            405                 410                 415

Asp Tyr Phe Pro Glu Pro Val Thr Val Ser Trp Asn Ser Gly Ala Leu
```

```
                420             425             430
Thr Ser Gly Val His Thr Phe Pro Ala Val Leu Gln Ser Ser Gly Leu
            435                 440                 445
Tyr Ser Leu Ser Ser Val Val Thr Val Pro Ser Ser Ser Leu Gly Thr
            450                 455                 460
Gln Thr Tyr Ile Cys Asn Val Asn His Lys Pro Ser Asn Thr Lys Val
465                 470                 475                 480
Asp Lys Lys Val Gly Ser Gly His His His His His His
            485                 490

<210> SEQ ID NO 89
<211> LENGTH: 264
<212> TYPE: PRT
<213> ORGANISM: Artificial Sequence
<220> FEATURE:
<223> OTHER INFORMATION: Pre-pro-BDNF(-RGR; R81N)-T7-His6

<400> SEQUENCE: 89

Met Thr Ile Leu Phe Leu Thr Met Val Ile Ser Tyr Phe Gly Cys Met
1               5                   10                  15
Lys Ala Ala Pro Met Lys Glu Ala Asn Ile Arg Gly Gln Gly Gly Leu
            20                  25                  30
Ala Tyr Pro Gly Val Arg Thr His Gly Thr Leu Glu Ser Val Asn Gly
        35                  40                  45
Pro Lys Ala Gly Ser Arg Gly Leu Thr Ser Leu Ala Asp Thr Phe Glu
    50                  55                  60
His Val Ile Glu Glu Leu Leu Asp Glu Asp Gln Lys Val Arg Pro Asn
65                  70                  75                  80
Glu Glu Asn Asn Lys Asp Ala Asp Leu Tyr Thr Ser Arg Val Met Leu
                85                  90                  95
Ser Ser Gln Val Pro Leu Glu Pro Pro Leu Leu Phe Leu Leu Glu Glu
            100                 105                 110
Tyr Lys Asn Tyr Leu Asp Ala Ala Asn Met Ser Met Arg Val Arg Arg
        115                 120                 125
His Ser Asp Pro Ala Arg Arg Gly Glu Leu Ser Val Cys Asp Ser Ile
    130                 135                 140
Ser Glu Trp Val Thr Ala Ala Asp Lys Lys Thr Ala Val Asp Met Ser
145                 150                 155                 160
Gly Gly Thr Val Thr Val Leu Glu Lys Val Pro Val Ser Lys Gly Gln
                165                 170                 175
Leu Lys Gln Tyr Phe Tyr Glu Thr Lys Cys Asn Pro Met Gly Tyr Thr
            180                 185                 190
Lys Glu Gly Cys Arg Gly Ile Asp Lys Arg His Trp Asn Ser Gln Cys
        195                 200                 205
Asn Thr Thr Gln Ser Tyr Val Arg Ala Leu Thr Met Asp Ser Lys Lys
    210                 215                 220
Arg Ile Gly Trp Arg Phe Ile Arg Ile Asp Thr Ser Cys Val Cys Thr
225                 230                 235                 240
Leu Thr Ile Lys Gly Ser Gly Met Ala Ser Met Thr Gly Gly Gln Gln
                245                 250                 255
Met Gly His His His His His His
            260

<210> SEQ ID NO 90
<211> LENGTH: 10
<212> TYPE: PRT
```

<213> ORGANISM: Homo sapiens

<400> SEQUENCE: 90

Glu Gln Lys Leu Ile Ser Glu Glu Asp Leu
1               5                   10

<210> SEQ ID NO 91
<211> LENGTH: 264
<212> TYPE: PRT
<213> ORGANISM: Artificial Sequence
<220> FEATURE:
<223> OTHER INFORMATION: Pre-pro-BDNF(-RGR; Q79S)-T7-His6

<400> SEQUENCE: 91

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Ser Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 92
<211> LENGTH: 264
<212> TYPE: PRT
<213> ORGANISM: Artificial Sequence
<220> FEATURE:
<223> OTHER INFORMATION: Pre-pro-BDNF(-RGR; W19N)-T7-His6

<400> SEQUENCE: 92

Met Thr Ile Leu Phe Leu Thr Met Val Ile Ser Tyr Phe Gly Cys Met

```
1               5                   10                  15
Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
                35                  40                  45

Pro Lys Ala Gly Ser Arg Gly Leu Thr Ser Leu Ala Asp Thr Phe Glu
                50                  55                  60

His Val Ile Glu Glu Leu Leu Asp Glu Asp Gln Lys Val Arg Pro Asn
65                      70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
                100                 105                 110

Tyr Lys Asn Tyr Leu Asp Ala Ala Asn Met Ser Met Arg Val Arg Arg
                115                 120                 125

His Ser Asp Pro Ala Arg Arg Gly Glu Leu Ser Val Cys Asp Ser Ile
                130                 135                 140

Ser Glu Asn Val Thr Ala Ala Asp Lys Lys Thr Ala Val Asp Met Ser
145                     150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
                180                 185                 190

Lys Glu Gly Cys Arg Gly Ile Asp Lys Arg His Trp Asn Ser Gln Cys
                195                 200                 205

Arg Thr Thr Gln Ser Tyr Val Arg Ala Leu Thr Met Asp Ser Lys Lys
                210                 215                 220

Arg Ile Gly Trp Arg Phe Ile Arg Ile Asp Thr Ser Cys Val Cys Thr
225                     230                 235                 240

Leu Thr Ile Lys Gly Ser Gly Met Ala Ser Met Thr Gly Gly Gln Gln
                245                 250                 255

Met Gly His His His His His His
                260

<210> SEQ ID NO 93
<211> LENGTH: 264
<212> TYPE: PRT
<213> ORGANISM: Artificial Sequence
<220> FEATURE:
<223> OTHER INFORMATION: Pre-pro-BDNF(-RGR; K25N)-T7-His6

<400> SEQUENCE: 93

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
                35                  40                  45

Pro Lys Ala Gly Ser Arg Gly Leu Thr Ser Leu Ala Asp Thr Phe Glu
                50                  55                  60

His Val Ile Glu Glu Leu Leu Asp Glu Asp Gln Lys Val Arg Pro Asn
65                      70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
```

```
            100                 105                 110
Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
        130                 135                 140

Ser Glu Trp Val Thr Ala Ala Asp Asn Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
        210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 94
<211> LENGTH: 264
<212> TYPE: PRT
<213> ORGANISM: Artificial Sequence
<220> FEATURE:
<223> OTHER INFORMATION: Pre-pro-BDNF(-RGR; D30N)-T7-His6

<400> SEQUENCE: 94

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
        130                 135                 140

Ser Glu Trp Val Thr Ala Ala Asp Lys Lys Thr Ala Val Asn Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
```

195                 200                 205
Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 95
<211> LENGTH: 264
<212> TYPE: PRT
<213> ORGANISM: Artificial Sequence
<220> FEATURE:
<223> OTHER INFORMATION: Pre-pro-BDNF(-RGR; G33N)-T7-His6

<400> SEQUENCE: 95

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Asn Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 96
<211> LENGTH: 264
<212> TYPE: PRT

<213> ORGANISM: Artificial Sequence
<220> FEATURE:
<223> OTHER INFORMATION: Pre-pro-BDNF(-RGR; T35N)-T7-His6

<400> SEQUENCE: 96

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
130                 135                 140

Ser Glu Trp Val Thr Ala Ala Asp Lys Lys Thr Ala Val Asp Met Ser
145                 150                 155                 160

Gly Gly Asn Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260
```

<210> SEQ ID NO 97
<211> LENGTH: 264
<212> TYPE: PRT
<213> ORGANISM: Artificial Sequence
<220> FEATURE:
<223> OTHER INFORMATION: Pre-pro-BDNF(-RGR; P43N)-T7-His6

<400> SEQUENCE: 97

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
50                  55                  60
```

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
        130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Asn Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
            195                 200                 205

Arg Thr Thr Gln Ser Tyr Val Arg Ala Leu Thr Met Asp Ser Lys Lys
        210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 98
<211> LENGTH: 264
<212> TYPE: PRT
<213> ORGANISM: Artificial Sequence
<220> FEATURE:
<223> OTHER INFORMATION: Pre-pro-BDNF(-RGR; P43N, V42G)-T7-His6

<400> SEQUENCE: 98

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Leu
            20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
        50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
        130                 135                 140

Ser Glu Trp Val Thr Ala Ala Asp Lys Lys Thr Ala Val Asp Met Ser
145                 150                 155                 160

```
Gly Gly Thr Val Thr Val Leu Glu Lys Gly Asn Val Ser Lys Gly Gln
            165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
            195                 200             205

Arg Thr Thr Gln Ser Tyr Val Arg Ala Leu Thr Met Asp Ser Lys Lys
            210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
            245                 250                 255

Met Gly His His His His His His
            260

<210> SEQ ID NO 99
<211> LENGTH: 264
<212> TYPE: PRT
<213> ORGANISM: Artificial Sequence
<220> FEATURE:
<223> OTHER INFORMATION: Pre-pro-BDNF(-RGR; M61S, P60G)-T7-His6

<400> SEQUENCE: 99

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
        50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Phe Leu Leu Glu Glu
            100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
            130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
            165                 170                 175

Leu Lys Gln Tyr Phe Tyr Glu Thr Lys Cys Asn Gly Ser Gly Tyr Thr
            180                 185                 190

Lys Glu Gly Cys Arg Gly Ile Asp Lys Arg His Trp Asn Ser Gln Cys
            195                 200                 205

Arg Thr Thr Gln Ser Tyr Val Arg Ala Leu Thr Met Asp Ser Lys Lys
            210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
            245                 250                 255
```

```
Met Gly His His His His His His
            260
```

<210> SEQ ID NO 100
<211> LENGTH: 264
<212> TYPE: PRT
<213> ORGANISM: Artificial Sequence
<220> FEATURE:
<223> OTHER INFORMATION: Pre-pro-BDNF(-RGR; G62N, Y63G)-T7-His6

<400> SEQUENCE: 100

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Asn Gly Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260
```

<210> SEQ ID NO 101
<211> LENGTH: 264
<212> TYPE: PRT
<213> ORGANISM: Artificial Sequence
<220> FEATURE:
<223> OTHER INFORMATION: Pre-pro-BDNF(-RGR; Q79T)-T7-His6

<400> SEQUENCE: 101

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30
```

```
Ala Tyr Pro Gly Val Arg Thr His Gly Thr Leu Glu Ser Val Asn Gly
         35                  40                  45

Pro Lys Ala Gly Ser Arg Gly Leu Thr Ser Leu Ala Asp Thr Phe Glu
         50                  55                  60

His Val Ile Glu Glu Leu Leu Asp Glu Asp Gln Lys Val Arg Pro Asn
 65                  70                  75                  80

Glu Glu Asn Asn Lys Asp Ala Asp Leu Tyr Thr Ser Arg Val Met Leu
                 85                  90                  95

Ser Ser Gln Val Pro Leu Glu Pro Pro Leu Leu Phe Leu Leu Glu Glu
             100                 105                 110

Tyr Lys Asn Tyr Leu Asp Ala Ala Asn Met Ser Met Arg Val Arg Arg
             115                 120                 125

His Ser Asp Pro Ala Arg Arg Gly Glu Leu Ser Val Cys Asp Ser Ile
         130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                 165                 170                 175

Leu Lys Gln Tyr Phe Tyr Glu Thr Lys Cys Asn Pro Met Gly Tyr Thr
             180                 185                 190

Lys Glu Gly Cys Arg Gly Ile Asp Lys Arg His Trp Asn Ser Thr Cys
             195                 200                 205

Arg Thr Thr Gln Ser Tyr Val Arg Ala Leu Thr Met Asp Ser Lys Lys
         210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                 245                 250                 255

Met Gly His His His His His His
             260

<210> SEQ ID NO 102
<211> LENGTH: 264
<212> TYPE: PRT
<213> ORGANISM: Artificial Sequence
<220> FEATURE:
<223> OTHER INFORMATION: Pre-pro-BDNF(-RGR; W76N)-T7-His6

<400> SEQUENCE: 102

Met Thr Ile Leu Phe Leu Thr Met Val Ile Ser Tyr Phe Gly Cys Met
1                5                  10                  15

Lys Ala Ala Pro Met Lys Glu Ala Asn Ile Arg Gly Gln Gly Gly Leu
             20                  25                  30

Ala Tyr Pro Gly Val Arg Thr His Gly Thr Leu Glu Ser Val Asn Gly
         35                  40                  45

Pro Lys Ala Gly Ser Arg Gly Leu Thr Ser Leu Ala Asp Thr Phe Glu
         50                  55                  60

His Val Ile Glu Glu Leu Leu Asp Glu Asp Gln Lys Val Arg Pro Asn
 65                  70                  75                  80

Glu Glu Asn Asn Lys Asp Ala Asp Leu Tyr Thr Ser Arg Val Met Leu
                 85                  90                  95

Ser Ser Gln Val Pro Leu Glu Pro Pro Leu Leu Phe Leu Leu Glu Glu
             100                 105                 110

Tyr Lys Asn Tyr Leu Asp Ala Ala Asn Met Ser Met Arg Val Arg Arg
             115                 120                 125
```

His Ser Asp Pro Ala Arg Arg Gly Glu Leu Ser Val Cys Asp Ser Ile
        130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Asn Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 103
<211> LENGTH: 264
<212> TYPE: PRT
<213> ORGANISM: Artificial Sequence
<220> FEATURE:
<223> OTHER INFORMATION: Pre-pro-BDNF(-RGR; M92N)-T7-His6

<400> SEQUENCE: 103

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Asn Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
            245                 250                 255

Met Gly His His His His His His
            260

<210> SEQ ID NO 104
<211> LENGTH: 264
<212> TYPE: PRT
<213> ORGANISM: Artificial Sequence
<220> FEATURE:
<223> OTHER INFORMATION: Pre-pro-BDNF(-RGR; D106N)-T7-His6

<400> SEQUENCE: 104

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asn Thr Ser Cys Val Cys Thr
225                 230                 235                 240

Leu Thr Ile Lys Gly Ser Gly Met Ala Ser Met Thr Gly Gly Gln Gln
            245                 250                 255

Met Gly His His His His His His
            260

<210> SEQ ID NO 105
<211> LENGTH: 264
<212> TYPE: PRT
<213> ORGANISM: Artificial Sequence
<220> FEATURE:
<223> OTHER INFORMATION: Pre-pro-BDNF(-RGR; T112N)-T7-His6

<400> SEQUENCE: 105

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Asn
225                 230                 235                 240

Leu Thr Ile Lys Gly Ser Gly Met Ala Ser Met Thr Gly Gly Gln Gln
                245                 250                 255

Met Gly His His His His His His
            260

<210> SEQ ID NO 106
<211> LENGTH: 264
<212> TYPE: PRT
<213> ORGANISM: Artificial Sequence
<220> FEATURE:
<223> OTHER INFORMATION: pre-pro-BDNF(-RGR; Q79T, R81N)-T7-His6

<400> SEQUENCE: 106

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu

```
                85                  90                  95
Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
            130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
            165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Thr Cys
            195                 200                 205

Asn Thr Thr Gln Ser Tyr Val Arg Ala Leu Thr Met Asp Ser Lys Lys
            210                 215                 220

Arg Ile Gly Trp Arg Phe Ile Arg Ile Asp Thr Ser Cys Val Cys Thr
225                 230                 235                 240

Leu Thr Ile Lys Gly Ser Gly Met Ala Ser Met Thr Gly Gly Gln Gln
            245                 250                 255

Met Gly His His His His His His
            260

<210> SEQ ID NO 107
<211> LENGTH: 499
<212> TYPE: PRT
<213> ORGANISM: Artificial Sequence
<220> FEATURE:
<223> OTHER INFORMATION:
    pre-pro(IgA)-BDNF(-RGR)_(G3D)4-G3S_VH<TfR>8D3-CH1-EPKSC-His6

<400> SEQUENCE: 107

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
            50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
            85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
            115                 120                 125

Ala Pro Pro Ala Pro His Ser Asp Pro Ala Arg Arg Gly Glu Leu Ser
            130                 135                 140

Val Cys Asp Ser Ile Ser Glu Trp Val Thr Ala Ala Asp Lys Lys Thr
145                 150                 155                 160

Ala Val Asp Met Ser Gly Gly Thr Val Thr Val Leu Glu Lys Val Pro
            165                 170                 175
```

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
        195                 200                 205

Trp Asn Ser Gln Cys Arg Thr Thr Gln Ser Tyr Val Arg Ala Leu Thr
    210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Gly Asp Gly Gly
            245                 250                 255

Asp Gly Gly Asp Gly Gly Asp Gly Gly Ser Glu Val Gln
        260                 265                 270

Leu Val Glu Ser Gly Gly Leu Val Gln Pro Gly Asn Ser Leu Thr
    275                 280                 285

Leu Ser Cys Val Ala Ser Gly Phe Thr Phe Ser Asn Tyr Gly Met His
    290                 295                 300

Trp Ile Arg Gln Ala Pro Lys Lys Gly Leu Glu Trp Ile Ala Met Ile
305                 310                 315                 320

Tyr Tyr Asp Ser Ser Lys Met Asn Tyr Ala Asp Thr Val Lys Gly Arg
            325                 330                 335

Phe Thr Ile Ser Arg Asp Asn Ser Lys Asn Thr Leu Tyr Leu Glu Met
            340                 345                 350

Asn Ser Leu Arg Ser Glu Asp Thr Ala Met Tyr Tyr Cys Ala Val Pro
        355                 360                 365

Thr Ser His Tyr Val Val Asp Val Trp Gly Gln Gly Val Ser Val Thr
        370                 375                 380

Val Ser Ser Ala Ser Thr Lys Gly Pro Ser Val Phe Pro Leu Ala Pro
385                 390                 395                 400

Ser Ser Lys Ser Thr Ser Gly Gly Thr Ala Ala Leu Gly Cys Leu Val
            405                 410                 415

Lys Asp Tyr Phe Pro Glu Pro Val Thr Val Ser Trp Asn Ser Gly Ala
        420                 425                 430

Leu Thr Ser Gly Val His Thr Phe Pro Ala Val Leu Gln Ser Ser Gly
    435                 440                 445

Leu Tyr Ser Leu Ser Ser Val Val Thr Val Pro Ser Ser Leu Gly
    450                 455                 460

Thr Gln Thr Tyr Ile Cys Asn Val Asn His Lys Pro Ser Asn Thr Lys
465                 470                 475                 480

Val Asp Lys Lys Val Glu Pro Lys Ser Cys Gly Ser Gly His His His
            485                 490                 495

His His His

<210> SEQ ID NO 108
<211> LENGTH: 494
<212> TYPE: PRT
<213> ORGANISM: Artificial Sequence
<220> FEATURE:
<223> OTHER INFORMATION:
      pre-pro(IgA)-BDNF(-RGR)_(G3D)4-G3S_VH<TfR>8D3-CH1-His6

<400> SEQUENCE: 108

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
    35                  40                  45

Pro Lys Ala Gly Ser Arg Gly Leu Thr Ser Leu Ala Asp Thr Phe Glu
50                   55                  60

His Val Ile Glu Glu Leu Leu Asp Glu Asp Gln Lys Val Arg Pro Asn
65                   70                  75                  80

Glu Glu Asn Asn Lys Asp Ala Asp Leu Tyr Thr Ser Arg Val Met Leu
                85                  90                  95

Ser Ser Gln Val Pro Leu Glu Pro Leu Leu Phe Leu Leu Glu Glu
            100                 105                 110

Tyr Lys Asn Tyr Leu Asp Ala Ala Asn Met Ser Met Gly Ser Val Val
        115                 120                 125

Ala Pro Pro Ala Pro His Ser Asp Pro Ala Arg Arg Gly Glu Leu Ser
    130                 135                 140

Val Cys Asp Ser Ile Ser Glu Trp Val Thr Ala Ala Asp Lys Lys Thr
145                 150                 155                 160

Ala Val Asp Met Ser Gly Gly Thr Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
    195                 200                 205

Trp Asn Ser Gln Cys Arg Thr Thr Gln Ser Tyr Val Arg Ala Leu Thr
    210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Gly Asp Gly Gly Gly
                245                 250                 255

Asp Gly Gly Gly Asp Gly Gly Gly Asp Gly Gly Ser Glu Val Gln
                260                 265                 270

Leu Val Glu Ser Gly Gly Gly Leu Val Gln Pro Gly Asn Ser Leu Thr
    275                 280                 285

Leu Ser Cys Val Ala Ser Gly Phe Thr Phe Ser Asn Tyr Gly Met His
    290                 295                 300

Trp Ile Arg Gln Ala Pro Lys Lys Gly Leu Glu Trp Ile Ala Met Ile
305                 310                 315                 320

Tyr Tyr Asp Ser Ser Lys Met Asn Tyr Ala Asp Thr Val Lys Gly Arg
                325                 330                 335

Phe Thr Ile Ser Arg Asp Asn Ser Lys Asn Thr Leu Tyr Leu Glu Met
                340                 345                 350

Asn Ser Leu Arg Ser Glu Asp Thr Ala Met Tyr Tyr Cys Ala Val Pro
            355                 360                 365

Thr Ser His Tyr Val Val Asp Val Trp Gly Gln Gly Val Ser Val Thr
    370                 375                 380

Val Ser Ser Ala Ser Thr Lys Gly Pro Ser Val Phe Pro Leu Ala Pro
385                 390                 395                 400

Ser Ser Lys Ser Thr Ser Gly Gly Thr Ala Ala Leu Gly Cys Leu Val
            405                 410                 415

Lys Asp Tyr Phe Pro Glu Pro Val Thr Val Ser Trp Asn Ser Gly Ala
        420                 425                 430

Leu Thr Ser Gly Val His Thr Phe Pro Ala Val Leu Gln Ser Ser Gly
    435                 440                 445

Leu Tyr Ser Leu Ser Ser Val Val Thr Val Pro Ser Ser Leu Gly

```
                450             455             460
Thr Gln Thr Tyr Ile Cys Asn Val Asn His Lys Pro Ser Asn Thr Lys
465                 470                 475                 480

Val Asp Lys Lys Val Gly Ser Gly His His His His His
                485                 490

<210> SEQ ID NO 109
<211> LENGTH: 485
<212> TYPE: PRT
<213> ORGANISM: Artificial Sequence
<220> FEATURE:
<223> OTHER INFORMATION:
      pre-pro(IgA)-BDNF(-RGR)_(G3D)4-G3S_VH<TfR>8D3-CH1

<400> SEQUENCE: 109

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Gly Ser Val Val
        115                 120                 125

Ala Pro Pro Ala Pro His Ser Asp Pro Ala Arg Arg Gly Glu Leu Ser
    130                 135                 140

Val Cys Asp Ser Ile Ser Glu Trp Val Thr Ala Ala Asp Lys Lys Thr
145                 150                 155                 160

Ala Val Asp Met Ser Gly Gly Thr Val Thr Val Leu Glu Lys Val Pro
                165                 170                 175

Val Ser Lys Gly Gln Leu Lys Gln Tyr Phe Tyr Glu Thr Lys Cys Asn
            180                 185                 190

Pro Met Gly Tyr Thr Lys Glu Gly Cys Arg Gly Ile Asp Lys Arg His
        195                 200                 205

Trp Asn Ser Gln Cys Arg Thr Thr Gln Ser Tyr Val Arg Ala Leu Thr
    210                 215                 220

Met Asp Ser Lys Lys Arg Ile Gly Trp Arg Phe Ile Arg Ile Asp Thr
225                 230                 235                 240

Ser Cys Val Cys Thr Leu Thr Ile Lys Gly Gly Asp Gly Gly Gly
                245                 250                 255

Asp Gly Gly Asp Gly Gly Gly Asp Gly Gly Ser Glu Val Gln
            260                 265                 270

Leu Val Glu Ser Gly Gly Leu Val Gln Pro Gly Asn Ser Leu Thr
        275                 280                 285

Leu Ser Cys Val Ala Ser Gly Phe Thr Phe Ser Asn Tyr Gly Met His
    290                 295                 300

Trp Ile Arg Gln Ala Pro Lys Lys Gly Leu Glu Trp Ile Ala Met Ile
305                 310                 315                 320
```

-continued

```
Tyr Tyr Asp Ser Ser Lys Met Asn Tyr Ala Asp Thr Val Lys Gly Arg
            325                 330                 335

Phe Thr Ile Ser Arg Asp Asn Ser Lys Asn Thr Leu Tyr Leu Glu Met
            340                 345                 350

Asn Ser Leu Arg Ser Glu Asp Thr Ala Met Tyr Tyr Cys Ala Val Pro
        355                 360                 365

Thr Ser His Tyr Val Val Asp Val Trp Gly Gln Gly Val Ser Val Thr
    370                 375                 380

Val Ser Ser Ala Ser Thr Lys Gly Pro Ser Val Phe Pro Leu Ala Pro
385                 390                 395                 400

Ser Ser Lys Ser Thr Ser Gly Gly Thr Ala Ala Leu Gly Cys Leu Val
            405                 410                 415

Lys Asp Tyr Phe Pro Glu Pro Val Thr Val Ser Trp Asn Ser Gly Ala
            420                 425                 430

Leu Thr Ser Gly Val His Thr Phe Pro Ala Val Leu Gln Ser Ser Gly
        435                 440                 445

Leu Tyr Ser Leu Ser Ser Val Val Thr Val Pro Ser Ser Ser Leu Gly
    450                 455                 460

Thr Gln Thr Tyr Ile Cys Asn Val Asn His Lys Pro Ser Asn Thr Lys
465                 470                 475                 480

Val Asp Lys Lys Val
            485
```

RECOMBINANT POLYPEPTIDE PRODUCTION METHODS

This application claims priority to and is a continuation of pending U.S. patent application Ser. No. 15/106,205, filed on Jun. 17, 2016, which in turn claims priority to National Stage Application of PCT/EP2014/077196, filed on Dec. 10, 2014, which in turn claims priority from European Application No. 13198738.0, flied on Dec. 20, 2013. Each of these applications is hereby incorporated by reference herein in its entirety.

Herein are reported methods for amongst other things increasing the yield of biologically active recombinantly produced polypeptides.

BACKGROUND OF THE INVENTION

Today most biopharmaceuticals are produced in animal (mammalian) cells, which usually secrete the recombinant polypeptide of interest with high efficiency, quality and appropriate post-translational (secondary) modifications (such as e.g. glycosylation) into the cultivation medium. However, some fusion polypeptides, especially complex fusion polypeptides, polypeptides with low solubility or folding difficulties, as well as polypeptides interacting with the cell expressing it are often obtained at very low yields.

For example, antibodies are usually expressed in mammalian cells with high efficiency in biologically active form. However, fusion polypeptides comprising an antibody, e.g. green fluorescent protein (GFP) antibody conjugates, are expressed and/or secreted not at all, although such proteins would be highly interesting for experimental and diagnostic approaches (see e.g. WO 2011/135040).

In certain cases difficult to express polypeptides can be produced as soluble secreted inactive precursor proteins e.g. so called zymogens in the case of proteases which can be matured afterwards in vitro e.g. by proteolytic activation. In other cases polypeptides, which are detrimental for a specific host cell, can be expressed as inactive insoluble protein aggregates within the cell (inclusion bodies (IBs)) and afterwards refolded in vitro. However the processing of pro-polypeptides can be difficult or not possible at all. Moreover, the obtained mature polypeptides do not contain all posttranslational modifications.

Examples of poorly expressed polypeptides are neurotrophic factors like NGF, BDNF, GDNF and NT-3 (see e.g. Xia, Ch.-F., J. Gene Med. 10 (2008) 306-315; Boado, R. J., Pharm. Res. 24 (2007) 1772-1787; Negro, A., et al., J. Neurochem. 62 (1994) 471-478).

In WO 2008/005847 a method of producing factor viii proteins by recombinant methods is reported. Peptide extended glycosylated polypeptides are reported in WO 02/02597. In WO 2007/044323 fusion proteins for blood-brain barrier delivery are reported. Nerve cell growth modulators (amphibodies) are reported in WO 00/64482. In WO 2012/087835 are reported compositions and methods for enhancing protein folding. Stable and soluble antibodies inhibiting TNFalpha are reported in WO 2006/131013. In WO 00/23473 interferon-beta fusion proteins and uses are reported.

SUMMARY OF THE INVENTION

Herein are reported methods for improving the production process of a recombinantly produced polypeptide.

The improvement can be e.g. an increased yield, a more robust production process, a more simple process, and/or a reduced complexity during downstream processing.

It has to be pointed out that the improvement is achieved without impairing the biophysical and/or biochemical properties and/or biological function of the polypeptide. In certain cases one or more of these properties are even improved.

In a first aspect reported herein is that it has been found that by the introduction of one or more glycosylation sites the recombinant production of a polypeptide in a mammalian cell can be improved.

One aspect as reported herein is a method for producing a recombinant polypeptide using a variant polypeptide comprising the following steps:

cultivating a mammalian cell comprising a nucleic acid encoding a variant polypeptide wherein the amino acid sequence of the polypeptide has been modified by i) one or more mutations of surface located amino acid residues resulting in a lower isoelectric point of the variant polypeptide compared to the polypeptide, and/or ii) a linker peptide connecting two polypeptides of a fusion polypeptide, and/or iii) an N- or C-terminally fused tag containing amino acids resulting in a lower isoelectric point of the polypeptide, recovering the recombinant variant polypeptide from the cell or the cultivation medium and thereby producing the recombinant polypeptide.

Thus, herein is reported a method for producing a recombinant polypeptide using a variant polypeptide comprising the following steps:

cultivating a eukaryotic cell (in one embodiment a mammalian cell) comprising a nucleic acid encoding a variant polypeptide wherein the amino acid sequence of the polypeptide has been modified to comprise one or more artificial glycosylation sites, recovering the variant recombinant polypeptide from the cell or the cultivation medium and thereby producing the recombinant polypeptide.

One aspect as reported herein is a method for producing a recombinant polypeptide using a variant polypeptide comprising the following steps:

providing a nucleic acid encoding the polypeptide, modifying the nucleic acid to encode a variant polypeptide wherein the amino acid sequence of the polypeptide has been modified to comprise one or more artificial glycosylation sites, introducing the nucleic acid into a eukaryotic cell (in one embodiment a mammalian cell), cultivating the eukaryotic cell, and recovering the variant recombinant polypeptide from the cell or the cultivation medium and thereby producing the recombinant polypeptide.

The methods as reported herein are especially suited e.g. for polypeptides which are poorly or not at all expressed/secreted in mammalian cells.

The introduced glycosylation site(s) can be (located independently of each other) either in the polypeptide itself, or in a linker peptide connecting two polypeptides of a fusion polypeptide, or it can be a specific glycosylation-tag.

In one embodiment the polypeptide comprises a glycosylation-tag.

In one embodiment the polypeptide comprises an artificial glycosylation site. In one embodiment the artificial glycosylation site is introduced by point mutation of a surface localized amino acid.

In a second aspect it is reported herein that it has been found that by replacing in a pro-polypeptide the endogenous protease cleavage site between the pro-segment and the mature polypeptide with an exogenous (with respect to the origin of the polypeptide) or artificial protease cleavage site the yield of the mature polypeptide can be improved. This change improves the processing of the pro-polypeptide into the mature form.

Thus, one aspect as reported herein is a method for producing a recombinant polypeptide using a variant pro-polypeptide comprising the following steps:
  cultivating a eukaryotic cell (in one embodiment a mammalian cell) comprising a nucleic acid encoding the polypeptide as pro-polypeptide (fusion polypeptide of a pro-segment and the polypeptide) wherein the endogenous enzymatic cleavage site between the pro-segment and the polypeptide is replaced by an exogenous protease cleavage site,
  recovering the recombinant variant polypeptide or the variant pro-polypeptide from the cell or the cultivation medium and thereby producing the recombinant polypeptide.

One aspect as reported herein is a method for producing a recombinant polypeptide using a variant pro-polypeptide comprising the following steps:
  providing a nucleic acid encoding the polypeptide as pro-polypeptide (fusion polypeptide of a pro-segment and the polypeptide),
  modifying the nucleic acid to encode a variant pro-polypeptide wherein the endogenous enzymatic cleavage site between the pro-segment and the polypeptide is replaced by an exogenous protease cleavage site,
  introducing the nucleic acid into a eukaryotic cell (in one embodiment a mammalian cell),
  cultivating the eukaryotic cell, and
  recovering the recombinant variant polypeptide or variant pro-polypeptide from the cell or the cultivation medium and thereby producing the recombinant polypeptide.

In one embodiment the exogenous protease cleavage site is selected from the group comprising a plasmin cleavage site, a furin cleavage site, an IgA protease cleavage site, a TEV protease cleavage site (Tobacco Etch Virus), a Granzyme B cleavage site, a Thrombin cleavage site, a factor 10 cleavage site, an Enterokinase cleavage site, a subtilisin cleavage site, a cathepsin cleavage site, a metallo proteinase cleavage site, an IDES protease cleavage site, a PreScission protease cleavage site, or functional variants thereof. In one embodiment the exogenous protease cleavage site is an IgA protease cleavage site.

In one embodiment the cleavage of the pro-polypeptide is in the cultivation medium. In one embodiment an exogenous protease capable of cleaving the exogenous protease cleavage site is added to the cultivation medium. In one embodiment the addition is during the cultivation phase. In one embodiment the addition is after the cultivation phase.

In one embodiment the exogenous protease is co-expressed from the cell expressing the pro-polypeptide.

In one embodiment the cultivation is a co-cultivation of a cell expressing the pro-polypeptide and a cell expressing the exogenous protease.

In one embodiment the cleavage is after the separation of the cells from the cultivation medium. In one embodiment the cleavage is during downstream processing. In one embodiment the cleavage is on a chromatography column.

In a third aspect it is reported herein that it has been found that with the lowering of the isoelectric point of a polypeptide the recombinant production of the polypeptide in a mammalian cell can be improved.

Thus, one aspect as reported herein is a method for producing a recombinant polypeptide using a variant polypeptide comprising the following steps:
  cultivating a eukaryotic cell (in one embodiment a mammalian cell) comprising a nucleic acid encoding a variant polypeptide wherein the amino acid sequence of the polypeptide has been modified by one or more mutations of surface located amino acid residues resulting in a lower isoelectric point of the variant polypeptide compared to the polypeptide,
  recovering the recombinant variant polypeptide from the cell or the cultivation medium and thereby producing the recombinant polypeptide.

One aspect as reported herein is a method for producing a recombinant polypeptide using a variant polypeptide comprising the following steps:
  providing a nucleic acid encoding the polypeptide,
  modifying the nucleic acid to encode a variant polypeptide wherein the amino acid sequence of the polypeptide has been modified by one or more mutations of surface located amino acid residues resulting in a lower isoelectric point of the variant polypeptide compared to the polypeptide,
  introducing the nucleic acid into a eukaryotic cell (in one embodiment a mammalian cell),
  cultivating the eukaryotic cell, and
  recovering the recombinant variant polypeptide from the cell or the cultivation medium and thereby producing the recombinant polypeptide.

In one embodiment the polypeptide has an isoelectric point above 9 (high isoelectric point, basic isoelectric point) and the variant polypeptide has an isoelectric point that is 0.5 or more pH units lower (more acidic) compared to the (parent/wild-type) polypeptide.

In one embodiment the polypeptide is a neutrophin/neurotrophic factor.

In one embodiment the isoelectric point is lowered by the introduction of a negatively charged moiety.

In one embodiment the negatively charged moiety is a linker peptide.

In one embodiment the negatively charged moiety is a surface localized amino acid residue. In one embodiment one or more basic amino acid residue(s) is(are) replaced by neutral hydrophilic amino acid residue(s) and/or acidic amino acid residue(s) or combinations thereof.

In a fourth aspect it is reported herein that it has been found that by adjusting linker peptide length and connectivity the recombinant production of a fusion polypeptide in a eukaryotic cell, such as e.g. a mammalian cell, can be improved.

Thus, one aspect as reported herein is a method for producing a (recombinant) fusion-polypeptide comprising the following steps:
  cultivating a eukaryotic cell (in one embodiment a mammalian cell) comprising a nucleic acid encoding the fusion-polypeptide,
  recovering the (recombinant) fusion-polypeptide from the cell or the cultivation medium and thereby producing the (recombinant) fusion-polypeptide.

In one embodiment one part of the fusion polypeptide is a neurotrophin and the other part of the fusion polypeptide is an antibody or antibody fragment.

In a fifth aspect it is reported herein that it has been found that i) by the introduction of one or more glycosylation sites, and/or
ii) by replacing in a pro-polypeptide the endogenous protease cleavage site between the pro-segment and the polypeptide with an exogenous (with respect to the origins of the parts of the fusion-polypeptide) or artificial protease cleavage site, and/or
iii) by lowering of the isoelectric point of the polypeptide, and/or
iv) by adjusting linker peptide length, connectivity and charge, the recombinant production of the polypeptide in a mammalian cell can be improved.

Thus, one aspect as reported herein is a method for producing a (recombinant) (fusion-)polypeptide comprising the following steps:

cultivating a eukaryotic cell (in one embodiment a mammalian cell) comprising a nucleic acid encoding a variant (fusion-)polypeptide wherein the amino acid sequence of the (fusion-)polypeptide has been modified
i) by the introduction of one or more artificial glycosylation sites, and/or
ii) by replacing in a pro-(fusion-)polypeptide the endogenous protease cleavage site between the pro-segment and the (fusion-)polypeptide with an exogenous (with respect to the origins of the parts of the fusion-polypeptide) or artificial protease cleavage site, and/or
iii) by lowering of the isoelectric point of the (fusion-)polypeptide, and/or
iv) by one or more of adjusting linker peptide length, adjusting linker connectivity, adjusting linker charge, introducing one or more mutations of surface located amino acid residues resulting in a lower isoelectric point of the (fusion-)polypeptide,
recovering the (fusion-)polypeptide or (fusion-)pro-polypeptide from the cell or the cultivation medium and thereby producing the (recombinant) (fusion-)polypeptide.

One aspect as reported herein is a method for producing a (recombinant) fusion-polypeptide comprising the following steps:

providing a nucleic acid encoding the fusion-polypeptide,
modifying the nucleic acid to encode a variant fusion-polypeptide wherein the amino acid sequence of the fusion-polypeptide has been modified by adjusting linker peptide length, adjusting linker connectivity, adjusting linker charge, introducing one or more mutations of surface located amino acid residues resulting in a lower isoelectric point of the fusion-polypeptide,
introducing the nucleic acid into a eukaryotic cell (in one embodiment a mammalian cell),
cultivating the eukaryotic cell, and
recovering the (recombinant) variant fusion-polypeptide from the cell or the cultivation medium and thereby producing the (recombinant) fusion-polypeptide.

In one embodiment of the previous aspects the fusion-polypeptide comprises a biologically active entity, a linker peptide, and a monovalent binding entity which binds to a blood-brain-barrier (BBB) receptor.

In one embodiment the blood brain barrier receptor is selected from the group consisting of transferrin receptor, insulin receptor, insulin-like growth factor receptor, low density lipoprotein receptor-related protein (LRP)/alpha 2-macroglobulin receptor, low density lipoprotein receptor-related protein 8 (also known as apolipoprotein E receptor 2 (ApoER2)), low density lipoprotein receptor-related protein 1 (also known as alpha-2-macroglobulin receptor (A2MR)) and heparin-binding epidermal growth factor-like growth factor.

In one embodiment the linker peptide comprises one or more negatively charged amino acid residues. In one embodiment the linker peptide comprises two or more negatively charged amino acid residues. In one embodiment the linker peptide comprises two, or three, or four, or five negatively charged amino acid residues.

In one embodiment the biologically active entity is a neurotrophic factor. In one embodiment the neurotrophic factor is brain derived neurotrophic factor (BDNF).

In one embodiment the monovalent binding entity is binding to a blood brain barrier receptor and is a monovalent antibody fragment, preferably selected from scFv, Fv, scFab, Fab, VHH.

In one embodiment the fusion polypeptide is a single chain fusion polypeptide comprising as first part human brain-derived neurotrophic factor and as second part a single anti-transferrin receptor antibody Fab or scFv conjugated either directly or via a linker peptide to each other.

One aspect as reported herein is a fusion-polypeptide comprising
  exactly one wild-type neurotrophic factor polypeptide, or neurotrophic factor variant polypeptide, or fragment thereof with neurotrophic factor activity,
  a binding domain, and
  a linker peptide between the neurotrophic factor polypeptide and the antibody fragment.

One aspect as reported herein is a fusion-polypeptide with neurotrophic factor activity (e.g. dimeric complex) comprising
  exactly one type of wild-type neurotrophic factor polypeptide, or neurotrophic factor variant polypeptide or fragment thereof with neurotrophic factor activity,
  a binding domain, and
  a linker peptide between the neurotrophic factor polypeptide and the antibody fragment.

In one embodiment the binding domain is an antibody fragment binding site. In one embodiment the binding domain is an antibody fragment comprising an antibody binding site. In one embodiment the antibody fragment is specifically binding to a blood brain barrier receptor. In one embodiment the antibody fragment is a monovalent antibody fragment selected from the group comprising scFv, Fv, scFab, Fab, VHH.

In one embodiment the blood brain barrier receptor is selected from the group consisting of transferrin receptor, insulin receptor, insulin-like growth factor receptor, low density lipoprotein receptor-related protein (LRP)/alpha 2-macroglobulin receptor, low density lipoprotein receptor-related protein 8 (also known as apolipoprotein E receptor 2 (ApoER2)), low density lipoprotein receptor-related protein 1 (also known as alpha-2-macroglobulin receptor (A2MR)) and heparin-binding epidermal growth factor-like growth factor.

In one embodiment the fusion-polypeptide comprises a second monovalent or bivalent binding entity which does not bind to a BBB receptor.

One aspect as reported herein is a complex comprising
  as first component a fusion-polypeptide as reported herein, and
  as second component of a wild-type neurotrophic factor polypeptide, or neurotrophic factor variant polypeptide, or fragment thereof with neurotrophic factor activity.

One aspect as reported herein is a multimeric complex with neurotrophic factor activity comprising as first component a fusion-polypeptide as reported herein, and as second component of a wild-type neurotrophic factor polypeptide, or neurotrophic factor variant polypeptide, or fragment thereof with neurotrophic factor activity.

In one embodiment the complex is a dimeric complex.

In one embodiment of all aspects the neurotrophic factor is selected from nerve growth factor (NGF), brain derived neurotrophic factor (BDNF), glial cell line-derived neurotrophic factor (GDNF), neurotrophin 3 (NT-3), and neurotrophin 4 (NT-4). In one preferred embodiment the neurotrophic growth factor is BDNF.

All amino acid sequences as reported herein are specific aspects of the current invention.

DETAILED DESCRIPTION OF THE INVENTION

Reason(s) for low expression yields of recombinantly produced polypeptides in mammalian cells are often not known and generally not easy to determine.

Certain polypeptides can interfere with host cell functions upon expression. This can be e.g. miss-sorting to an incorrect cellular location or expression in a wrong spatial (e.g. cell type) and/or temporal (e.g. cell cycle dependent) context. In addition, increased recombinant expression and secretion of polypeptides can result in unfavorable condition of protein folding, e.g. resulting in protein aggregation and/or cellular stress responses. In conclusion, recombinant expression of polypeptides can be difficult (e.g. resulting in a low expression yield) or even be impossible in a specific host cell.

The methods as reported herein are exemplified in the following with specific polypeptides, fusion-polypeptides and antibody-fusion-polypeptides. These molecules are used merely as an example and should not be construed as a limitation of the scope of the current invention.

Neurotrophic proteins are considered to be of high therapeutic interest. For example, brain-derived neurotrophic factor (BDNF) is suggested to cure or alleviate symptoms of Alzheimer's, Parkinson's, Huntington's and perinatal white matter disease, Down and autism/Rett syndrome, schizophrenia, depression, eating disorders, amyotrophic lateral sclerosis, multiple sclerosis, neuronal injuries like that of the spinal cord as well as other diseases (Apfel, S.C., Clin. Chem. Lab Med. 39 (2001) 351-355; Nagahara, A. H. and Tuszynski, M. H., Nat. Rev. Drug Discov. 10 (2011) 209-219; Zuccato, C. and Cattaneo, E., Nature Reviews Neurology 5 (2009) 311-322; Thoenen, H. and Sendtner, M., Nature Neuroscience Supplement 5 (2002) 1046-1050; Gharami, K., et al., J. Neurochem. 105 (2008) 369-379).

In the human body neurotrophic proteins are of very low abundance and are often expressed by specialized cell types located in a very complex microenvironment (see e.g. Greenberg, M. E., et al., J. Neurosci. 29 (2009) 12764-12767). In line with its natural function, expression levels of neurotrophins in eukaryotic cells typically used for recombinant industrial production of such polypeptides (like CHO cells, COS cells, NSO cells, and HEK cells) are very low (Acklin, C., et al., Int. J. Pept. Protein Res. 41 (1993) 548-552).

I. Improved Expression by Introduction of N-Glycosylation Sites

One aspect as reported herein is that one or more (artificial) glycosylation sites are introduced in a polypeptide for recombinant production thereof. By the introduction of one or more (artificial) glycosylation site(s) the recombinant production of the polypeptide in a eukaryotic cell, especially in a mammalian cell, can be improved. This method is especially suited e.g. for polypeptides which are poorly or not at all expressed/secreted in mammalian cells. The introduced glycosylation site can either be in the polypeptide itself, or in a linker peptide connecting two polypeptides of a fusion-polypeptide, or it can be a specific glycosylation-tag. It is especially advantageous to introduce the glycosylation site by point mutation of a surface localized amino acid to generate an (artificial) N-glycosylation motif.

Example: Fusion-Polypeptides Comprising an Antibody Part and GFP

Exemplary fusion-polypeptides comprising an antibody and a GFP moiety were constructed.

A GlySer-linker (GGGGSGGGGSG; SEQ ID NO: 01) was used to fuse either i) a eGFP moiety (enhanced green fluorescent protein; SEQ ID NO: 02), or ii) a emGFP moiety (emerald green fluorescent protein; SEQ ID NO: 03), or iii) a tagGFP moiety (SEQ ID NO: 04) to the C-terminal ends of the heavy chains (HCs) of an anti-IGF-1R antibody of the subclass IgG1 (HC: SEQ ID NO: 05; LC: SEQ ID NO: 06). The different heavy chain-fusions have an amino acid sequence of SEQ ID NO: 07, 08, and 09.

Secretion of the antibody-fusion-polypeptides could not be detected at all in the cell culture supernatants of transiently transfected HEK293 cells using Western Blotting and/or a protein A based High-Performance Liquid Chromatography (HPLC) assay. Also biologically active GFP could not be monitored by its bioluminescent properties (GFP-specific fluorescence). But the fusion-polypeptides could be detected in the cell pellet fraction by Western Blot analysis. The results are shown in the following table.

TABLE 1

| GFP molecule | secreted fusion-polypeptide [µg/ml] |
|---|---|
| eGFP | <1 |
| emGFP | <1 |
| tagGFP | <1 |

<1 µg/ml = below limit of detection

Without being bound by this theory GFP is a cytoplasmic monomeric protein with a tendency to form (weak) dimers. Thus, the wild-type GFP is not destined "from nature" (the natural Aequorea Victoria jellyfish cell) to be secreted, and, therefore, the GFP molecule must be made suitable for secretion due to incompatibility with the mammalian cell secretion machinery.

In order to provide secreted GFP containing fusion-polypeptides a polypeptide derived from the human light-sensitive membrane-bound G protein-coupled opsin receptor found in photoreceptor cells of the retina has been included further in the fusion-polypeptide, i.e. as glycosylation-tag. With this glycosylation-tag additional (artificial) N-glycosylation sites are introduced in the fusion-polypeptide.

The opsin receptor derived polypeptide was fused directly, i.e. without intervening linker peptide, to the C-terminus of the GFP moiety. The opsin-derived polypeptide (NGTEGPNFYVPFSNATGVV; opsin-tag; SEQ ID NO: 10) comprises two N-glycosylation site motifs: the NOT motif and the NAT motif (general N-glycosylation site motif: NxS/T; Asn followed by any amino acid except Pro, followed by either Ser or Thr). Transient expression of the fusion-polypeptides comprising the opsin glycosylation tag (SEQ ID NO: 11) in HEK293 cells resulted in secretion of the fusion-polypeptide. The results are shown in the following table.

TABLE 2

| GFP molecule | Opsin-tag | secreted fusion polypeptide [µg/ml] |
|---|---|---|
| eGFP | no | <1 |
| eGFP | yes | 15 |

<1 µg/ml = below limit of detection

From SDS-PAGE analysis (band broadening) it can be seen that the secreted fusion-polypeptides contain additional carbohydrates.

The antibody-GFP-opsin-tag-fusion-polypeptides were purified with a two-step procedure, in particular, a protein A affinity chromatography followed by a size exclusion chromatography. The functionality of the antibody moiety within the fusion-polypeptide was demonstrated by binding to the IGF-1R receptor protein using surface plasmon resonance (BIAcore) and internalization into cells via receptor mediated endocytosis on cells over-expressing IGF-1R by FACS and/or confocal microscopy. The functionally of the GFP moiety was shown due to its green fluorescence characteristics.

Example: Neurotrophic Proteins

An exemplary neurotrophic protein is brain-derived neurotropic factor (BDNF).

i) Glycosylation-Tag

Human wild-type pre-pro-BDNF comprising a C-terminal T7-His6-tag (MASMTGGQQMG-HHHHHH; used for affinity purification; SEQ ID NO: 12) fused via a GSG-linker was expressed in HEK239 cells (pre-pro-BDNF-T7-His6; SEQ ID NO: 13). The amino acid sequence of mature BDNF does not contain an N-glycosylation site motif and is therefore not N-glycosylated. Mature BDNF is obtained in low yields of a few µg/ml only. The low expression yield could not be improved by optimization of the gene codon usage, or by removal of potential protease cleavage sites (pre-pro-BDNF(-RGR)-T7-His6), or by exchanging the native BDNF signal sequence by a signal sequence of a well expressed antibody (MGWSCIILFL VATATGVHS; SEQ ID NO: 14), or by an exchange of the BDNF pre-pro-segment with that of NGF. The results are shown in the following table (normalized to concentration of maturated BDNF).

TABLE 3

| BDNF molecule | deletion of RGR at the C-terminus | linker peptide | purification-tag | normalized secreted fusion polypeptide [µg/ml] |
|---|---|---|---|---|
| pre-pro-BDNF | no | GSG | none | 3-5 |
| pre-pro-BDNF | yes | GSG | none | 3-5 |
| pre-pro-BDNF (codon optimized) | yes | GSG | T7-His6 | 2.5-5 |
| pre-pro-BDNF (antibody signal sequence) | no | GSG | T7-His6 | 3 |
| pre-pro-BDNF (pre-pro from NGF) | no | GSG | T7-His6 | 0.5 |

In order to improve the (secretion) yield of BDNF (artificial) glycosylation sites were introduced into the BDNF molecule using opsin-glycosylation-tags of different length: 16 amino acid residues (NGTEGPNFYVPFSNAT; SEQ ID NO: 15), 19 amino acid residues (NGTEGPNFYVPFSNATGVV; SEQ ID NO: 10), and 20 amino acid residues (NGTEGPNFYVPFSNATGVVR; SEQ ID NO: 16). Using this modification the expression yield (normalized to concentration of maturated BDNF) could be improved. The results are shown in the following table (normalized to concentration of maturated BDNF).

TABLE 4

| BDNF molecule | deletion of RGR at the C-terminus | linker peptide | glycosylation-tag SEQ ID NO: | linker peptide | purification-tag | normalized secreted fusion polypeptide [µg/ml] |
|---|---|---|---|---|---|---|
| pre-pro-BDNF | no | GSG | no | no | T7-His6 | 3-5 |
| pre-pro-BDNF | yes | GSG | no | no | T7-His6 | 3-5 |
| pre-pro-BDNF (codon optimized) | yes | GSG | no | no | T7-His6 | 2.5-5 |
| pre-pro-BDNF (antibody signal sequence) | no | GSG | no | no | T7-His6 | 3 |
| pre-pro-BDNF (pre-pro from NGF) | no | GSG | no | no | T7-His6 | 0.5 |
| pre-pro-BDNF | yes | GSG | 15 | GSG | T7-His6 | >22* |
| pre-pro-BDNF | yes | GSG | 15 | GSG | His6 | >22* |
| pre-pro-BDNF | yes | GSG | 16 | no | His6 | >22* |

*exceeded linear range of quantification

Surprisingly, the BDNF variants comprising a glycosylation-tag had also an improved biological activity when compared to native non-glycosylated BDNF (CHO-TrkB-luciferase reporter gene assay). The results are shown in the following table.

TABLE 5

| BDNF molecule | deletion of RGR at the C-terminus | linker peptide | glycosylation-tag SEQ ID NO: | linker peptide | purification-tag | BDNF activity in TrkBluciferase assay, EC50 [nM] |
|---|---|---|---|---|---|---|
| pre-pro-BDNF | yes | GSG | no | no | T7-His6 | 3.4 |
| pre-pro-BDNF | yes | GSG | 15 | GSG | T7-His6 | 0.3 |
| pre-pro-BDNF | yes | GSG | 15 | GSG | His6 | 0.3 |
| pre-pro-BDNF | yes | GSG | 16 | no | His6 | 0.3 |

Further possible glycosylation-tags are AAANGTGGA (one N glycosylation site motif; SEQ ID NO: 17), ANITVNITV (two N-glycosylation site motifs; SEQ ID NO: 18), and NATGADNGTGAS (two N-glycosylation site motifs; SEQ ID NO: 19).

ii) Introduced N-Glycosylation Site Motif(s)

In order to improve the (secretion) yield of BDNF artificial N-glycosylation sites were introduced into the BDNF amino acid sequence. The artificial N-glycosylation site can be introduced e.g. by point mutation to the BDNF amino acid sequence (N-glycosylation-site motif: Asn-Xxx-Ser/Thr Xxx any amino acid except Pro). The corresponding encoding nucleic acid sequences were prepared and transiently expressed in HEK293 cells. The numbering of the mutations is based on the amino acid sequence of mature BDNF (SEQ ID NO: 25). The secreted BDNF variants were analyzed for expression/secretion level, degree of N-glycosylation (deduced from migration as band with approx. 3-5 kDa per introduced and used N-glycosylation site increased MW (when compared with the non-glycosylated BDNF reference) by immunoblotting analysis), and functionality/receptor binding via a CHO-TrkB-luciferase reporter gene assay. The results are shown in the following tables (expression yield and biological activities normalized to concentration of maturated BDNF) and FIG. 3.

TABLE 6

| BDNF molecule | deletion of RGR at the C-terminus | linker peptide | purification-tag | mutation in mature BDNF | normalized secreted fusion polypeptide [μg/ml] | BDNF activity in TrkBluciferase assay, EC50 [nM] | degree of glycosylation | lane in FIG. 3 |
|---|---|---|---|---|---|---|---|---|
| pre-pro-BDNF | yes | GSG | T7-His6 | none | 6 | 3.4 | – | 2 |
| pre-pro-BDNF | yes | GSG | T7-His6 | M61T | 8.3 | n.d. | – | 3 |
| pre-pro-BDNF | yes | GSG | T7-His6 | Q79S | 9.6 | 6.9 | – | 4 |
| pre-pro-BDNF | yes | GSG | T7-His6 | R81N | 12.5 | 0.8 | ++ | 5 | n.d.: not determined
–: no glycosylation
+: partial glycosylation
++: full glycosylation

TABLE 7

| BDNF molecule | deletion of RGR at the C-terminus | linker peptide | purification-tag | mutation in mature BDNF | normalized secreted fusion polypeptide [μg/ml] | BDNF activity in TrkBluciferase assay | degree of glycosylation |
|---|---|---|---|---|---|---|---|
| pre-pro-BDNF | yes | GSG | T7-His6 | none | 1.7 | | |
| pre-pro-BDNF | yes | GSG | T7-His6 | W19N | n.d. | n.d. | – |
| pre-pro-BDNF | yes | GSG | T7-His6 | K25N | 6.9 | active | ++ |
| pre-pro-BDNF | yes | GSG | T7-His6 | D30N | n.d. | n.d. | – |
| pre-pro-BDNF | yes | GSG | T7-His6 | G33N | 7.4 | inactive | ++ |

TABLE 7-continued

| BDNF molecule | deletion of RGR at the C-terminus | linker peptide | purification-tag | mutation in mature BDNF | normalized secreted fusion polypeptide [µg/ml] | BDNF activity in TrkBluciferase assay | degree of glycosylation |
|---|---|---|---|---|---|---|---|
| pre-pro-BDNF | yes | GSG | T7-His6 | T35N | 14.9 | active | ++ |
| pre-pro-BDNF | yes | GSG | T7-His6 | P43N | n.d. | n.d. | − |
| pre-pro-BDNF | yes | GSG | T7-His6 | P43N, V42G | n.d. | n.d. | − |
| pre-pro-BDNF | yes | GSG | T7-His6 | M61S, P60G | 2.2 | n.d. | − |
| pre-pro-BDNF | yes | GSG | T7-His6 | G62N, Y63G | 8.8 | active | ++ |
| pre-pro-BDNF | yes | GSG | T7-His6 | Q79T | 8.4 | active | + |
| pre-pro-BDNF | yes | GSG | T7-His6 | W76N | 2.6 | n.d. | − |
| pre-pro-BDNF | yes | GSG | T7-His6 | M92N | n.d. | n.d. | − |
| pre-pro-BDNF | yes | GSG | T7-His6 | D106N | 1.4 | n.d. | − |
| pre-pro-BDNF | yes | GSG | T7-His6 | T112N | 2.6 | inactive | + | n.d.: not determined
−: no glycosylation
+: partial glycosylation
++: full glycosylation
active; BDNF activity comparable to the activity of non-glycosylated mature wild-type BDNF expressed in E. coli, refolded and purified
Inactive: no activity determined The functionality/biological activity of glycosylated BDNF variants was also shown in a dorsal root ganglion (DRG) assay. The activity determined in the DRG assay was comparable to non-glycosylated wild-type BDNF.

II. Improved Expression by Modification of Enzymatic Cleavage Sites

Often secreted polypeptides are synthesized as pre-pro-polypeptides. The pre-segment represents a so called signal sequence. The pro-segment can be e.g. required for protein folding, cellular targeting/transport to a specific cellular compartment (e.g. to lysosomes), or inactivation of the mature protein during transport and storage within a cell or extracellular transport (e.g. secretion into the culture medium). The pre- and pro-segments are not necessary for the biological activity of the mature polypeptide. If the pro-segment is not processed correctly, i.e. the (pre-)pro-segment is not cleaved from the mature protein e.g. in the producing/secreting cell, it can alter the biophysical, biochemical and/or biologic activities of the mature polypeptide.

The method reported below is suitable for polypeptides that are produced in vivo from a pro-polypeptide by enzymatic cleavage.

One aspect as reported herein is a method for producing a recombinant polypeptide from a pro-polypeptide using a variant pro-polypeptide comprising the following steps:
cultivating a mammalian cell comprising a nucleic acid encoding the pro-polypeptide (fusion-polypeptide of a pro-segment and the polypeptide) wherein the endogenous enzymatic cleavage site between the pro-segment and the polypeptide has been replaced by an exogenous protease cleavage site,
recovering the recombinant variant pro-polypeptide from the cell or the cultivation medium, cleaving the pro-polypeptide, and thereby producing the recombinant polypeptide.

One aspect as reported herein is a method for producing a fusion-polypeptide from a pro-fusion-polypeptide comprising the following steps:
cultivating a mammalian cell comprising a nucleic acid encoding a variant pro-fusion-polypeptide wherein the amino acid sequence of the pro-fusion-polypeptide has been modified by replacing in the native pro-fusion-polypeptide the endogenous protease cleavage site between the pro-segment and the fusion-polypeptide with an exogenous (with respect to the origin(s) of the parts of the fusion-polypeptide) or artificial protease cleavage site,
recovering the pro-fusion-polypeptide from the cell or the cultivation medium, cleaving the pro-fusion-polypeptide, and thereby producing the (recombinant) fusion-polypeptide.

In one aspect as reported herein the protease cleavage site between the pro-segment and the mature polypeptide in a pro-polypeptide is replaced by an exogenous (with respect to the origin of the polypeptide or the parts of the fusion-polypeptide) or artificial protease cleavage site.

The term "endogenous protease cleavage site" as used in this context denotes a protease cleavage site that is found in nature between the pro-segment and the mature polypeptide.

The term "exogenous protease cleavage site" as used in this context denotes a protease cleavage site that is not naturally found between the pro-segment and the mature polypeptide.

By the change from the endogenous protease cleavage site to an exogenous protease cleavage site the processing and cleaving of the secreted pro-polypeptide into its mature form can be improved.

The exogenous protease cleavage site can be from any protease as long as the protease is not present/expressed in the cell from which the pro-polypeptide originates, i.e. in which the pro-polypeptide occurs in nature (either in part or totally).

The exogenous protease cleavage site (with respect to the origin of the polypeptide) can be any exogenous protease cleavage site, such as e.g. an IgA protease cleavage site, a TEV protease cleavage site (Tobacco Etch Virus), a Granzyme B cleavage site, a Thrombin cleavage site, a factor 10 cleavage site, an Enterokinase cleavage site, a subtilisin cleavage site, a cathepsin cleavage site, a metallo proteinase cleavage site, an IDES protease cleavage site, a PreScission protease cleavage site, or functional variants thereof.

The cleavage of the pro-polypeptide can occur at different points in time during the recombinant production of the polypeptide.

The cleavage of the pro-polypeptide can be in the cultivation medium. Herein the exogenous protease (effecting the cleavage of the pro-polypeptide) is added to the cultivation medium or the exogenous protease (effecting the cleavage of the pro-polypeptide) is co-expressed in the cultivation medium.

It is also possible to cleave the pro-polypeptide after its separation from the cells, e.g. before, during or after downstream processing (but after cultivation).

In one preferred embodiment the exogenous protease cleavage site is from a different organism than the pro-polypeptide and the recombinant cell expressing the pro-polypeptide. This has the advantage that the point of the processing of the pro-polypeptide can be defined. If the cell expressing the variant pro-polypeptide does not co-express the exogenous protease and the exogenous protease is not added to the cultivation medium the cleavage can no longer be effected by the cell expressing the variant pro-polypeptide or during the cultivation, respectively.

In one embodiment the cleaving of the pro-polypeptide is during the purification.

In one embodiment the cleaving of the pro-polypeptide is on-column during the purification process. In one specific embodiment the column is an affinity column.

In one preferred embodiment the cleaving of the pro-polypeptide is by incubating the pro-polypeptide with the protease after the pro-polypeptide has been separated from the cultivation medium. In one embodiment the incubating is after a first (chromatographic) purification step. In one embodiment the incubating is done on column.

This technique also allows, e.g., the inclusion of an artificial purification tag, such as e.g. a His6-tag, a myc-tag, a HA-tag, or a biotin/avidin-tag, within the pro-segment for improved/simplified purification.

In one embodiment the pro-polypeptide comprises a pro-segment and a mature polypeptide wherein the pro-segment comprises a purification tag. In one embodiment the purification tag is selected from the group of purification tags comprising the His6-tag, the myc-tag, the HA-tag, and the biotin/avidin-tag.

In one embodiment the cleavage of the pro-polypeptide comprising a purification tag is after a purification step using the purification tag.

In any case the cleavage of the pro-segment from the mature polypeptide is made prior to the administration of the mature polypeptide to a patient. In one embodiment the cleavage is made in vitro.

In one preferred embodiment the endogenous protease cleavage site is an IgA protease cleavage site and the purification tag is a hexahistidine (His6) tag. In one embodiment the hexahistidine tag is conjugated via a GSG peptide to the protease cleavage site.

Example: Pre-Pro-BDNF Variant with Exogenous Protease Cleavage Site within the BDNF Pro-Polypeptide An exemplary polypeptide that is expressed as (pre-)pro-polypeptide and cleaved into the mature form is BDNF.

Wild-type human BDNF was expressed in HEK293 cells. During polypeptide processing (i.e. during the expression/recombinant production) the pro-segment was only partially removed by the host cell's proteases resulting in a mixture of mature BDNF and non-processed pro-BDNF. Human pro-BDNF is processed during secretion within the host cell mainly by the secretory pro-protein convertase furin.

A pro-BDNF variant was engineered wherein the naturally occurring furin protease cleavage site was replaced by an exogenous IgA protease cleavage site. IgA protease recognizes and cleaves proteins containing the amino acid sequence N-X-Z-Pro-Pro/-Y-Pro-C (X=preferably Pro or Ser, Y=Thr, Ser, or Ala; Z=preferably Arg or Thr). The amino acid sequence of the pro-BDNF polypeptide contains a furin cleavage site (RVRR; SEQ ID NO: 21). The furin cleavage site was replaced by an IgA protease cleavage site (GSVVAPPAP; SEQ ID NO: 22). Additionally a His6-tag was fused via a GSG linker peptide to the C-terminus of BDNF (HHHHHH; used for affinity purification; SEQ ID NO: 23). Further a potential protease cleavage site was removed (deletion of C-terminal amino acid sequence RGR; SEQ ID NO: 24). In comparative variants an R54A mutation was introduced into the pro-polypeptide of BDNF (the pre-pro-BDNF polypeptide has at amino acid position 54 the amino acid residue Ala instead of Arg), and/or a T7-His6-tag was used instead of the His6-tag. The results are shown in the following table (biological activities normalized to concentration of maturated BDNF).

TABLE 8

| BDNF molecule | deletion of RGR at the C-terminus | linker peptide | purification-tag | mutation in pre-pro-BDNF | protease cleavage site | normalized secreted fusion polypeptide [µg/ml] | BDNF activity in TrkBluciferase assay, EC50 [nM] |
| --- | --- | --- | --- | --- | --- | --- | --- |
| pre-pro-BDNF | yes | GSG | T7-His6 | none | furin | 6 | 3.4 |
| pre-pro-BDNF | yes | GSG | His6 | R54A | furin | 7.8 | 1.2 |
| pre-pro-BDNF | yes | GSG | His6 | none | IgA | 11 | 9.6 |

The numbering of the R54A mutation is based on the amino acid sequence of wild-type pre-pro-BDNF (SEQ ID NO: 20).

The engineered pre-pro-BDNF polypeptide was expressed in HEK293 cells with high yield. The secreted engineered pro-BDNF polypeptide was efficiently converted in vitro into mature native BDNF by cleavage with IgA protease.

Thus, in contrast to the expression of the native pre-pro-BDNF polypeptide comprising the natural furin/PC convertase cleavage site the engineered pro-BDNF polypeptide comprising an exogenous IgA protease cleavage site was obtained as a single expression product. Additionally, improved expression yields were obtained. Further, the mature BDNF polypeptide obtained from the engineered pro-BDNF polypeptide has improved biological activity as the mature BDNF polypeptide obtained from wild-type pre-pro-BDNF in a TrkB luciferase reporter cell assay.

Example: Pre-Pro-BDNF Variant with Exogenous Protease Cleavage Site and Engineered Purification Tag within the BDNF Pro-Polypeptide Affinity tags are very useful for simple and efficient purification of recombinantly produced polypeptides. However, artificial purification tags which remain in the final therapeutic protein are not acceptable for clinical use due to several reasons including potential immunogenicity, changes in biophysical and biochemical properties as well as biologic activities. In order to overcome these limitations a removable purification tag is beneficial.

In one embodiment the (BDNF) pro-polypeptide comprises a purification tag.

A pro-BDNF variant was engineered wherein a His6-tag was introduced into the pro-polypeptide. Additionally the naturally occurring furin protease cleavage site was replaced by an exogenous IgA protease cleavage site and/or an R54A mutation was introduced into the pro-polypeptide.

In a comparative variant the His6-tag was fused via a GSG linker peptide to the C-terminus of BDNF. Further, a T7-His6-tag was used instead of the His6-tag. The results are shown in the following table (biological activities normalized to concentration of maturated BDNF) and FIG. 2.

basic isoelectric point), such as e.g. neurotrophins. The lowering (reduction) of the isoelectric point can be achieved by increasing the number of negative charges in the polypeptide, e.g. by the introduction of negatively charged amino acid residues and/or fusion to a negatively charged moiety such as a linker peptide. Alternatively the lowering of the IEP can be achieved by the removal of positive charges from the surface of the polypeptide, e.g. by the introduction of negatively charged amino acid residues at the surface of the polypeptide. This can be done e.g. by replacement of one or more basic amino acid residue(s) with neutral hydrophilic amino acid residue(s) and/or acidic amino acid residue(s) or combinations thereof.

TABLE 9

| BDNF molecule | deletion of RGR at the C-terminus | linker peptide | C-terminal purification-tag | mutation in pre-pro-BDNF | protease cleavage site | purification tag in the pro-polypeptide | normalized secreted fusion polypeptide [µg/ml] | BDNF activity in TrkBluciferase assay, EC50 [nM] |
|---|---|---|---|---|---|---|---|---|
| pre-pro-BDNF | yes | GSG | T7-His6 | none | furin | none | 6 | 3.4 |
| pre-pro-BDNF | yes | GSG | His6 | R54A | IgA | none | 11.2 | 9.6 |
| pre-pro-BDNF | yes | GSG | His6 | R54A | furin | none | 7.8 | 1.2 |
| pre-pro-BDNF | yes | none | none | R54A | furin | His6 | 7.1 | 1.2 |
| pre-pro-BDNF | yes | none | none | R54A | IgA | His6 | 8.1 | 9.6 |

The biologic activity/functionality of the BDNF polypeptides obtained from the different pro-BDNF variant polypeptides was confirmed using in vitro and in vivo assays. The IgA protease cleavage site containing constructs show improved activity.

The removable purification tag (e.g. such as a hexahistidine-tag) inserted within the N-terminal region of the pro-peptide can be used for efficient purification and will be cleaved off during in vitro protein maturation. Thereby, no potential immunogenic peptide sequences will be retained in the mature polypeptide which will be used for in vivo administration.

III. Improved Expression by Lowering Isoelectric Point

Some polypeptides, e.g. neurotrophins, with a basic isoelectric point (IEP), i.e. an isoelectric point above 9, tend to form aggregates.

In one aspect as reported herein the lowering of the isoelectric point of a polypeptide is used to increase the yield of the recombinantly produced polypeptide using mammalian cells. This method is especially suited for polypeptides that have an isoelectric point above 9 (high isoelectric point, Example: BDNF Variants with Lowered Isoelectric Point BDNF has an isoelectric point of about 10 and is a sticky basic/alkaline molecule (see e.g. Leibrock, J., et al., Nature 341 (1989), 149-152).

In order to improve the (secretion) yield BDNF variants were engineered in which amino acid residues were changed in order to lower the isoelectric point of the molecule. Additionally a T7-His6-tag was fused via a GSG linker peptide to the C-terminus of BDNF. Further in one comparative variant a potential protease cleavage site was removed (deletion of C-terminal amino acid sequence RGR; SEQ ID NO: 23). In a first variant the following amino acid mutations were introduced: P60E, K65D, K73D, and K95A. In a second variant the following amino acid mutations were introduced: K65D, K73D, K95A, and R97A. The IEP values have been calculated using the EMBOSS IEP method (Alan Bleasby (ajb® ebi.ac.uk); European Bioinformatics Institute, Wellconme Trust Genome Campus, Hinxton, Cambridge CB10 1SD, UK). The results are shown in the following table (biological activities normalized to concentration of maturated BDNF).

TABLE 10

| BDNF molecule | deletion of RGR at the C-terminus | linker peptide | C-terminal purification-tag | mutation in mature BDNF | isoelectric point | normalized secreted fusion polypeptide [µg/ml] | BDNF activity in TrkBluciferase assay, EC50 [nM] |
|---|---|---|---|---|---|---|---|
| pre-pro-BDNF | no | GSG | T7-His6 | none | 10.8 | 3-5 | 3 |
| pre-pro-BDNF | yes | GSG | T7-His6 | none | 10.6 | 3-5 | 3 |
| pre-pro-BDNF | yes | GSG | T7-His6 | P60E, K65D, K73D, K95A | 9.5 | 8-9 | 4-5 |
| pre-pro-BDNF | yes | GSG | T7-His6 | K65D, K73D, K95A, | 9.5 | 8-9 | 4-5 |

TABLE 10-continued

| BDNF molecule | deletion of RGR at the C-terminus | linker peptide | C-terminal purification-tag | mutation in mature BDNF | isoelectric point | normalized secreted fusion polypeptide [µg/ml] | BDNF activity in TrkBluciferase assay, EC50 [nM] |
|---|---|---|---|---|---|---|---|
| pre-pro-BDNF | yes | GSG | myc-His6 | R97A none | 10.1 | >22* | 0.36 |

*exceeded linear range of quantification

In contrast to wild-type BDNF the engineered BDNF variants with a lowered IEP stably accumulated over 3 to 6 days in the cell culture medium/supernatant in transiently transfected HEK293 cells. This was also shown by a cell culturing study wherein purified mature BDNF (produced in E. coli) and a purified IEP-lowered myc-tagged BDNF variant was added to a growing HEK293 host cell culture (BDNF concentration 10 µg/ml). After 4 days of cell culturing the remaining BDNF concentration in the cell culture supernatant was determined by reduced SDS PAGE and Western Blot analysis: mature BDNF was completely cleared from the cell culture supernatant after 4 days, whereas the myc-tagged BDNF variant was almost completely stable (see FIG. 1).

IV. Improved Expression by Combination of Different Modifications

In one aspect as reported herein one or more of the following modifications have been made/introduced to improve the recombinant production of a polypeptide:
  i) introduction of one or more glycosylation sites, and/or
  ii) replacement of an endogenous protease cleavage site between the pro-segment and the mature polypeptide with an exogenous (with respect to the origin of the polypeptide) or artificial protease cleavage site, and/or
  iii) lowering of the isoelectric point of the polypeptide, and/or
  iv) by adjusting linker peptide length, connectivity and charge.

To further improve the recombinant production of a polypeptide in certain embodiments any two, any three, or all four modifications as described above are used in combination.

Example: Neurotrophic Proteins

An exemplary neurotrophic protein is brain-derived neurotropic factor (BDNF).

In the amino acid sequence of BDNF two or more of the following modifications have been made:
  introduction of one or more artificial N-glycosylation sites,
  introduction of an opsin-tag as an N-glycosylation-tag, and
  replacement of the endogenous furin cleavage site by an exogenous IgA protease cleavage site.

The results are shown in the following tables (biological activities normalized to concentration of maturated BDNF).

TABLE 11

| BDNF molecule | deletion of RGR at the C-terminus | linker peptide | C-terminal purification-tag | mutation in mature BDNF | protease cleavage site | glycosylation-tag SEQ ID NO: | Lane in FIG. 4 |
|---|---|---|---|---|---|---|---|
| pre-pro-BDNF | yes | GSG | His6 | R81N | IgA | 16 | A |
| pre-pro-BDNF | yes | GSG | myc-His6 | R81N | IgA | 16 | B |
| pre-pro-BDNF | yes | GSG | myc-His6 | R81N | IgA | none | C |
| pre-pro-BDNF | yes | GSG | His6 | R81N | IgA | none | D |
| pre-pro-BDNF | yes | GSG | His6 | none | furin | none | E |
| pre-pro-BDNF | yes | GSG | His6 | none | furin | 16 | F |

From FIG. 4 can be seen that the expression/secretion yield of BDNF variant polypeptides containing one or more additional N-glycosylation sites is improved (Lane A, B and F in FIG. 4) in comparison to BDNF variants without an additional N-glycosylation site (Lane C, D and E in FIG. 4).

TABLE 12

| BDNF molecule | deletion of RGR at the C-terminus | linker peptide | C-terminal purification-tag | mutation in mature BDNF | protease cleavage site | glycosylation-tag SEQ ID NO: | normalized secreted fusion polypeptide [µg/ml] | BDNF activity in TrkBluciferase assay, EC50 [% or nM] |
|---|---|---|---|---|---|---|---|---|
| pre-pro-BDNF | yes | GSG | T7-His6 | none | furin | none | 6 | 100% |
| pre-pro-BDNF | yes | GSG | His6 | none | IgA | none | 11 | 282% |
| pre-pro-BDNF | yes | GSG | none | R81N | IgA | none | | |
| pre-pro-BDNF | yes | GSG | His6 | R81N | IgA | 16 | | |
| pre-pro-BDNF | yes | GSG | myc-His6 | R81N | IgA | 16 | | |
| pre-pro-BDNF | yes | GSG | myc-His6 | R81N | IgA | none | | |
| pre-pro-BDNF | yes | GSG | His6 | none | IgA | 16 | | |
| pre-pro-BDNF | yes | GSG | His6 | K25N | IgA | 16 | | |
| pre-pro-BDNF | yes | GSG | His6 | T35N | IgA | 16 | | |
| pre-pro-BDNF | yes | GSG | His6 | K25N, T35N | IgA | 16 | | |
| pre-pro-BDNF | yes | GSG | T7-His6 | K25N, T35N, | IgA | none | | |

TABLE 12-continued

| BDNF molecule | deletion of RGR at the C-terminus | linker peptide | C-terminal purification-tag | mutation in mature BDNF | protease cleavage site | glycosylation-tag SEQ ID NO: | normalized secreted fusion polypeptide [µg/ml] | BDNF activity in TrkBluciferase assay, EC50 [% or nM] |
|---|---|---|---|---|---|---|---|---|
| pre-pro-BDNF | yes | GSG | T7-His6 | R81N K25N, T35N, Q79T, R81N | IgA | none | | |
| pre-pro-BDNF | yes | GSG | His6 | G62N, Y63G, | IgA | 16 | | |
| pre-pro-BDNF | yes | GSG | His6 | G62N, Y63G, K25N, T35N | IgA | 16 | | |
| wild-type BDNF (E. coli) | | | | | | | | 0.44 |
| pre-pro-BDNF | yes | GSG | T7-His6 | G62N, Y63G, Q79T | furin | none | | 0.13 |
| pre-pro-BDNF | yes | GSG | T7-His6 | T35N, Q79T | furin | none | | 0.064 |
| pre-pro-BDNF | yes | GSG | T7-His6 | K25N, Q79T | furin | none | | 0.21 |
| pre-pro-BDNF | yes | GSG | T7-His6 | T35N, G62N, Y63G, Q79T | furin | none | | 0.069 |
| pre-pro-BDNF | yes | GSG | T7-His6 | Q79T, R81N | furin | none | | 0.05 |
| pre-pro-BDNF | yes | GSG | T7-His6 | T35N, G62N, Y63G | furin | none | | 0.039 |
| pre-pro-BDNF | yes | GSG | T7-His6 | K25N, G62N, Y63G | furin | none | | 276% |
| pre-pro-BDNF | yes | GSG | T7-His6 | G62N, Y63G, R81A | furin | none | | 203% |
| pre-pro-BDNF | yes | GSG | T7-His6 | K25N, T35N | furin | none | | n.d. |
| pre-pro-BDNF | yes | GSG | His6 | none | furin | 16 | | 555% |
| pre-pro-BDNF | yes | GSG | T7-His6 | K25N, T35N, Q79T | furin | none | | 2828% |

V. Improved Expression of Blood-Brain-Barrier Transported Fusion Polypeptides

Brain penetration of large biotherapeutic drugs is strictly limited by the extensive and impermeable blood-brain barrier (BBB) together with the other cell components in the neurovascular unit (NVU). Many strategies to overcome this obstacle have been tested and one is to utilize transcytosis pathways mediated by endogenous receptors expressed on the brain capillary endothelium. Recombinant proteins such as monoclonal antibodies or polypeptides have been designed against these receptors to enable receptor-mediated delivery of biotherapeutics to the brain.

Biotherapeutics have huge therapeutic potential for treatment of pathology in the central nervous system (CNS). However, their route into the brain is prevented by the BBB. Previous studies have illustrated that a very small percentage (approximately 0.1%) of an IgG injected in the bloodstream is able to penetrate into the CNS compartment (Felgenhauer, Klin. Wschr. 52 (1974) 1158-1164). This will certainly limit any pharmacological effect due to the low concentration within the CNS of the biotherapeutic. Therefore, carriers including antibody fragments which mediate the transport of biotherapeutics like neurotrophic factors into the brain are of high medical need.

Thus, fusion polypeptides comprising an effector entity and a monovalent or bivalent binding entity which binds to a BBB receptor have been developed (see e.g. EP 12182181.3).

In one embodiment the monovalent binding entity is specifically binding to a blood brain barrier receptor or a monovalent antibody fragment specifically binding to a blood brain barrier receptor, preferably selected from scFv, Fv, scFab, Fab, and VHH.

In one embodiment the effector entity is a neurotrophic polypeptide, such as BDNF.

In one embodiment the blood brain receptor is selected from the group consisting of the transferrin receptor, insulin receptor, insulin-like growth factor receptor, low density lipoprotein receptor-related protein 8, low density lipoprotein receptor-related protein 1, and heparin-binding epidermal growth factor-like growth factor.

Example: Fusion-Polypeptides Comprising an Antibody Part and BDNF

Boado et al. (Biotechnol. Bioeng. 97 (2007) 1376-1386) report an antibody-BDNF-fusion-polypeptide wherein the amino terminus of human BDNF is fused to the carboxyl terminus of the heavy chain of a chimeric antibody recognizing the human insulin receptor. However, expression of this fusion polypeptide was not possible as the fusion polypeptide aggregates within the cell.

In general, wild-type BDNF or a BDNF variant can be fused to an antibody polypeptide chain either via its C-terminus or its N-terminus. Since BDNF is only active as a homodimer the engineering of biologically active antibody-BDNF fusion polypeptides requires that both i) folding, maturation and assembly of the BDNF part, and ii) folding and assembly of the antibody polypeptide chains/domains is correct. Thus, different fusion polypeptide formats (complexes) are possible, such as e.g. a complete antibody composed of two heavy and light chains, an antibody Fab fragment composed of a light chain and a heavy chain fragment, a single chain Fab (scFab) or a single chain Fv (scFv) in combination with N- or C-terminal fusion of the BDNF polypeptide. Further the fusion polypeptide complex can comprise two or more different polypeptide chains, such as the combination of e.g. a BDNF-scFv-fusion-polypeptide and a mature (non-fused) BDNF polypeptide, a BDNF-Fab (heavy chain)-fusion-polypeptide and a BDNF-Fab(light chain)-fusion-polypeptide, or a BDNF-Fab(heavy chain)-fusion polypeptide and a Fab(light chain)-fusion-polypeptide and a mature (non-fused) BDNF polypeptide. In addition, the BDNF polypeptide can be fused either directly or via a linker peptide to the respective antibody chain polypeptide. The linker peptides can differ in i) the number of amino acids, ii) the kind of amino acids (e.g. negatively charged and/or hydrophobic amino acids), and iii) the engineered putative posttranslational modification motifs (e.g. N-linked glycosylation site motifs). For example, the BDNF polypeptide can be conjugated to different antibody fragments (e.g. a Fab, a scFab and a scFv) connected via different linker peptides resulting in different biologically active fusion-polypeptides.

One aspect as reported herein is a fusion-polypeptide comprising
- exactly one wild-type BDNF polypeptide, or BDNF variant polypeptide or fragment thereof with BDNF activity,
- an antibody fragment, and
- a linker peptide between the BDNF polypeptide and the antibody fragment.

One aspect as reported herein is a fusion-polypeptide with BDNF activity (e.g. dimeric complex) comprising
- exactly one type of wild-type BDNF polypeptide, or BDNF variant polypeptide or fragment thereof with BDNF activity,
- an antibody fragment, and
- a linker peptide between the BDNF polypeptide and the antibody fragment.

Another aspect as reported herein is a dimeric complex consisting of
- as first component a fusion-polypeptide as reported herein, and
- as second component of a wild-type BDNF polypeptide, or BDNF variant polypeptide, or fragment thereof with BDNF activity.

It has been found that only BDNF-antibody-fusion-formats are expressed and properly assembled in biologically active form in complex with a second not-fused BDNF polypeptide if the format comprises exactly one BDNF polypeptide fused covalently via a linker peptide to an antibody fragment and exactly one not-fused BDNF polypeptide.

Further it has been found that the expression of such constructs can be further improved using a linker peptide comprising one or more negatively charged amino acid residues.

Different fusion polypeptide formats were transiently expressed in HEK293 cells. Analysis was performed using Western Blotting and/or a protein A based High-Performance Liquid Chromatography (HPLC) assay. The results are shown in the following Table (biological activities normalized to concentration of maturated BDNF).

TABLE 13

| BDNF molecule | deletion of RGR at the C-terminus | linker peptide | C-terminal purification-tag | mutation in mature BDNF | protease cleavage site | glycosylation-tag SEQ ID NO: |
|---|---|---|---|---|---|---|
| wt-BDNF | no | none | none | none | none | none |
| pp-BDNF | yes | GSG | T7-His6 | none | furin | none |
| pp-BDNF | yes | GSG | His6 | none | furin | 16 |
| pp-BDNF | yes | GSG | His6 | none | IgA | none |
| pp-BDNF | yes | GSG | His6 | R81N | IgA | none |
| pp-BDNF | yes | GSG | T7-His6 | R81N | furin | 16 |
| pp-BDNF | yes | GSG | His6 | none | furin | 16 |
| pp-BDNF | yes | GSG | His6 | none | furin | none |
| pp-BDNF | yes | GSG | His6 | none | furin | none |
| pp-BDNF | yes | GSG | His6 | none | furin | none |
| pp-BDNF | yes | GSG | His6 | none | furin | none |
| pp-BDNF | yes | GSG | His6 | none | furin | none |
| pp-BDNF | yes | GSG | His6 | none | furin | none |
| none-LC | n.a. | n.a. | none | n.a. | n.a. | none |
| pp-BDNF | yes | GSG | T7-His6 | none | furin | none |
| pp-BDNF | yes | GSG | His6 | none | furin | none |
| none-LC | n.a. | n.a. | none | n.a. | n.a. | none |
| pp-BDNF | yes | GSG | His6 | none | furin | none |
| none-LC | n.a. | n.a. | none | n.a. | n.a. | none |
| pp-BDNF | yes | GSG | His6 | none | furin | none |
| none-LC | n.a. | n.a. | none | n.a. | n.a. | none |
| pp-BDNF | yes | GSG | His6 | none | furin | none |
| none-LC | n.a. | n.a. | none | n.a. | n.a. | none |
| pp-BDNF | yes | GSG | T7-His6 | none | furin | none |
| pp-BDNF | yes | GSG | His6 | none | furin | none |
| pp-BDNF | yes | GSG | His6 | none | IgA | 16 |
| none-LC | n.a. | n.a. | none | n.a. | n.a. | none |
| pp-BDNF | yes | GSG | His6 | none | IgA | 16 |
| none-LC | n.a. | n.a. | none | n.a. | n.a. | none |
| pp-BDNF | yes | GSG | T7-His6 | none | IgA | 16 |
| pp-BDNF | yes | GSG | His6 | none | IgA | 16 |
| none-LC | n.a. | n.a. | none | n.a. | n.a. | none |
| pp-BDNF | yes | GSG | His6 | none | IgA | none |
| pp-BDNF | yes | GSG | His6 | none | IgA | 16 |
| none-LC | n.a. | n.a. | none | n.a. | n.a. | none |
| pp-BDNF | yes | GSG | His6 | R81N | IgA | none |
| pp-BDNF | yes | GSG | His6 | R81N | IgA | 16 |
| none-LC | n.a. | n.a. | none | n.a. | n.a. | none |
| pp-BDNF | yes | GSG | His6 | R81N | IgA | 16 |
| none-LC | n.a. | n.a. | none | n.a. | n.a. | none |
| pp-BDNF | yes | GSG | His6 | R81N | IgA | none |
| pp-BDNF | yes | GSG | none | R81N | IgA | 16 |
| none-LC | n.a. | n.a. | none | n.a. | n.a. | none |
| pp-BDNF | yes | GSG | His6 | none | IgA | 16 |

TABLE 13-continued

| | | | | | | |
|---|---|---|---|---|---|---|
| pp-BDNF | yes | GSG | none | R81N | IgA | 16 |
| none-LC | n.a. | n.a. | none | n.a. | n.a. | none |
| pp-BDNF | yes | GSG | His6 | none | IgA | 16 |
| pp-BDNF | yes | GSG | none | R81N | IgA | 16 |
| none-LC | n.a. | n.a. | none | n.a. | n.a. | none |
| pp-BDNF | yes | GSG | His6 | R81N | IgA | 16 |
| pp-BDNF | yes | GSG | none | R81N | IgA | 16 |
| none-LC | n.a. | n.a. | none | n.a. | n.a. | none |
| pp-BDNF | yes | GSG | His6 | R81N | IgA | 16 |
| pp-BDNF | yes | GSG | none | R81N | IgA | 16 |
| none-LC | n.a. | n.a. | none | n.a. | n.a. | none |
| pp-BDNF | yes | GSG | His6 | none | furin | none |
| pp-BDNF | yes | GSG | His6 | none | furin | 16 |
| none-LC | n.a. | n.a. | none | n.a. | n.a. | none |
| pp-BDNF | yes | GSG | His6 | none | furin | none |
| pp-BDNF | yes | GSG | His6 | none | IgA | 16 |
| none-LC | n.a. | n.a. | none | n.a. | n.a. | none |
| pp-BDNF | yes | GSG | His6 | R81N | IgA | 16 |
| none-LC | n.a. | n.a. | none | n.a. | n.a. | none |
| pp-BDNF | yes | GSG | His6 | none | furin | none |
| none-LC | n.a. | n.a. | none | n.a. | n.a. | none |
| pp-BDNF | yes | GSG | His6 | none | IgA | 16 |
| none-LC | n.a. | n.a. | none | n.a. | n.a. | none |
| pp-BDNF | yes | GSG | His6 | R81N | IgA | 16 |
| none-LC | n.a. | n.a. | none | n.a. | n.a. | none |
| pp-BDNF | yes | GSG | His6 | R81N | IgA | none |
| none-LC | n.a. | n.a. | none | n.a. | n.a. | none |
| pp-BDNF | yes | GSG | His6 | none | IgA | 16 |
| pp-BDNF | yes | GSG | none | R81N | IgA | none |
| none-LC | n.a. | n.a. | none | n.a. | n.a. | none |
| pp-BDNF | yes | GSG | His6 | R81N | IgA | 16 |
| pp-BDNF | yes | GSG | His6 | R81N | IgA | none |
| none-LC | n.a. | n.a. | none | n.a. | n.a. | none |
| pp-BDNF | yes | GSG | His6 | none | IgA | 16 |
| pp-BDNF | yes | GSG | His6 | R81N | IgA | none |
| none-LC | n.a. | n.a. | none | n.a. | n.a. | none |
| pp-BDNF | yes | GSG | His6 | none | furin | none |
| pp-BDNF | yes | GSG | His6 | none | furin | 16 |
| none-LC | n.a. | n.a. | none | n.a. | n.a. | none |
| pp-BDNF | yes | GSG | His6 | none | IgA | 16 |
| pp-BDNF | yes | GSG | His6 | none | furin | none |
| none-LC | n.a.. | n.a. | none | n.a. | n.a. | none |
| pp-BDNF | yes | GSG | His6 | none | IgA | 16 |
| pp-BDNF | yes | GSG | His6 | none | furin | 16 |
| none-LC | n.a. | n.a. | none | n.a. | n.a. | none |
| pp-BDNF | yes | GSG | His6 | none | furin | none |
| pp-BDNF | yes | GSG | T7-His6 | none | furin | none |
| none-LC | n.a. | n.a. | none | n.a. | n.a. | none |
| pp-BDNF | yes | GSG | His6 | none | IgA | 16 |
| pp-BDNF | yes | GSG | T7-His6 | R81N | furin | none |
| none-LC | n.a. | n.a. | none | n.a. | n.a. | none |
| pp-BDNF | yes | GSG | His6 | none | IgA | 16 |
| pp-BDNF | yes | GSG | His6 | none | IgA | none |
| none-LC | n.a. | n.a. | none | n.a. | n.a. | none |
| pp-BDNF | yes | GSG | His6 | none | IgA | 16 |

| BDNF molecule | fused to antibody | fused to antibody using SEQ ID NO: | normalized relative secreted fusion polypeptide | BDNF activity in TrkB ELISA assay, EC50 [nM] | relative BDNF activity in TrkB luciferase assay, EC50 [%] |
|---|---|---|---|---|---|
| wt-BDNF | none | n.a. | n.a.*<br>100%** | 5.7 | 60% |
| pp-BDNF | none | n.a. | 100% | 8.9 | 100% |
| pp-BDNF | none | n.a. | | | |
| pp-BDNF | none | n.a. | 40% | | |
| pp-BDNF | none | n.a. | 1000% | | |
| pp-BDNF | none | n.a. | 290% | | |
| pp-BDNF | none | n.a. | 200% | n.d. | 10% |
| pp-BDNF | VL(I) | 26 | <1% | (0) | n.d. |
| pp-BDNF | VH(I) | 26 | | | |
| pp-BDNF | VL(I) | 27 | <1% | (0) | n.d. |
| pp-BDNF | VH(I) | 27 | | | |
| pp-BDNF | VL(I) | 28 | 3% | (0) | n.d. |
| pp-BDNF | VH(I) | 28 | | | |
| pp-BDNF | VH(I) | 26 | 20% | 6.1 | 28% |
| none-LC | n.a. | n.a. | | | |
| pp-BDNF | n.a. | n.a. | | | |
| pp-BDNF | VH(I) | 26 | 6% | 17 | n.d. |

TABLE 13-continued

| | | | | | |
|---|---|---|---|---|---|
| none-LC | n.a. | n.a. | | | |
| pp-BDNF | VH(I) | 27 | 5% | 13.5 | n.d. |
| none-LC | n.a. | n.a. | | | |
| pp-BDNF | VH(I) | 28 | 5% | 18.5 | n.d. |
| none-LC | n.a. | n.a. | | | |
| pp-BDNF | VH(I) | 29 | 42% | 12.4 | 28% |
| none-LC | n.a. | n.a. | | | |
| pp-BDNF | n.a. | n.a. | | | |
| pp-BDNF | scFv(I) | 30 | 32% | n.d. | 3215% |
| pp-BDNF | VH(II) | 29 | 800% | n.d. | 200% |
| none-LC | n.a. | n.a. | | | |
| pp-BDNF | VH(II) | 29 | 900% | n.d. | 60% |
| none-LC | n.a. | n.a. | | | |
| pp-BDNF | VH(II) | 29 | | | |
| none-LC | n.a. | n.a. | | | |
| pp-BDNF | n.a. | n.a. | | | |
| pp-BDNF | VH(II) | 29 | 900% | n.d. | 80% |
| none-LC | n.a. | n.a. | | | |
| pp-BDNF | n.a. | n.a. | | | |
| pp-BDNF | VH(II) | 29 | 1000% | n.d. | inactive |
| none-LC | n.a. | n.a. | | | |
| pp-BDNF | VH(II) | 29 | 900% | n.d. | 110% |
| none-LC | n.a. | n.a. | | | |
| pp-BDNF | n.a. | n.a. | 380% | n.d. | |
| none-LC | n.a. | n.a. | | | |
| pp-BDNF | VH(I) | 29 | | | |
| pp-BDNF | n.a. | n.a. | 450% | | |
| none-LC | n.a. | n.a. | | | |
| pp-BDNF | VH(I) | 29 | | | |
| pp-BDNF | n.a. | n.a. | 840% | | |
| none-LC | n.a. | n.a. | | | |
| pp-BDNF | VH(I) | 29 | | | |
| pp-BDNF | n.a. | n.a. | 620% | | |
| none-LC | n.a. | n.a. | | | |
| pp-BDNF | VH(I) | 31 | | | |
| pp-BDNF | n.a. | n.a. | 560% | | |
| none-LC | n.a. | n.a. | | | |
| pp-BDNF | VH(I) | 32 | | | |
| pp-BDNF | n.a. | n.a. | 520% | | |
| none-LC | n.a. | n.a. | | | |
| pp-BDNF | VH(I) | 32 | | | |
| pp-BDNF | VH(I) | 29 | 160% | | |
| none-LC | n.a. | n.a. | | | |
| pp-BDNF | VH(I) | 29 | 460% | | |
| none-LC | n.a. | n.a. | | | |
| pp-BDNF | VH(I) | 32 | 200% | | |
| none-LC | n.a. | n.a. | | | |
| pp-BDNF | VH(I) | 29 | 168% | | |
| none-LC | n.a. | n.a. | | | |
| pp-BDNF | VH(I) | 31 | 0% | | |
| none-LC | n.a. | n.a. | | | |
| pp-BDNF | n.a. | n.a. | 1180% | | |
| none-LC | n.a. | n.a. | | | |
| pp-BDNF | VH(I) | 29 | | | |
| pp-BDNF | n.a. | n.a. | 630% | | |
| none-LC | n.a. | n.a. | | | |
| pp-BDNF | VH(I) | 29 | | | |
| pp-BDNF | n.a. | n.a. | 1110% | | |
| none-LC | n.a. | n.a. | | | |
| pp-BDNF | VH(I) | 29 | | | |
| pp-BDNF | n.a. | n.a. | 870% | | |
| none-LC | n.a. | n.a. | | | |
| pp-BDNF | VH(I) | 32 | | | |
| pp-BDNF | n.a. | n.a. | 790% | | |
| none-LC | n.a. | n.a. | | | |
| pp-BDNF | VH(I) | 29 | | | |
| pp-BDNF | n.a. | n.a. | 770% | | |
| none-LC | n.a. | n.a. | | | |
| pp-BDNF | VH(I) | 29 | | | |
| pp-BDNF | n.a. | n.a. | 1030% | | |
| none-LC | n.a. | n.a. | | | |
| pp-BDNF | VH(I) | 32 | | | |
| pp-BDNF | n.a. | n.a. | 200% | | |
| none-LC | n.a. | n.a. | | | |
| pp-BDNF | VH(I) | 29 | | | |
| pp-BDNF | n.a. | n.a. | 70% | | |
| none-LC | n.a. | n.a. | | | |
| pp-BDNF | VH(I) | 29 | | | |

TABLE 13-continued

| pp-BDNF | n.a. | n.a. | 70% |
|---|---|---|---|
| none-LC | n.a. | n.a. | |
| pp-BDNF | VH(I) | 29 | | pp-BDNF = pre-pro-BDNF
n.a. = not applicable
n.d. = not determined
VL(I) = BDNF fused to the N-terminus of the light chain variable domain of anti-IGF-1R antibody
VH(I) = BDNF fused to the N-terminus of the heavy chain variable domain of anti-IGF-1R Fab antibody fragment
VL(II) = BDNF fused to the N-terminus of the light chain variable domain of anti-TfR antibody (anti-transferrin receptor antibody)
VH(II) = BDNF fused to the N-terminus of the heavy chain variable domain of anti-TfR Fab antibody fragment
none-LC = light chain antibody polypeptide chain without fused BDNF cognate to used heavy chain
scFv = BDNF fused to the N-terminus of the scFv of anti-IGF-1R antibody
*commercial material from Peprotech
**recombinantly produced in E. coli

Figure 1:
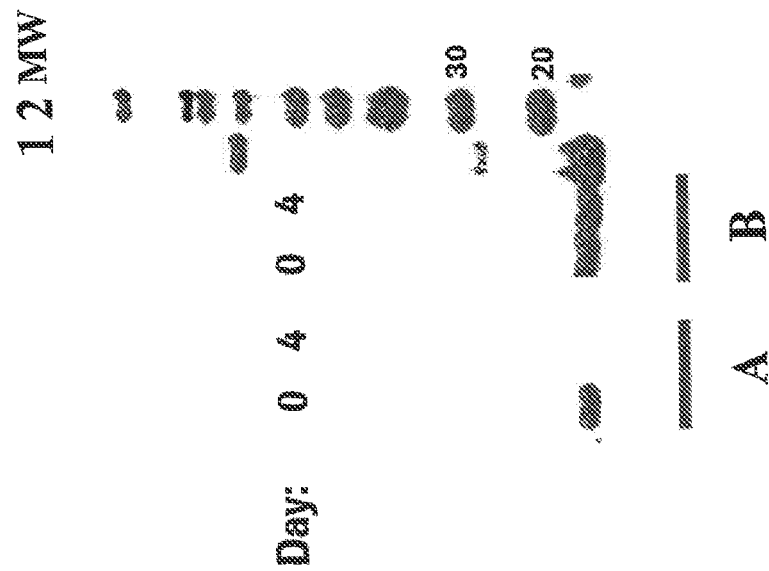
FIG. 1 Stability of BDNF variants during cell culture. Wild-type BDNF (A) produced in E. coli and myc-tagged BDNF produced by transient expression in HEK293 cells (B) were added to a growing culture of HEK293 cells (10 μg/ml) and the BDNF concentration were determined at day 0 and day 4 in samples by reducing SDS PAGE and Western Blot analysis using an anti-BDNF antibody for staining/visualization; lane 1: reference material from Peprotech (E. coli); lane 2: molecular weight marker; the Western Blot has been cut and re-assembled for simplicity.
Figure 2:
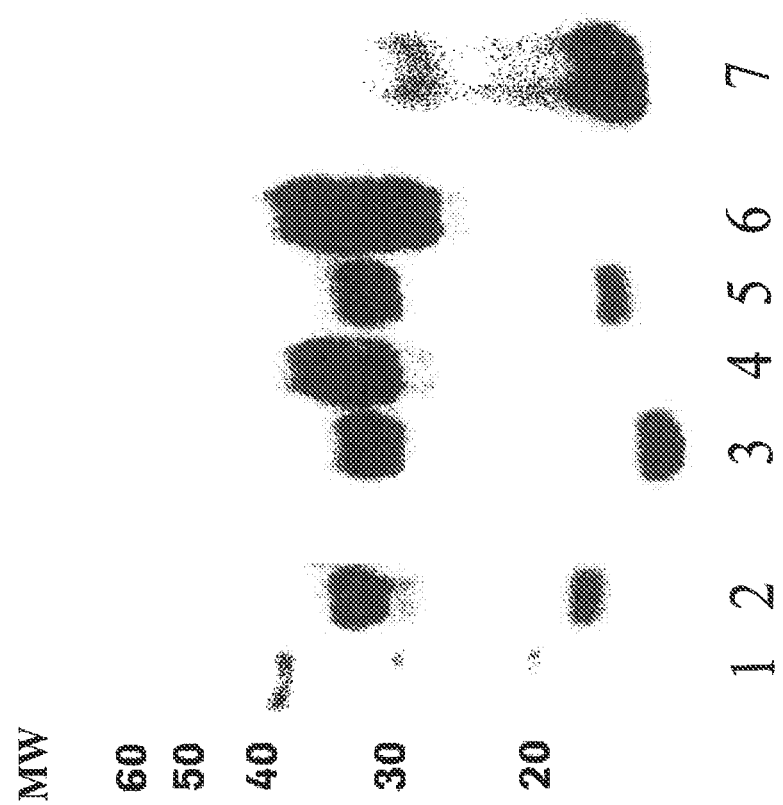
FIG. 2 SDS PAGE/Western Blot analysis of cell culture supernatants containing expressed/secreted BDNF variant polypeptides; lane 1: molecular weight marker; lane 2: row 1 of Table 9; lane 3: row 5 of Table 9; lane 4: row 2 of Table 9; lane 5: row 4 of Table 9; lane 6: row 3 of Table 9; lane 7=mBDNF reference; the Western Blot has been cut an re-assembled for simplicity.
Figure 3:
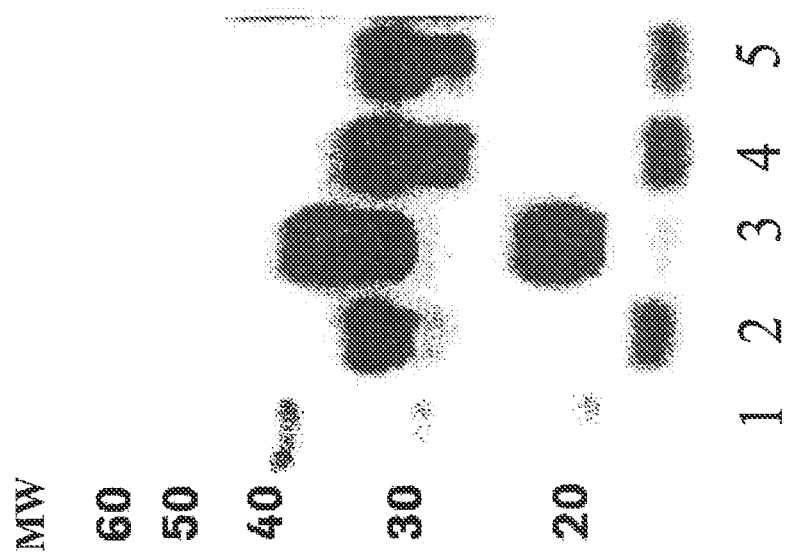
FIG. 3 SDS PAGE/Western Blot analysis of cell culture supernatants containing expressed/secreted BDNF variant polypeptides; lane 1: molecular weight marker, lane 2: row 1 of Table 6 (glycosylated pro-BDNF); lane 3: row 2 of Table 6 (pro-BDNF); lane 4: row 3 of Table 6 (glycosylated mature BDNF); lane 5: row 4 of Table 6 (mature BDNF).
Figure 4:
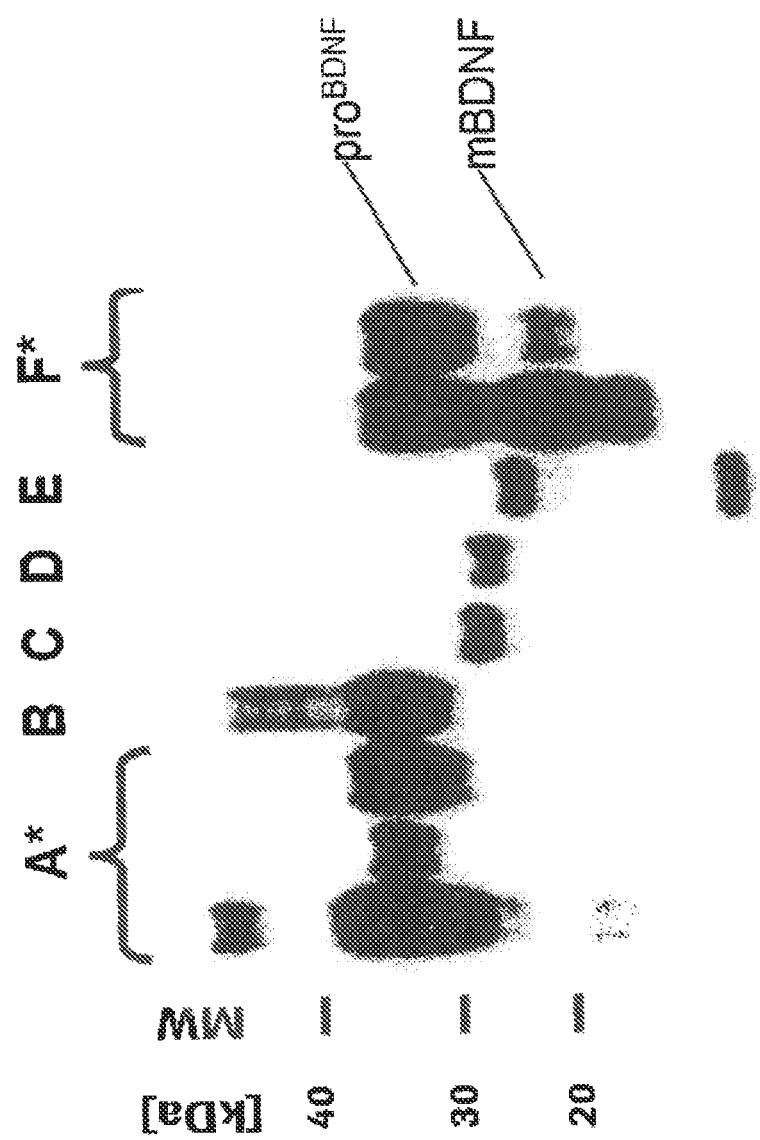
FIG. 4 SDS PAGE/Western Blot analysis of cell culture supernatants containing expressed/secreted BDNF variant polypeptides as of Table 11; lanes A: row 1 of Table 11; lane B: row 2 of Table 11; lane C: row 3 of Table 11; lane D: row 4 of Table 11; lane E: row 5 of Table 11; lanes F: row 6 of Table 11; the star denotes that different expression conditions were used.

The following examples, sequences and figures are provided to aid the understanding of the present invention, the true scope of which is set forth in the appended claims. It is understood that modifications can be made in the procedures set forth without departing from the spirit of the invention.

EXAMPLES

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene Synthesis

Desired genes and gene segments were prepared by chemical synthesis at Geneart GmbH (Regensburg, Germany). The synthesized genes and gene fragments were cloned into an E. coli plasmid for propagation/amplification. The DNA sequence of the subcloned genes and gene fragments were verified by DNA sequencing.

Protein Determination

The protein concentration of purified polypeptides was determined by determining the optical density (OD) at 280 nm, using the molar extinction coefficient calculated on the basis of the amino acid sequence of the polypeptide.

Description of the Basic/Standard Mammalian Expression Plasmid

Desired genes/polypeptides were expressed by transient transfection of human embryonic kidney cells (HEK293). For the expression of a desired gene/polypeptide (e.g. antibody-GFP-fusion-polypeptide, wild-type BDNF, BDNF variant polypeptides, BDNF-Fab- and BDNF-scFv-fusion-polypeptides) a transcription unit comprising the following functional elements was used:

- the immediate early enhancer and promoter from the human cytomegalovirus (HCMV) including intron A,
- a human heavy chain immunoglobulin 5'-untranslated region (5'UTR),
- a gene to be expressed, and
- the bovine growth hormone polyadenylation sequence (BGH pA).

Beside the expression unit/cassette including the desired gene to be expressed the basic/standard mammalian expression plasmid contains

- an origin of replication from the vector pUC18 which allows replication of this plasmid in E. coli, and
- a beta-lactamase gene which confers ampicillin resistance in E. coli.

Example 1

Generation of Antibody Expression Plasmids a) Generation of the Antibody Expression Plasmids for the Parental Human Anti-Human IGF-1R Antibody The gene segments encoding the human kappa light (Vk) and heavy chain variable regions (VH) were joined to the gene segments encoding the human kappa light chain constant region (Ck) or the human gamma-1 heavy chain constant region (CH1-Hinge-CH2-CH3), respectively. Both antibody chain genes were expressed from two separate expression plasmids including the genomic exon-intron structure of the antibody genes. The amino acid sequence of the mature (without signal sequence) heavy and light chain of anti-human IGF-1R antibody are shown in SEQ ID NO: 05 and SEQ ID NO: 06.

The expression of antibody chains is controlled by a shortened intron A-deleted immediate early enhancer and promoter from the human cytomegalovirus (HCMV) including a human heavy chain immunoglobulin 5'-untranslated region (5'-UTR), a murine immunoglobulin heavy chain signal sequence, and the polyadenylation signal from bovine growth hormone (BGH pA). The expression plasmids also contain an origin of replication and a β-lactamase gene from the vector pUC18 for plasmid amplification in *Escherichia coli* (see Kopetzki, E., et al., Virol. J. 5 (2008) 56; Ji, C., et al., J. Biol. Chem. 284 (2009) 5175-5185).

b) Generation of the Anti-Transferrin Receptor Antibody Light Chain Expression Plasmid In order to obtain a light chain for the anti-transferrin-receptor antibody, a light chain gene was chemically synthesized coding for the murine immunoglobulin heavy chain signal sequence MGWSCIILFLVATATGVHS (SEQ ID NO: 14), the VL variable domain of the rat-anti-murine transferrin receptor and the human Vkappa light chain constant region. The amino acid sequence of the VL domain of the rat antibody was obtained from Boado, R. J., et al., Biotechnol. Bioeng. 102 (2009) 1251-1258). The amino acid sequence of the chimeric rat/human anti-transferrin receptor antibody light chain is shown in SEQ ID NO: 80.

Example 2

Generation of Antibody-GFP-Fusion Polypeptide Expression Plasmids a) Generation of the Expression Plasmids for the Anti-IGF-1R Antibody-GFP Fusion-Polypeptides All anti-human IGF-1R antibody heavy chain-GFP-fusion-polypeptide encoding genes were assembled by fusing a chemically synthesized DNA fragment coding for the respective GFP variant and a glycine-serine linker consisting of 2 Gly$_4$Ser repeats and a further Gly (heavy chain . . . LSPG-gggsggggsg-GFP) to the 3' end of the anti-IGF-1R antibody heavy chain gene coding for a slightly truncated human gamma-1 heavy chain constant region (removal of the last natural amino acid Lys). The amino acid sequence of the anti-IGF-1R antibody heavy chain eGFP, emGPF and tagGFP fusion protein is shown in SEQ ID NO: 07, SEQ ID NO: 08 and SEQ ID NO: 09, respectively.

The antibody heavy and light chain genes were expressed from two separate expression plasmids including the genomic exon-intron structure of antibody genes.

b) Generation of Expression Plasmids for Anti-IGF-1R Antibody Heavy Chain-eGFP-Opsin-Tag-Fusion-Polypeptides The expression plasmids for the transient expression of the anti-IGF-1R antibody heavy chain-GFP-opsin-tag-fusion-polypeptides in HEK293 cells was derived from the expression vectors described above. They differ only in the DNA segment encoding the GFP-opsin-tag where upon the 19 amino acid peptide (NGTEGPNFYVPFSNATGVV; opsin(M); SEQ ID NO: 10) was fused directly to the C-terminal end of a respective GFP. As example, the amino acid sequence of the anti-IGF-1R antibody heavy chain-eGFP-opsin(M)-tag-fusion-polypeptide is shown in SEQ ID NO: 33.

Example 3

Generation of BDNF Expression Plasmids a) Generation of the Expression Plasmid for Wild-Type Pre-Pro-BDNF The DNA segment coding for human pre-pro-BDNF gene was prepared by chemical synthesis and inserted into the basic expression vector described above. For this purpose, the pre-pro-BDNF gene was ligated with the CMV-promoter at its 5'-end and with the bovine growth hormone polyadenylation sequence at its 3'-end. The amino acid sequence of the wild type pre-pro-BDNF protein is shown in SEQ ID NO: 20.

b) Generation of the Expression Plasmids for BDNF Variants

In order to obtain optimal production yield several BDNF variants were constructed (see Table below):

in some variants the wild-type BDNF signal sequence (pre-segment) was exchanged by an signal sequence which is derived from a highly expressed murine immunoglobulin heavy chain antibody (MGWSCIIL-FLVATATGVHS);

in some variants the codon usage of the encoding BDNF gene was exchanged to an optimized codon usage in the pro-segment and/or in the mature part of BDNF; the BDNF genes with optimized codon usages were obtained by backtranslation of the amino respective acid sequence using algorithms from Geneart (see e.g. Fath, S., et al., PLOS One 6 (2011) e17596);

in some variants a T7-His6-tag (SEQ ID NO: 12) was used, since it is generally believed to enhance protein expression (see e.g. Luan, C. H., et al., Genome Res. 14 (2004) 2102-2110);

in most BDNF variants a His6-tag was included in order to simplify sample preparation/purification;

in some variants the last three C-terminal amino acids, the RGR motif of mature BDNF, was deleted, since it might function as cryptic protease cleavage site for proteases like furin or other PC convertases;

in another variant the signal sequence and pro-segment of BDNF was exchanged by the corresponding amino acid sequence of human NGF, since it was published that this variation improves expression for another neurotrophin (Iwane et al., Appl. Microbiol. Biotechnol. 41 (1994) 225-232).

TABLE 14

| | use of signal sequence and codon usage | | | | |
|---|---|---|---|---|---|
| BDNF gene/variant (Description of gene/construct features) | pre (BDNF) | pro (BDNF) | mature (BDNF) | tag-1 | tag-2 |
| pre-pro-BDNF-T7-His6 | BDNF | wild-type | wild-type | T7 | His6 |
| pre-pro-BDNF(-RGR)-T7-His6 | BDNF | wild-type | deltaRGR; 1 | T7 | His6 |
| pre-pro-BDNF(-RGR)-His6, codon-optimized | BDNF | wild-type | optimized, deltaRGR | — | His6 |
| pre-pro-BDNF(-RGR)-His6, codon-optimized | BDNF | optimized | optimized, deltaRGR | — | His6 |
| pre(Ab)-pro-BDNF, | antibody; 2 | optimized | optimized | — | — |
| pre-pro-BDNF(-RGR)-His6, codon-optimized | BDNF | optimized | optimized, deltaRGR | — | His6 |

TABLE 14-continued

| | use of signal sequence and codon usage | | | | |
|---|---|---|---|---|---|
| BDNF gene/variant (Description of gene/construct features) | pre (BDNF) | pro (BDNF) | mature (BDNF) | tag-1 | tag-2 |
| pre(Ab)-pro-BDNF | antibody; 2 | optimized | wild-type, optimized | — | His6 |
| pre(NGF)-pro(NGF)-BDNF | NGF; 3 | wild-type; NGF; 3 | wild-type, 1 | — | His6 |

1: C-terminal RGR-motif of BDNF deleted (deltaRGR)
2: signal sequence derived from a highly expressed murine immunoglobulin heavy chain antibody (MGWSCIIL-FLVATATGVHS) as defined by the amino acid sequence shown in SEQ ID NO: 14
3: signal sequence and pro-fragment of BDNF exchanged by corresponding sequence from human NGF c) Generation of the Expression Plasmids for Pre-Pro(IgA)-BDNF and Pre-Pro(IgA; His6) Variants, Partially Including a His6-Tag N-Terminally of Mature BDNF within the Pro-Segment The pre-pro-(IgA)-BDNF gene codes for a pro-polypeptide variant wherein the naturally occurring furin cleavage site (RVRR) was replaced by the engineered IgA protease cleavage site with the sequence GSVVAPPAP (see Table below).

In addition, in some variants a R54A point mutation was introduced into the pro-polypeptide of BDNF to destroy a putative protease cleavage site (see Mowla, S. J., et al., J. Biol. Chem. 276 (2001) 12660-12666). Furthermore, in some variants also a removable His6-tag was included N-terminally of mature BDNF within the pro-fragment. This tag simplifies protein purification of the pro(IgA; His6)-BDNF variant protein. Upon final in vitro protein maturation with IgA protease the pro(IgA; His6 fragment) is removed and, thus, a potential risk of immunogenicity is avoided.

The expression plasmids for the transient expression of the pre-pro(IgA)-BDNF and pre-pro(IgA; His6)-BDNF variant genes/proteins in HEK293 cells are derived from the expression vector described above which encodes for the pre-pro-BDNF(-RGR)-T7-His6 protein. They differentiate in the following characteristics:

d) Generation of the Expression Plasmids for Isoelectric Point Engineered BDNF Variants Previously some in *E. coli* expressed and refolded BDNF variants have been described with an engineered lowered IEP. The pre-pro-BDNF(-RGR)-T7-His6 gene was mutated accordingly and the mutant BDNF genes obtained transiently expressed in HEK293 cells (see Table below). In addition, a myc-tagged BDNF variant was constructed, since (I) the myc-tag (EQKLISEEDL; SEQ ID NO: 90) introduces a net charge difference of about −3 and (2) the myc-tag is of human origin and thus supposed to be less immunogenic.

TABLE 15

| BDNF variant (Description of construct features) | R54A mutation | protease cleavage site | His6-tag | SEQ ID NO: |
|---|---|---|---|---|
| pre-pro-BDNF(-RGR)-T7-His6 | no | furin (wild-type) | C-terminus of BDNF(-RGR) | 35 |
| pre-pro(IgA)-BDNF(-RGR)-His6 | no | IgA | C-terminus of BDNF(-RGR) | 43 |
| pre-pro(His6-R54A-IgA)-BDNF(-RGR) | yes | IgA | within pro(BDNF) | 45 |
| pre-pro(His6-R54A)-BDNF(-RGR) | yes | furin (wild-type) | within pro(BDNF) | 46 |
| pre-pro(R54A)-BDNF(-RGR)-His6 | yes | furin (wild-type) | C-terminus of BDNF(-RGR) | 44 |

The numbering of the R54A mutation is based on the amino acid sequence of wildtype pre-pro-BDNF (SEQ ID NO: 20)

TABLE 16

| BDNF variant (description of construct features) | mutations used for IEP lowering within mature BDNF(deltaRGR) | source of BDNF mutations | tag(s) | calculated IEP of maturated BDNF(deltaRGR) variant | SEQ ID NO: |
|---|---|---|---|---|---|
| pre-pro-BDNF(-RGR)-T7-His6 | none | wild-type BDNF | T7, His6 | 9.58 | 35 |
| pre-pro-BDNF(-RGD; | P60E, K65D, | 53915428| | T7, | 8.15 | 47 |

TABLE 16-continued

| BDNF variant (description of construct features) | mutations used for IEP lowering within mature BDNF(deltaRGR) | source of BDNF mutations | tag(s) | calculated IEP of maturated BDNF(deltaRGR) variant | SEQ ID NO: |
|---|---|---|---|---|---|
| P60E, K65D, K73D, K95A)-T7-His6 | K73D, K95A | gb\|AAU96 862.1\|; sequence 10 of U.S. Pat. No. 6,723,701 | His6 | | |
| pre-pro-BDNF(-RGD; K65D, K73D, K95A, R97A)-T7-His6 | K65D, K73D, K95A, R97A | mBDNF: 5391542\|7 gb\|AAU96 861.1\| sequence 9 of U.S. Pat. No. 6,723,701 | T7, His6 | 8.15 | 48 |
| pre-pro-BDNF(-RGD)-myc-His6 | none | wild-type BDNF | myc, His6 | 8.83 | 49 |

-RGD and (deltaRGR); deletion of the last 3 C-terminal amino acids of mature BDNF;
numbering of amino acid mutations starts at the first amino acid of mature BDNF;
the IEP of the matured BDNF(-RGR) variants were calculated using the protein statistic program pepstats from the European Molecular Biology Open Software Suite (EMBOSS).

e) Generation of the Expression Plasmids for BDNF Variants with Additional Glycosylation Sites BDNF variants were generated which harbor (1) a C-terminal tag containing glycosylation sites or (2) one engineered glycosylation site within the matured BDNF moiety.

The glycosylation tags were deduced from published sequences (e.g. Meder, D., et al., J. Cell Biol. 168 (2005) 303-313; Bulbarelli, A., et al., J. Cell Sci. 115 (2002) 1689-1702; Perlman, S., et al., J. Clin. Endocrinol. Metab. 88 (2003) 3227-3235; WO 2002/002597) and putative N-glycosylation sites were predicted with an artificial neuronal network (NetNglyc server, http://www.cbs.dtu.dk/services/NetNGlyc/).

For introduction of N-glycosylation sites within the maturated BDNF moiety the sequence was inspected for the presence of asparagins, serins or threonins within the matured BDNF sequence. Then, based on the three-dimensional protein structure of human BDNF (1bnd; www.rcsb.org) all non-surface localized Asn, Ser or Thr residues were excluded. For the remaining surface exposed Asn, Ser and Thr residues the adjacent amino acid residues were identified in order to engineer a putative N-glycosylation site (consensus motif: N-X-(S/T), X=any amino acid except Pro) by site-directed mutagenesis. The amino acid position of these putative engineered N-glycosylation sites were used to identify the corresponding amino acids in the structurally and functionally homologous neurotrophins NGF and NT-3 by sequence alignment and protein 3D-structure comparisons. Amino acid positions were excluded that are expected to be part of the neurotrophin::p75NTR or neurotrophin::Trk (A, B) interaction interface based on homologous receptor::ligand crystal structures (e.g. 3buk, 3ij2 and 2ifg). Selected mutations for surface-exposed putative N-glycosylation sites outside the putative BDNF-TrkB/p75 interaction interfaces are mentioned in the Table below (second column).

The expression plasmids for the transient expression of N-glycosylated BDNF variant proteins in HEK293 cells are derived from the expression vector coding for the BDNF variant pre-pro-BDNF(-RGR)-T7-His6 (-RGR: a truncated mature wild-type BDNF wherein the last 3 C-terminal amino acids RGR are deleted; a T7-tag and a His6-tag is attached to the truncated C-terminus of BDNF via a GSG-linker). The BDNF segments, tags, glycolinkers and mutations introduced for the generation of additional artificial N-glycosylation sites are presented in the following table.

TABLE 17

| BDNF variant (description of construct features) | mutations within mature BDNF(deltaRGR) | glycosylation tag SEQ ID NO: | further tags | SEQ ID NO (aa sequence): |
|---|---|---|---|---|
| parental construct, pre-pro-BDNF(-RGR)-T7-His6 | none | none | T7; His6 | 35 |
| pre-pro-BDNF(-RGR)-opsin(S)-T7-His6; | none | 15 | T7; His6 | 36 |
| pre-pro-BDNF(-RGR)-opsin(S)-His6 | none | 15 | His6 | 37 |
| pre-pro-BDNF(-RGR)-opsin(L)-His6 | none | 16 | His6 | 38 |
| pre-pro-BDNF(-RGR)-glyco-1 | none | 18 | His6 | 39 |
| pre-pro-BDNF(-RGR)-glyco-2 | none | 17 | His6 | 40 |
| pre-pro-BDNF(-RGR)-glyco-3 | none | 19 | His6 | 41 |
| pre-pro-BDNF(-RGR; M61T)-T7-His6 | M61T | none | T7; His6 | 42 |
| pre-pro-BDNF(-RGR; Q79S)-T7-His6 | Q79S | none | T7; His6 | 91 |
| pre-pro-BDNF(-RGR; R81N)-T7-His6 | R81N | none | T7; His6 | 89 |
| pre-pro-BDNF(-RGR; W19N)-T7-His6 | W19N | none | T7; His6 | 92 |
| pre-pro-BDNF(-RGR; K25N)-T7-His6 | K25N | none | T7; His6 | 93 |
| pre-pro-BDNF(-RGR; D30N)-T7-His6 | D30N | none | T7; His6 | 94 |
| pre-pro-BDNF(-RGR; G33N)-T7-His6 | G33N | none | T7; His6 | 95 |
| pre-pro-BDNF(-RGR; T35N)-T7-His6 | T35N | none | T7; His6 | 96 |
| pre-pro-BDNF(-RGR; P43N)-T7-His6 | P43N | none | T7; His6 | 97 |
| pre-pro-BDNF(-RGR; P43N, V42G)-T7-His6 | P43N, V42G | none | T7; His6 | 98 |
| pre-pro-BDNF(-RGR; M61S, P60G)-T7-His6 | M61S, P60G | none | T7; His6 | 99 |
| pre-pro-BDNF(-RGR; G62N, Y63G)-T7-His6 | G62N, Y63G | none | T7; His6 | 100 |
| pre-pro-BDNF(-RGR; Q79T)-T7-His6 | Q79T | none | T7; His6 | 101 |
| pre-pro-BDNF(-RGR; W76N)-T7-His6 | W76N | none | T7; His6 | 102 |
| pre-pro-BDNF(-RGR; M92N)-T7-His6 | M92N | none | T7; His6 | 103 |
| pre-pro-BDNF(-RGR; D106N)-T7-His6 | D106N | none | T7; His6 | 104 |
| pre-pro-BDNF(-RGR; T112N)-T7-His6 | T112N | none | T7; His6 | 105 |

SEQ ID NOs for amino acid mutations introduced by site-directed mutagenesis into mature BDNF(deltaRGR) are exemplarily shown for the BDNF variants pre-pro-BDNF(-RGR; M61T)-T7-His6 and pre-pro-BDNF(-RGR; R81N)-T7-His6.

f) Generation of the Expression Plasmids for BDNF Variants Containing Combined Mutations for the Introduction of Multiple (Two or More) N-Glycosylation Sites and an IgA Cleavage Site In order to generate BDNF variants with multiple N-glycosylation sites some of the additional N-glycosylation sites identified in previous experiments were combined. The starting construct pre-pro(IgA)-BDNF(-RGR)-His6 variant polypeptide is characterized by an IgA protease cleavage site instead of the native furin site within the pro-segment, a C-terminally truncated mature BDNF (deletion of the last 3 amino acids RGR) and a C-terminal His6-tag. The desired mutations and tags were introduced/attached as shown in the Table below.

TABLE 18

| BDNF variant (description of construct features) | additional glycosylation sites | | | | | | | SEQ ID NO: |
|---|---|---|---|---|---|---|---|---|
| | opsin(L)-tag | K25N | T35N | G62N, Y63G | Q79T | R81N | myc-tag | |
| parental construct, pre-pro(IgA)-BDNF(-RGR)- | | | | | | | | 43 |

TABLE 18-continued

| BDNF variant (description of construct features) | additional glycosylation sites ||||||| SEQ ID NO: |
|---|---|---|---|---|---|---|---|---|
| | opsin(L)-tag | K25N | T35N | G62N, Y63G | Q79T | R81N | myc-tag | |
| His6 pre-pro(IgA)-BDNF(-RGR; R81N)-opsin(L) | x | | | | | x | | 50 |
| pre-pro(IgA)-BDNF(-RGR; R81N)-His6 | | | | | | x | | 53 |
| pre-pro(IgA)-BDNF(-RGR; R81N)-opsin(L)-myc-His6 | x | | | | | x | x | 51 |
| pre-pro(IgA)-BDNF(-RGR; R81N)-myc-His6 | | | | | | x | x | 52 |
| pre-pro(IgA)-BDNF(-RGR)-opsin(L)-His6 | x | | | | | | | 54 |
| pre-pro(IgA)-BDNF(-RGR; K25N)-opsin(L)-His6 | x | x | | | | | | 55 |
| pre-pro(IgA)-BDNF(-RGR; T35N)-opsin(L)-His6 | x | | x | | | | | 56 |
| pre-pro(IgA)-BDNF(-RGR; K25N, T35N)-opsin(L)-His6 | x | x | x | | | | | 57 |
| pre-pro(IgA)-BDNF(-RGR; K25N, T35N, R81N)-T7-His6 | | x | x | | | x | | 58 |
| pre-pro(IgA)-BDNF(-RGR; K25N, T35N, Q79T, R81N)-T7-His6 | | x | x | | x | x | | 59 |
| pre-pro(IgA)-BDNF(-RGR; G62N, Y63G)-opsin(L)-His6 | x | | | x | | | | 60 |
| pre-pro(IgA)-BDNF(-RGR; G62N, Y63G, K25N, T35N)-opsin(L)-His6 | x | x | x | x | | | | 61 | g) Generation of the Expression Plasmids for BDNF Variants Containing Combined Mutations for the Introduction of Multiple (Two or More) N-Glycosylation Sites In order to generate BDNF variants with multiple N-glycosylation sites some of the additional N-glycosylation sites identified in previous experiments were combined. For this purpose the pre-pro-BDNF(-RGR)-T7-His6 variant protein characterized by a C-terminally truncated mature BDNF (deletion of the last 3 amino acids RGR) and a C-terminal T7-His6-tag was used as starting material. The desired mutations were inserted as shown in the Table below.

TABLE 19

| BDNF variant (description of construct features) | additional glycosylation sites | | | | | SEQ ID NO (aa sequence): |
|---|---|---|---|---|---|---|
| | K25N | T35N | G62N, Y63G | Q79T | R81N | |
| parental construct, pre-pro-BDNF(-RGR)-T7-His6 | | | | | | 35 |
| pre-pro-BDNF(-RGR; G62N, Y63G, Q79T)-T7-His6 | | | x | x | | 62 |
| pre-pro-BDNF(-RGR; | | x | | x | | 63 |

TABLE 19-continued

| BDNF variant (description of construct features) | K25N | T35N | G62N, Y63G | Q79T | R81N | SEQ ID NO (aa sequence): |
|---|---|---|---|---|---|---|
| T35N, Q79T)-T7-His6 | | | | | | |
| pre-pro-BDNF(-RGR; K25N, Q79T)-T7-His6 | x | | | x | | 64 |
| pre-pro-BDNF(-RGR; T35N, G62N, Y63G, Q79T)-T7-His6 | | x | x | x | | 65 |
| pre-pro-BDNF(-RGR; Q79T, R81N)-T7-His6 | | | | x | x | 106 |
| pre-pro-BDNF(-RGR; T35N; G62N; Y63G)-T7-His6 | | x | x | | | 66 |
| pre-pro-BDNF(-RGR; K25N; G62N; Y63G)-T7-His6 | x | | x | | | 67 |
| pre-pro-BDNF(-RGR; K25N; T35N)-T7-His6 | x | x | | | | 68 |
| pre-pro-BDNF(-RGR; G62N, Y63G, R81N)-T7-His6 | | | x | | x | 69 |
| pre-pro-BDNF(-RGR; K25N; T35N; Q79T)-T7- His6 | x | x | | x | | 70 |

Example 4

Generation of BDNF Antibody Fragment Fusion-Polypeptides Expression Plasmids a) Generation of the Expression Plasmids for the BDNF-Fab Antibody Heavy Chain Fusion-Polypeptides In order to obtain BDNF-(Gly$_4$Ser)$_a$-Fab(anti-IGF-1R antibody heavy chain) fusion-polypeptides, plasmids for transient expression in HEK293 cells were constructed which harbored a chemically synthesized DNA fragment of a CDS (coding DNS sequence) coding for polypeptides with the following characteristics:
 the wild-type pre-pro-BDNF moiety deleted for the C-terminal RGR motif is fused at the C-terminus with a glycine-rich linker followed by a Fab heavy chain portion (VH-CH1) of the human anti-IGF-1R antibody and a C-terminal His6-tag;
 the glycine-rich linker consists of a (G4S)2-GG or a (G4S)4-GG or a (G4S)6-GG motif (see Table below).

b) Generation of the Expression Plasmids for the BDNF-Fab Antibody Light Chain Fusion-Polypeptides In order to obtain BDNF-(Gly$_4$Ser)$_n$-Fab fusion-polypeptides, plasmids for transient expression in HEK293 cells were constructed which harbored a chemically synthesized DNA fragment of a CDS coding for polypeptides with the following characteristics:
 the wild-type pre-pro-BDNF moiety deleted for the C-terminal RGR motif is fused at the C-terminus with a glycine-rich linker followed by the Fab VL-Ckappa light chain domains of the human anti-IGF-1R antibody and a C-terminal His6 tag;
 the glycine-rich linker consists of a (G4S)2-GG or a (G4S)4-GG or a (G4S)6-GG motif (see Table above).

TABLE 20

| BDNF-antibody variant, (description of construct features) | linker between BDNF and Fab fragment | Fab fragment (anti-IGF-1R mAB) | Tag | SEQ ID NO (aa sequence): |
|---|---|---|---|---|
| pre-pro-BDNF(-RGD)_(G4S)2GG_VL<IGF-1R>-Ck-His6 | (G$_4$S)$_2$-GG | VL-Ckappa | His6 | 71 |
| pre-pro-BDNF(-RGD)_(G4S)4GG_VL<IGF-1R>-Ck-His6 | (G$_4$S)$_4$-GG | VL-Ckappa | His6 | 72 |
| pre-pro-BDNF(-RGD)_(G4S)6GG_VL<IGF-1R>-Ck-His6 | (G$_4$S)$_6$-GG | VL-Ckappa | His6 | 73 |
| pre-pro-BDNF(-RGD)_(G4S)2GG_VH<IGF-1R>-CH1-His6 | (G$_4$S)$_2$-GG | VH-CH1 | His6 | 74 |
| pre-pro-BDNF(-RGD)_(G4S)4GG_VH<IGF-1R>-CH1-His6 | (G$_4$S)$_4$-GG | VH-CH1 | His6 | 75 |
| pre-pro-BDNF(-RGD)_(G4S)6GG_VH<IGF-1R>-CH1-His6 | (G$_4$S)$_6$-GG | VH-CH1 | His6 | 76 | c) Generation of the Expression Plasmid for the Anti-IGF-1R Antibody Light Chain The native anti-IGF-1R antibody light chain was used for the generation anti-IGF-1R based BDNF-Fab complexes. The generation of the anti-IGF-1R antibody light chain expression plasmid is described in example 1.

d) Generation of the Expression Plasmid for the BDNF-Fab(Anti-IGF-1R Antibody Heavy Chain) Fusion-Polypeptides Containing a Negatively Charged Gly-Asp Linker In order to obtain BDNF-(G3D)4-Fab(anti-IGF-1R antibody heavy chain fusion-polypeptide, a plasmid for transient expression in HEK293 cells was constructed which harbored a chemically synthesized DNA fragment of a CDS coding for the polypeptide with the following characteristics:
 the wild-type pre-pro-BDNF moiety deleted for the C-terminal RGR motif is fused at the C-terminus with a glycine-rich negatively charged linker followed by the Fab VH-CH1 heavy chain domains of the human anti-IGF-1R antibody and a C-terminal His6-tag;
 the glycine-rich negatively charged linker consists of the (G3D)4-GGGS motif.

e) Generation of the Expression Plasmids for the BDNF-Fab(Anti-IGF-1R Antibody Heavy Chain) Fusion Proteins Harboring an IgA Cleavage Site within the Pro-BDNF Segment, a Negatively Charted GlyAsp Linker and Multiple N-Glycosylation Sites In order to obtain pro(IgA)-BDNF-(G3D)4-Fab(anti-IGF-1R antibody heavy chain fusion-polypeptides with multiple N-glycosylation sites, plasmids for transient expression in HEK293 cells were constructed which harbored a chemically synthesized DNA fragment of a CDS which code for polypeptides with the following characteristics:

the pre-pro(IgA)-BDNF moiety deleted for the C-terminal RGR motif of mature BDNF is fused at the C-terminus with the extended opsin-tag (NGTEGPNFYVPFSNATGVVR; opsin(L); SEQ ID NO: 16) followed by a negatively charged glycine-aspartic-acid-rich linker and a Fab heavy chain portion (VH-CH1, partially extended with the hinge-derived peptide EPKSC) of the human monoclonal antibody directed against human insulin-like growth factor 1 (IGF-1R) and a C-terminal His6-tag;

the negatively charged glycine-aspartic-acid-rich linker consists either the (G3D)4-GGGS motif or the (G2D)5-G2SG motif.

The details of the constructs are summarized in the Table below.

In order to obtain pro(IgA)-BDNF-(G3D)4-Fab(anti-TfR) antibody heavy chain fusion-polypeptides with a negatively charged GlyAsp linker and multiple N-glycosylation sites, plasmids for transient expression in HEK293 cells were constructed which harbored a chemically synthesized DNA fragment of a CDS which code for polypeptides with the following characteristics:

the pre-pro(IgA)-BDNF moiety deleted for the C-terminal RGR motif is fused at the C-terminus with the opsin (L)-tag followed by a negatively charged glycine-aspartic-acid-rich linker and a chimeric rat/human Fab heavy chain portion wherein the VH variable domain is derived from the rat 8D3 monoclonal antibody which is directed against the mouse transferrin receptor (mTfR) and wherein the CH1 domain is derived from human IgG and a C-terminal His6-tag; the amino acid sequence of VH domain of the antibody was obtained from Boado, R J., et al., Biotechnol. Bioeng. 102 (2009) 1251-1258);

the negatively charged glycine-aspartic-acid-rich linker consists of the (G3D)4-GGGS motif;

in most variants the endogenous furin/PC convertase cleavage site between the pro-segment and the mature part of BDNF was exchanged by an IgA protease cleavage site (GSVVAPPAP);

TABLE 21

| BDNF-antibody variant, (description of construct features) | His-tag | protease cleavage site | introduced additional N-glycosylation sites | | linker between BDNF and Fab fragment | origin of Fab heavy chain fragment | hinge EPKSC peptide | SEQ ID NO: |
|---|---|---|---|---|---|---|---|---|
| | | | opsin-tag | within BDNF (deltaRGR) | | | | |
| pre-pro(IgA)-BDNF(-RGR)_(G3D)4-G3S_VH<IGF-1R>-CH1-EPKSC-His6 | His6 | IgA | none | | (G3D)4-GGGS | <IGF-1R> | yes | 85 |
| pre-pro(IgA)-BDNF(-RGR; R81N)_opsin(L)-(G3D)4-G3S_VH<IGF-1R>-CH1-His6 | His6 | IgA | opsin(L) | +R81N | GSG--opsin(L)-(G3D)4-GGGS | <IGF-1R> | no | 86 |
| pre-pro(IgA)-BDNF(-RGR)_(G3D)4-G3S_VH<IGF-1R>-CH1-His6 | His6 | IgA | none | | (G3D)4-GGGS | <IGF-1R> | no | 84 |
| pre-pro(IgA)-BDNF(-RGR; R81N)_opsin(L)-(G2D)5-G2SG_VH<IGF-1R>-CH1-His6 | His6 | IgA | opsin(L) | +R81N | GSG-opsin(L)-(G2D)5-G2SG | <IGF-1R> | no | 87 | f) Generation of the Expression Plasmids for the BDNF-Fab(Anti-Transferrin Receptor Antibody Heavy Chain) Fusion-Polypeptides Harboring an IgA Cleavage Site within the Pro-BDNF Segment, a Negatively Charted GlyAsp Linker and Multiple N-Glycosylation Sites in some variants the truncated wild-type mature BDNF moiety (BDNF; deltaRGR) was exchanged by a truncated mature BDNF variant harboring an artificial R209N glycosylation site (BDNF(deltaRGR; R209N)).

The details of the constructs are summarized in the Table below.

TABLE 22

| BDNF-antibody variant, (description of construct features) | His6-tag | protease cleavage site | introduced additional N-glycosylation sites | | linker between BDNF and Fab fragment | origin of Fab heavy chain fragment | hinge EPKSC | SEQ ID NO (aa sequence): |
|---|---|---|---|---|---|---|---|---|
| | | | opsin-tag | BDNF (ΔRGR) moiety | | | | |
| pre-pro(IgA)-BDNF(-RGR)_(G3D)4-G3S_VH<TfR>8D3-CH1- | His6 | IgA | none | none | (G3D)4-GGGS | <TfR>8D3 | yes | 107 |

TABLE 22-continued

| BDNF-antibody variant, (description of construct features) | His6-tag | protease cleavage site | opsin-tag | BDNF (ΔRGR) moiety | linker between BDNF and Fab fragment | origin of Fab heavy chain fragment | hinge EPKSC | SEQ ID NO (aa sequence): |
|---|---|---|---|---|---|---|---|---|
| EPKSC-His6 pre-pro(IgA)-BDNF(-RGR; R81N)_opsin(L)-(G3D)4-G3S_VH<TfR>8D3-CH1-His6 | His6 | IgA | opsin (L) | R81N | GSG-opsin(L)-(G3D)4-GGGS | <TfR>8D3 | no | 81 |
| pre-pro(IgA)-BDNF(-RGR)_(G3D)4-G3S_VH<TfR>8D3-CH1-His6 | His6 | IgA | none | none | (G3D)4-GGGS | <TfR>8D3 | no | 108 |
| pre-pro(IgA)-BDNF(-RGR)_(G3D)4-G3S_VH<TfR>8D3-CH1 | none | IgA | none | None | (G3D)4-GGGS | <TfR>8D3 | No | 109 |
| pre-pro(IgA)-BDNF(-RGR)_opsin(L)-(G3D)4-G3S_VH<TfR>8D3-CH1-His6 | His6 | IgA | opsin (L) | none | GSG-opsin(L)-(G3D)4-GGGS | <TfR>8D3 | No | 79 |

Example 6

Generation of the Expression Plasmid for the BDNF-scFv Fusion-Polypeptides

In order to obtain a BDNF(G4S)3-scFv-anti-IGF-1R antibody heavy chain-fusion-polypeptide, a plasmid for transient expression in HEK293 cells was constructed which harbored a chemically synthesized DNA fragment of a CDS which codes for a polypeptide with the following characteristics:
the wild-type pre-pro-BDNF moiety deleted for the C-terminal RGR motif is fused at the C-terminus with a (G4S)3 linker followed by a scFv moiety of the human anti-human IGF-1R antibody;
the scFv moiety of the anti-human IGF-JR antibody is build up of a VL domain, followed by a (G4S)4-GG linker, a VH region and a His6-tag; the amino acid sequence of the pre-pro-BDNF(-RGR)_(G4S)3_scFv-His6<IGF-1R>fusion protein is shown in SEQ ID NO: 78.

Example 7

Transient Expression, Purification and Analytical Characterization of Polypeptides Transient Expression The polypeptides were generated by transient transfection of HEK293 cells (human embryonic kidney cell line 293-derived) cultivated in F17 Medium (Invitrogen Corp.). For transfection "293-Free" Transfection Reagent (Novagen) was used. The antibody and antibody fragment (Fab and scFv) comprising fusion-polypeptides were expressed from one, two or three different plasmids using an equimolar plasmid ratio upon transfection. Transfections were performed as specified in the manufacturer's instructions. The recombinant polypeptide-containing cell culture supernatants were harvested four to seven days after transfection. Supernatants were stored at reduced temperature until purification.

General information regarding the recombinant expression of human immunoglobulins in e.g. HEK293 cells is given e.g. in Meissner, P., et al., Biotechnol. Bioeng. 75 (2001) 197-203.

Purification a) GFP Fusion-Polypeptides were Purified Using a Two-Step Procedure Including a Protein a Chromatography and a Size Exclusion Chromatography on a Superdex 200™ Column GFP fusion-polypeptide containing culture supernatants were filtered. Thereafter the GFP fusion-polypeptides were captured by affinity chromatography using HiTrap MabSelectSuRe (GE Healthcare) equilibrated with PBS (1 mM $KH_2PO_4$, 10 mM $NaHPO_4$, 137 mM NaCl, 2.7 mM KCl, pH 7.4). Unbound polypeptides were removed by washing with equilibration buffer, and the fusion-polypeptide was recovered with 0.1 M citrate buffer, pH 2.8. Immediately after elution the fractions were neutralized to pH 6.0 with 1 M Tris-base, pH 9.0.

Size exclusion chromatography on Superdex 200™ (GE Healthcare, Uppsala, Sweden) was used as second purification step. The size exclusion chromatography was performed in 50 mM histidine buffer, 0.15 M NaCl, pH 6.8. The recovered GFP fusion-polypeptides were stored at −80° C.

b) Histidine-Tagged Proteins were Purified Using a Two-Step Protocol Starting with an Immobilized Metal Ion Affinity Chromatography (IMAC) and Followed by a Size Exclusion Chromatography on a Superdex 75™ Column The histidine-tagged polypeptide-containing culture supernatants were adjusted with NaCl to a final NaCl concentration of 500 mM. The filtered culture supernatant was loaded onto a Ni-Sepharose™ 6 Fast Flow column pre-equilibrated with a NiA-buffer (50 mM TRIS, 300 mM NaCl, 5 mM imidazole containing an EDTA-free protease inhibitor cocktail tablet as specified in the manufacturer's instructions; EDTA-free Complete Mini Tablets; Roche Applied Science) at a flow of 1 ml/min using an ÄKTA explorer 100 system (GE Healthcare, Uppsala, Sweden). The column was washed with NiA-buffer until the UV reading reached back close to baseline. The histidine-tagged polypeptide was eluted with a 5 mM to 300 mM linear imidazole gradient in 50 mM TRIS and 500 mM NaCl, pH 8.0 in 10 column volumes.

Size exclusion chromatography on Superdex 75™ (GE Healthcare, Uppsala, Sweden) was used as second purification step. The size exclusion chromatography was performed in 50 mM histidine buffer, 0.15 M NaCl, pH 6.8. The eluted histidine-tagged proteins were stored at −80° C.

Analytical Characterization

The protein concentrations of the purified polypeptides were determined by measuring the optical density (OD) at 280 nm, using the molar extinction coefficient calculated on the basis of the amino acid sequence. Purity and proper dimer formation of polypeptides were analyzed by SDS-PAGE in the presence and absence of a reducing agent (5 mM 1,4-dithiothreitol) and staining with Coomassie brilliant blue. Aggregate content of the Fc-fusion-polypeptide preparations was determined by high-performance SEC using a Superdex 200™ analytical size-exclusion column (GE Healthcare, Uppsala, Sweden). The integrity of the amino acid backbone of reduced polypeptides was verified by Nano Electrospray QTOF mass spectrometry after removal of N-glycans by enzymatic treatment with a combination of neuraminidase, O-glycanase and peptide-N-glycosidase F (Roche Applied Science, Mannheim, Germany).

Determination of the BDNF Concentration in Culture Supernatant

The concentration of wild-type BDNF, BDNF variants and BDNF containing fusion-polypeptides in culture supernatants was determined by semi-quantitative Western Blot analysis using recombinant human BDNF from Peprotech (catalog number: 450-02) as reference standard. A rabbit anti-BDNF antibody (Santa Cruz; catalog number: sc-20981) (first antibody) and a horseradish peroxidase conjugated sheep anti-rabbit antisera (diluted 1:5000, Roche Diagnostics GmbH, Germany) (secondary antibody) and enhanced chemiluminescence substrate (LUMI-Light plus Western Blotting substrate, Roche Diagnostics GmbH, Germany) was used for staining.

The concentration of BDNF fusion-polypeptides was also determined with a BDNF ELISA using the BDNF Emax® ImmunoAssay Kit from Promega (catalog number: G7610) according to the instructions of the supplier.

Example 8

In Vitro Functional Characterization

Determination of the Biological Activity of Wild-Type GFP and GFP-Containing Fusion-Polypeptides The biological activity of purified wild-type GFP and GFP-containing fusion-polypeptides was monitored by its bioluminescent properties (GFP-specific fluorescence).

Determination of the BDNF Binding Affinity Via Surface Plasmon Resonance (SPR, BIAcore)

Amine coupling of around 750 resonance units (RU) of a capturing system (capturing mAb specific for human IgG, Jackson Immunoresearch) was performed on a CM5 chip at pH 4.5 using an amine coupling kit according to the manufacturer's manual (supplied by GE Healthcare, Uppsala, Sweden). Human Fc-tagged TrkB (R&D Systems, catalog number: 688-TK-100) was captured at a concentration of 5 µg/ml. Excess binding sites were blocked by injecting a human Fc mixture at a concentration of 1.25 µM (Biodesign, catalog number: 50175). Different concentrations of BDNF containing fusion-polypeptides ranging from 0.1 nM to 50 nM were passed with a flow rate of 10 µL/min through the flow cells at 298 K for 120 to 240 sec. The dissociation phase was monitored for up to 600 sec and triggered by switching from the sample solution to running buffer. The surface was regenerated by 1 min washing with a 100 mM phosphoric acid solution at a flow rate of 30 L/min. For all experiments HBS-P+ buffer supplied by GE Healthcare was chosen (10 mM HEPES ((4-(2-hydroxyethyl)-1-piperazine ethanesulfonic acid)), pH 7.4, 150 mM NaCl, 0.05% (v/v) Surfactant P20).

Bulk refractive index differences were corrected for by subtracting the response obtained from a blank-coupled surface. Blank injections are also subtracted (double referencing).

The equilibrium dissociation constant (Kd), defined as ka/kd, was determined by analyzing the sensorgram curves obtained with several different concentrations, using BIAevaluation 4.1 software package. The fitting of the data followed a suitable binding model.

Determination of the BDNF Binding Affinity Via ELISA

The binding properties of BDNF-containing fusion proteins were determined with a TrkB ELISA. Maxisorb plates were coated with 1 µg/mL of a TrkB-Fc fusion (R&D Systems) in PBS overnight at 4° C. After blocking the plate with PBSTC (PBS with 0.05% Tween-20 and 2% Chicken serum (Gibco)) for 1 h at RT and three washes with PBST, BDNF-containing fusion proteins or BDNF alone were added to the wells at concentrations of 15 to 500 ng/mL in PBSTC and incubated for 2 h at RT. After six washes, the wells were incubated with mouse-anti-BDNF antibody (clone 4F11.1A1, 1 µg/mL in PBSTC) and, after further washes, with anti-mouse-HRP antibody (1:10000 in PBSTC), both for 1 h at RT. After three washes with PBST, HRP activity was detected using ABTS substrate and photometric quantification at a wavelength of 492 nm.

Determination of the Biological Activity of BDNF Containing Fusion Proteins Via a TrkB Reporter Gene Assay The biological activity of BDNF variants and BDNF-containing fusion proteins was determined with a TrkB-transfected CHO cell line containing a stably transfected luciferase reporter gene under the control of a SRE (serum-response element)-containing-promoter (CHO-K1-hTrkB/pSRE-Luc). The day before the experiments cell medium was changed from growth medium (Ham's F12 containing 10% FCS, 2 mM L-glutamine, 300 µg/mL G418 and 3 µg/mL puromycin) to the same medium without FCS for starvation. The next day, $10^5$ cells were seeded per well of a 96-well plate in 50 µL medium, then BDNF fusion proteins were added at concentrations between 0.02 nM and 115 nM, in 50 µL medium. After incubation for 4 h at 37° C., 7.5% $CO_2$, cells were equilibrated for 30 min at RT and 100 µL of BrightGlo Luciferase Assay reagent (Promega) was added per well. Luminescence was read out after 5 minutes incubation using a Tecan plate reader (integration time 100 ms).

Determination of the Biological Activity of BDNF Containing Fusion Proteins in a SH-SY5Y Neurite Outgrowth Assay The biological activity of BDNF variants and BDNF-containing fusion proteins was determined with a neurite outgrowth assay using human SH-SY5Y neuroblastoma cells. Briefly, SH-SY5Y cells were plated in a 96-well plate at 4000 cells per well in normal growth medium (Ham's F12, 1×non-essential amino acids (PAN), 10% FCS, 2 mM L-glutamine, 1×sodium pyruvate (PAN)) under addition of 10 µM retinoic acid (Sigma) to induce neuronal differentiation. After three days, medium was replaced with growth medium containing different concentrations of BDNF fusion proteins. After three additional days, cells were fixed using 4% paraformaldehyde in PBS for 10 min. at RT, washed, briefly permeabilized (0.1% Triton-X-100), blocked with 1% BSA in PBS and stained for anti-beta-tubulin immunoreactivity using the TuJ1 antibody (Covance) at a dilution of 1:1000 in PBS/i % BSA, followed by three washes and incubation with a Alexa-488-labeled anti-goat antibody (Invitrogen). Numbers of neurites were determined by fluorescence microscopy, evaluating one visual field per well.

Determination of the Binding Activity of an Antibody/Antibody Fragment Containing Fusion Proteins Via FACS The binding activity of BDNF fusion proteins to the respective target receptors (transferrin receptor, IGF-1R) was determined by FACS. Cells expressing the respective receptor (mouse transferrin receptor: MEF-1 mouse embryonal fibroblasts; IGF-1R: 3T3 fibroblasts stably transfected with human IGF-1R) were harvested from their growth media, washed with PBS, and resuspended in FACS buffer (PBS+5% FCS; 100 µL containing $3 \times 10^5$ cells per well of 96-well round-bottom plate). Primary antibody (depending on the BDNF fusion protein used, e.g., anti-human-Fab (Jackson ImmunoResearch) or anti-His6 antibody (Roche)) was added at 1-10 µg/mL and cells incubated for two hours on ice. After three washes with FACS buffer, bound antibody was detected using PE-labeled secondary antibody (Jackson ImmunoResearch, 1:5000-1:10000) for one hour on ice. Cells were washed again and mean fluorescence measured on a FACS Canto cytometer (Becton-Dickinson).

The invention claimed is:

1. A method for producing a recombinant polypeptide, comprising the following steps:
    cultivating a eukaryotic cell comprising a nucleic acid encoding a variant polypeptide wherein the polypeptide has been modified by introducing one or more artificial glycosylation sites located in a specific glycosylation tag that is fused either directly or via a linker to the polypeptide and consists of one of the following amino acid sequences: NGTEGPNFYVPFSNATGVV (SEQ ID NO: 10), NGTEGPNFYVPFSNATGVVR (SEQ ID NO: 16), AAANGTGGA (SEQ ID NO: 17), and NATGADNGTGAS (SEQ ID NO: 19), and
    recovering the variant recombinant polypeptide from the cell or the cultivation medium.

2. The method according to claim 1, wherein the producing steps comprise:
    providing a nucleic acid encoding the polypeptide,
    modifying the nucleic acid to encode a variant polypeptide wherein the amino acid sequence of the polypeptide has been modified to comprise one or more artificial glycosylation sites,
    introducing the nucleic acid into a eukaryotic cell,
    cultivating the eukaryotic cell, and
    recovering the variant recombinant polypeptide from the cell or the cultivation medium and thereby producing the recombinant polypeptide.

3. The method according to claim 1, wherein the eukaryotic cell is a mammalian cell.

4. The method according to claim 2, wherein the eukaryotic cell is a mammalian cell.

* * * * *